(12) United States Patent
Mitsuya et al.

(10) Patent No.: US 7,687,502 B2
(45) Date of Patent: Mar. 30, 2010

(54) SUBSTITUTED QUINAZOLINE OR PYRIDOPYRIMIDINE DERIVATIVE

(75) Inventors: Morihiro Mitsuya, Tsukuba (JP);
Makoto Bamba, Tsukuba (JP);
Yasuhiro Sasaki, Tsukuba (JP);
Teruyuki Nishimura, Ushiku (JP);
Jun-ichi Eiki, Tsuchiura (JP); Keisuke Arakawa, Oyama (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 186 days.

(21) Appl. No.: 10/593,540

(22) PCT Filed: Mar. 23, 2005

(86) PCT No.: PCT/JP2005/005991

§ 371 (c)(1),
(2), (4) Date: May 10, 2007

(87) PCT Pub. No.: WO2005/090332

PCT Pub. Date: Sep. 29, 2005

(65) Prior Publication Data

US 2008/0032996 A1    Feb. 7, 2008

(30) Foreign Application Priority Data

Mar. 23, 2004   (JP) ............... 2004-085808

(51) Int. Cl.
*A61K 31/519* (2006.01)
*A61K 31/497* (2006.01)
*C07D 401/12* (2006.01)
*C07D 403/12* (2006.01)
*C07D 405/12* (2006.01)
*C07D 409/12* (2006.01)
*C07D 413/12* (2006.01)
*C07D 417/14* (2006.01)
*C07D 419/12* (2006.01)
*A61P 3/04* (2006.01)
*A61P 3/10* (2006.01)
*C07D 471/04* (2006.01)
*C07D 513/04* (2006.01)

(52) U.S. Cl. ............ 514/252.02; 514/266.21; 514/266.22; 514/266.23; 514/255.05; 514/264.11; 514/266.2; 514/4; 544/238; 544/284; 544/279

(58) Field of Classification Search ............ 514/252.02, 514/266.21, 266.22, 266.23, 255.05; 544/238, 544/284
See application file for complete search history.

(56) References Cited

U.S. PATENT DOCUMENTS 5,580,870 A * 12/1996 Barker et al. ............ 514/234.5

FOREIGN PATENT DOCUMENTS

WO    WO 02/34744    5/2002

OTHER PUBLICATIONS

Al-Hasani, et al., Viewpoint: Molecular Interventions, Oct. 2003, vol. 3, No. 7, pp. 367-370.*
Johnson, et al., Biochem. Soc. Transac. (2007) vol. 35, #5, 1208-1210.*
Sorenson, et al., J. Histochem. & Cytochem., vol. 55 (6): 555-566, 2007.*
The Center for Disease Control and Prevention, http://www.cdc.gov/nccdphp/publications/factsheets/Prevention/obesity.htm, downloaded Nov. 2, 2008.*
The Office of the Surgeon General, http://www.surgeongeneral.gov/topics/obesity/calltoaction/fact_whatcanyoudo.html, downloaded Nov. 3, 2008.*

* cited by examiner

*Primary Examiner*—Mark L Berch
*Assistant Examiner*—Cecilia M Jaisle
(74) *Attorney, Agent, or Firm*—Richard C. Billups; Catherine D. Fitch

(57) ABSTRACT

The present invention provides a compound having a glucokinase activating action being useful for prevention or treatment of diabetes mellitus, etc. being represented by the formula (I):

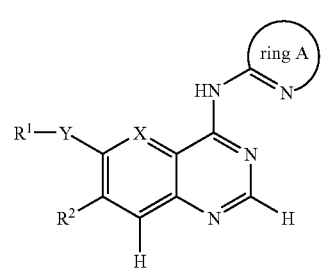

(I)

X is nitrogen atom, etc.; Y is oxygen atom, etc.; $R^1$ is an optionally substituted five to six-membered heteroaryl group, etc.; $R^2$ is hydrogen atom or fluorine atom; and ring A is a monocyclic or bicyclic heteroaryl group which may have a substituent represented by the formula (II)]

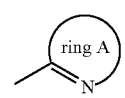

(II)

or a pharmaceutically acceptable salt thereof.

6 Claims, No Drawings

SUBSTITUTED QUINAZOLINE OR PYRIDOPYRIMIDINE DERIVATIVE

TECHNICAL FIELD

The present invention relates to substituted quinazoline or pyridopyrimidine derivatives.

BACKGROUND OF THE INVENTION

Glucokinase (GK) (ATP: D-hexose 6-phosphotransferase, EC2.7.1.1) is one (hexokinase IV) of the four kinds of hexokinases of mammals. Hexokinase is an enzyme in the first stage of glycolysis system and catalyzes the reaction from glucose to glucose hexaphosphate.

Expression of glucokinase is limited mostly to liver and pancreatic beta cells and plays an important role in sugar metabolism by controlling the rate-determining step of glucose metabolism of those cells. Glucokinases of liver and pancreatic beta cells are different in sequences of N-terminal 15 amino acids as a result of difference in splicings but their enzymatic properties are same. In the three hexokinases (I, II and III) other than glucokinase, their enzymatic activity is saturated at the glucose concentration of not more than 1 mM while Km of glucokinase to glucose is 8 mM which is near the physiological blood sugar level.

Accordingly, from the normal blood sugar level (5 mM), an increase in intracellular glucose metabolism takes place via glucokinase in a mode which is correspondent to changes in blood sugar of postcibal blood sugar increase (10 to 15 mM).

With regard to a compound which is structurally related to the compounds of the present invention, a compound represented by the formula (A)

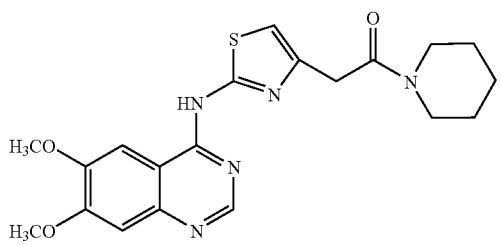

(A)

is, for example, described (refer, for example, to JP-T-2000-501914).

However, the compound represented by the above formula (A) has a methoxy group at 7-position of a quinazoline skeleton but the compound according to the present invention is different from the above in such a respect that it is hydrogen atom or fluorine atom. With regard to a compound where 7-position of a quinazoline skeleton is hydrogen or fluorine atom, there is no specific description therein.

With regard to a compound having a quinazoline skeleton and diabetes mellitus is mentioned as an object disease thereof, a compound represented by the formula (B)

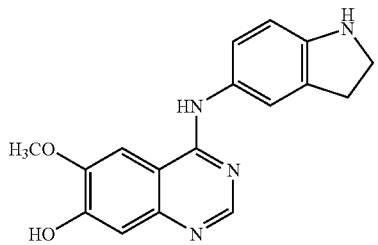

(B)

is, for example, described (refer, for example, to JP-T-2002-536414). The compound represented by the above formula (B) is identical with the compound according to the present invention in such a respect that it has a quinazoline skeleton and has a methoxy group at 6-position of a quinazoline ring. However, the compound represented by the formula (B) has a hydroxyl group at 7-position of a quinazoline ring and a group bonding to an amino group bonded to 4-position of a quinazoline ring is different from that of the compound according to the present invention.

DISCLOSURE OF THE INVENTION

An object of the present invention is to provide a novel substance having a glucokinase-activating action.

The present inventors have found that specific substituted quinazoline or pyridopyrimidine derivatives have a glucokinase-activating action whereupon they have achieved the present invention.

Thus, the present invention provides the compounds mentioned in the following (a) to (i) or a pharmaceutically acceptable salts thereof in order to achieve the above-mentioned object.

(a) A compound represented by the formula (I):

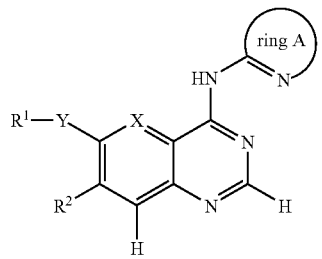

(I)

or a pharmaceutically acceptable salt thereof, wherein:
X is nitrogen atom or CH;
Y is oxygen atom or sulfur atom;
$R^1$ is one group or atom optionally selected from the following (1), (2), (3), (4), (5) and (6):
(1) a five- or six-membered heteroaryl group having one to three hetero atom(s) selected from the group consisting of nitrogen atom, sulfur atom and oxygen atom in a ring;
said heteroaryl group may form a fused ring with phenyl group;
(2) an aryl group;
(3) a straight-chain or branched lower alkyl group;
(4) a cycloalkyl group having 3 to 7 carbon atoms;
one of the carbon atoms constituting said group except for a carbon atom bonding to Y, may be substituted with oxygen atom, NH, N-alkanoyl group or carbonyloxy group;
(5) a straight-chain or branched lower alkenyl group; and
(6) hydrogen atom;
$R^2$ is hydrogen atom or fluorine atom;
ring A is a monocyclic or bicyclic heteroaryl group represented by the formula (II):

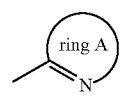

(II)

said heteroaryl group may have one substituent(s), being same or different, selected from a substituent group β;

Substituent group α:
a lower alkyl group optionally substituted with one to three halogen atom(s);
a cycloalkyl group having 3 to 7 carbons;
a lower alkoxy group;
a hyhydroxyl group;
a hydroxyalkyl group;
said hyhydrogen atom of hydroxyl group in said hydroxyalkyl group may be substituted with a lower alkyl group;
an alkanoyl group;
halogen atom;
oxy group;
a lower alkylsulfonyl group;
a lower alkylsulfonylamino group;
a mono- or di-lower alkylcarbamoyl group;
a mono- or di-lower alkylcarbamoylalkyl group;
a mono- or di-lower alkylsulfamoyl group;
amino group;
a mono- or di-lower alkylamino group;
cyano group; and
a five- or six-membered heteroary group which may have one to three hetero atom(s) selected from the group consisting of nitrogen atom, sulfur atom and oxygen atom in a ring
Substituent group β:
a lower alkyl group;
a lower alkoxy group;
halogen atom;
trifluoromethyl group;
a hydroxyalkyl group;
hydrogen atom of hydroxyl group in said hydroxyalkyl group may be substituted with a lower alkyl group;
an aminoalkyl group;
amino group in said aminoalkyl group may be further substituted with a lower alkyl group;
an alkanoyl group;
carboxyl group;
an alkoxycarbonyl group; and
cyano group.

(b) A compound or a pharmaceutically acceptable salt thereof according to the above (a), wherein $R^1$ is a group which is optionally selected from the following (1), (2), (3) and (4):
(1) a five- or six-membered heteroaryl group having one to three hetero atom(s) selected from the group consisting of nitrogen atom, sulfur atom and oxygen atom in a ring;
said heteroaryl group may form a fused ring with phenyl group;
(2) an aryl group;
(3) a straight-chain or branched lower alkyl group; and
(4) a cycloalkyl group having 3 to 7 carbon atoms;
one of the carbon atoms constituting said group except for a carbon atom bonding to Y, may be substituted with oxygen atom, NH, N-alkanoyl group or carbonyloxy group;
said $R^1$ may have one to three group(s), being same or different, selected from the above-mentioned substituent group α.

(c) A compound or a pharmaceutically acceptable salt thereof according to the above (a), wherein $R^1$ is a group which is optionally selected from the following (1) and (2):
(1) a five- or six-membered heteroaryl group having one to three hetero atom(s) selected from the group consisting of nitrogen atom, sulfur atom and oxygen atom in a ring;
said heteroaryl group may form a fused ring with phenyl group; and
(2) an aryl group;
said $R^1$ may have one to three group(s), being same or different, selected from the above-mentioned substituent group α.

(d) A compound or a pharmaceutically acceptable salt thereof according to the above (c), wherein the ring A is thiazolo[5,4-b]pyridinyl group, pyrazinyl group, thiadiazolyl group or pyrazolyl group which may have one to three substituent(s), being same or different, selected from the substituent group β.

(e) A compound or a pharmaceutically acceptable salt thereof according to any one of the above (c) or (d), wherein the formula (I) is a formula (I-1):

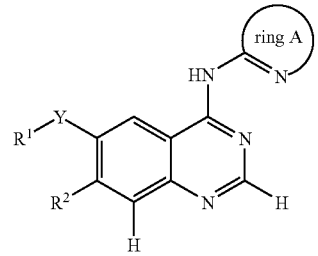

(I-1)

wherein each symbol has the same meaning as above.

(f) A compound or a pharmaceutically acceptable salt thereof according to any one of the above (c) or (d), wherein the formula (I) is a formula (I-2):

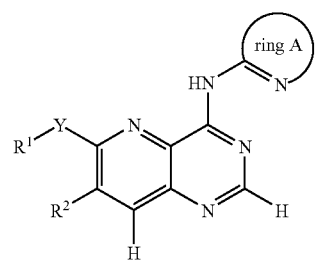

(I-2)

wherein each symbol has the same meaning as above.

(g) A compound or a pharmaceutically acceptable salt thereof according to the above (e), wherein Y is oxygen atom.

(h) A compound or a pharmaceutically acceptable salt thereof according to the above (f), wherein Y is sulfur atom.

(i) A compound or a pharmaceutically acceptable salt thereof according to the above (a), wherein the compound represented by the formula (I) is [6-(4H-[1,2,4]triazol-3-ylsulfanyl)-quinazolin-4-yl]-thiazolo[5,4-b]pyridin-2-yl-amine, [6-(4-methyl-4H-[1,2,4]triazol-3-ylsulfanyl)-quinazolin-4-yl]-thiazol-2-yl-amine, [6-(4-methyl-4H-[1,2,4]triazol-3-ylsulfanyl)-quinazolin-4-yl]-pyrazin-2-yl-amine, (6-phenoxyquinazolin-4-yl)-pyrazin-2-yl-amine, [6-(4H-[1,2,4]triazol-3-ylsulfanyl)-quinazolin-4-yl]-pyrazin-2-yl-amine, [6-(4-methyl-4H-[1,2,4]triazol-3-ylsulfanyl)-quinazolin-4-yl]-thiazolo[5,4-b]pyridin-2-yl-amine, (6-phenoxy-quinazolin-4-yl)-thiazolo[5,4-b]pyridin-2-yl-amine, [6-(2-fluoro-phenoxy)-quinazolin-4-yl]thiazolo-[5,4-b]pyridin-2-yl-amine, [6-(1-methyl-1H-imidazol-2-yl-sulfanyl)-quinazolin-4-yl]-thiazolo[5,4-b]pyridin-2-yl-amine, [6-(pyridin-2-ylsulfanyl)-quinazolin-4-yl]-thiazolo-[5,4-b]pyridin-2-yl-amine, [6-(4-methyl-4H-[1,2,4]triazol-3-ylsulfanyl)-quinazolin-4-yl]-(3-methyl-[1,2,4]thiadiazol-5-yl-amine, [6-(pyrimidin-2-ylsulfanyl)-quinazolin-4-yl]-thiazole[5,4-b]pyridin-2-yl-amine, [6-(4-methyl-4H-[1,2,4]triazol-3-ylsulfanyl)-quinazolin-4-yl]-thiazolo[5,4-b]-pyridin-2-yl-amine, [6-(4-methyl-4H-[1,2,4]triazol-3-ylsulfanyl)-quinazolin-4-yl]-thiazolo[4,5-b]pyrazin-2-yl-amine, benzothiazol-2-yl-[6-(4-methyl-4H-[1,2,4]triazol-3-ylsulfanyl)-quinazolin-4-yl]-amine, [6-(3H-[1,2,3]triazol-4-ylsulfanyl)-quinazolin-4-yl]-thiazolo[5,4-b]pyridin-2-yl-amine, (1-methyl-1H-pyrazol-3-yl)-[6-(4-methyl-4H-[1,2,4]-triazol-3-ylsulfanyl)-quinazolin-4-yl]-amine, [6-(4-methyl-4H-[1,2,4]triazol-3-ylsulfanyl)-quinazolin-4-yl]-pyrimidin-4-yl-amine, (5-methyl-pyrazin-2-yl)-[6-(4-methyl-4H-[1,2,4]triazol-3-ylsulfanyl)-quinazolin-4-yl]-amine, [6-(4-methyl-4H-[1,2,4]triazol-3-ylsulfanyl)-quinazolin-4-yl-pyridin-2-yl]-amine, (5-chloro-thiazol-2-yl)-[6-(4-methyl-4H-[1,2,4]triazol-3-ylsulfanyl)-quinazolin-4-yl]-amine, [6-(2-fluoro-1-fluoro-methyl-ethoxy)-quinazolin-4-yl]-thiazolo[5,4-b]pyridin-2-yl-amine, (6-isopropoxy-quinazolin-4-yl)-pyrazin-2-yl-amine, (6-isopropoxy-quinazolin-4-yl)-thiazolo[5,4-b]pyridin-2-yl-amine, [6-(2-hydroxy-(1S)-methyl-ethoxy-quinazolin-4-yl)]-thiazole[5,4-b]pyridin-2-yl-amine, (6-cyclopentyloxy-quinazolin-4-yl)-thiazolo[5,4-b]pyridin-2-yl-amine, [6-(2-fluoro-1-fluoromethyl-ethoxy)-quinazolin-4-yl]-(1-methyl-1H-pyrazol-3-yl)-amine, [6-(2-fluoro-1-fluoromethyl-ethoxy)-quinazolin-4-yl]-isoxazol-3-yl-amine, [6-(2-fluoro-1-fluoromethyl-ethoxy)-quinazolin-4-yl]-(5-fluoro-thiazolo-[5,4-b]pyridin-2-yl)-amine, [6-(2-fluoro-1-fluoromethyl-ethoxy)-quinazolin-4-yl]-(5-methoxy-thiazolo[5,4-b]pyridin-2-yl)-amine, [6-(4H-[1,2,4]triazol-3-ylsulfanyl)-pyrido-[3,2-d]pyrimidin-4-yl]-thiazolo[5,4-b]pyridin-2-yl-amine, (6-phenoxy-pyrido[3,2-d]pyrimidin-4-yl)-thiazol-2-yl-amine, [6-(4-methyl-4H-[1,2,4]triazol-3-ylsulfanyl)-pyrido[3,2-d]-pyrimidin-4-yl]-thiazol-2-yl-amine, [6-(4-methyl-4H-[1,2,4]triazol-3-ylsulfanyl)-pyrido[3,2-d]pyrimidin-4-yl]-thiazolo[5,4-b]pyridin-2-yl-amine, [6-(5-methyl-4H-[1,2,4]-triazol-3-ylsulfanyl)-pyrido[3,2-d]pyrimidin-4-yl]-thiazolo[5,4-b]pyridin-2-yl-amine, thiazolo[5,4-b]pyridin-2-yl-[6-(3H-[1,2,3]triazol-4-ylsulfanyl)-pyrido[3,2-d]-pyrimidin-4-yl]-amine, (6-methoxy-quinazolin-4-yl)-pyrazin-2-yl-amine, (6-hydroxy-quinazolin-4-yl)-thiazolo[5,4-b]-pyridin-2-yl-amine, 6-(1-methylpyrazol-3-ylsulfanyl)-thiazolo[5,4-b]pyridin-2-yl-amine, 6-(1-methylpyrazol-3-yl-sulfanyl)-thiazolo[5,4-b]pyridin-2-ylpyrido[3,2-d]-pyrimidin-4-yl-amine, (6-ethylsulfanyl)-thiazolo[5,4-b]-pyridin-2-ylpyrido[3,2-d]pyrimidin-4-yl-amine, (5-methoxy-methyl-1,2,4-triazol-3-ylsulfanyl)thiazolo[5,4-b]pyridin-2-ylpyrido[3,2-d]pyrimidin-4-yl-amine, (5-methylpyrazin-2-yl)-6-(1,2,4-triazol-3-ylsulfanyl)pyrido[3,2-d]pyrimidin-4-yl-amine, 6-(1-methylimidazol-2-ylsulfanyl)-(5-methyl-pyrazin-2-yl)pyrido[3,2-d]pyrimidin-4-yl-amine, 6-(imidazol-2-ylsulfanyl)-(5-methylpyrazin-2-yl)pyrido-[3,2-d]pyrimidin-4-yl-amine, 6-(1-ethylimidazol-2-yl-sulfanyl)-(5-methylpyrazin-2-yl)pyrido[3,2-d]pyrimidin-4-yl-amine, (5-methylpyrazin-2-yl)-6-(1-methylpyrazol-3-yl-sulfanyl)pyrido[3,2-d]pyrimidin-4-yl-amine, 6-(1,5-dimethylimidazol-2-ylsulfanyl)-(5-methylpyrazin-2-yl)-pyrido[3,2-d]pyrimidin-4-yl-amine, 6-(4-methylimidazol-2-ylsulfanyl)-(5-methylpyrazin-2-yl)pyrido[3,2-d]pyrimidin-4-yl-amine, (5-methylpyridin-2-yl)-6-(1,2,4-triazol-3-yl-sulfanyl)pyrido[3,2-d]pyrimidin-4-yl-amine, (5-fluoro-pyridin-2-yl)-6-(1,2,4-triazol-3-ylsulfanyl)pyrido[3,2-d]-pyrimidin-4-yl-amine, 6-(pyridin-2-ylsulfanyl)-pyrido-[3,2-d]-pyrimidin-4-yl]-thiazolo[5,4-b]pyridin-2-yl-amine, [6-(1,3,4-thiadiazol-2-ylsulfanyl)-pyrido[3,2-d]pyrimidin-4-yl]-thiazolo[5,4-b]pyridin-2-yl-amine, [6-(1-methyl-1H-tetrazol-5-ylsulfanyl)-pyrido[3,2-d]pyrimidin-4-yl]-thiazolo[5,4-b]pyridin-2-yl-amine, [6-(4H-[1,2,4]triazol-3-ylsulfanyl)-pyrido[3,2-d]pyrimidin-4-yl]-3-methyl-[1,2,4]thiadiazol-5-yl-amine, [6-(4H-[1,2,4]triazol-3-yl-sulfanyl)-pyrido[3,2-d]pyrimidin-4-yl]-(1-methyl-1H-pyrazol-3-yl)-amine, [6-(3-fluoro-benzonitril-2-yl-sulfanyl)-pyrido[3,2-d]pyrimidin-4-yl]-3-methyl-[1,2,4]-thiadiazol-5-yl-amine, [6-(3H-[1,2,3]triazol-4-ylsulfanyl)-pyrido[3,2-d]pyrimidin-4-yl]-(1-methyl-1H-pyrazol-3-yl)-amine, [6-(5-methyl-4H-[1,2,4]triazol-3-ylsulfanyl)-pyrido-[3,2-d]pyrimidin-4-yl]-(1-methyl-1H-pyrazol-3-yl)-amine, [6-(3-chloro-pyridin-2-ylsulfanyl)-pyrido[3,2-d]pyrimidin-4-yl]-(1-methyl-1H-pyrazol-3-yl)-amine, [6-(3-cyano-pyridin-2-ylsulfanyl)-pyrido[3,2-d]pyrimidin-4-yl]-(1-methyl-1H-pyrazol-3-yl)-amine, [6-(3-amido-pyridin-2-ylsulfanyl)-pyrido[3,2-d]pyrimidin-4-yl]-(1-methyl-1H-pyrazol-3-yl)-amine, 6-[(1H-benzimidazol-2-ylsulfanyl)-N-(1-methyl-1H-pyrazol-3-yl)pyrido[3,2-d]pyrimidin-4-yl-amine, 6-[(5-amino-4H-1,2,4-triazol-3-yl)sulfanyl]-N-(1-methyl-1H-pyrazol-3-yl)pyrido[3,2-d]pyrimidin-4-yl-amine, N-pyrazin-2-yl-6-(4H-1,2,4-triazol-3-ylsulfanyl)pyrido-[3,2-d]pyrimidin-4-yl-amine, N-isoxazaol-3-yl-6-(4H-1,2,4-triazol-3-ylsulfanyl)pyrido[3,2-d]pyrimidin-4-yl-amine, 6-{[6-(4H-1,2,4-triazol-3-ylsulfanyl)pyrido[3,2-d]-pyrimidin-4-yl]amino}nicotinonitrile, (4-methyl-1,3-thiazol-2-yl)-6-(4-methyl-1,2,4-triazol-3-ylsulfanyl)-quinazolin-4-yl-amine, (5-methyl-1,3-thiazol-2-yl)-6-(4-methyl-1,2,4-triazol-3-ylsulfanyl)-quinazolin-4-yl-amine, 6-(methylbenzoate-2-yl)sulfanyl-thiazolo[5,4-b]pyridin-2-ylquinazolin-4-yl-amine, 6-(2-hydroxymethylphenylsulfanyl)-thiazolo[5,4-b]pyridin-2-ylquinazolin-4-yl-amine, 6-(pyrazin-2-ylsulfanyl)-thiazolo[5,4-b]pyridin-2-yl-quinazolin-4-yl-amine, 6-(3-fluoropyridin-2-ylsulfanyl)-thiazolo[5,4-b]pyridin-2-ylquinazolin-4-yl-amine, 6-(benzoate-2-ylsulfanyl)-thiazolo[5,4-b]pyridin-2-yl-quinazolin-4-yl-amine, 6-(3-chloropyridin-2-ylsulfanyl)-(1-methylpyrazol-3-yl)quinazolin-4-yl-amine, [6-(2-dimethylamino-ethylsulfanyl)-quinazolin-4-yl]-thiazolo-[5,4-b]pyridin-2-yl-amine, [6-(cyclopentylsulfanyl)-quinozolin-4-yl]-thiazolo[5,4-b]pyridin-4-yl-amine, [6-(2-fluorophenylsulfanyl)-quinazolin-4-yl]-thiazolo[5,4-b]-pyridin-2-yl-amine, [6-(2-methoxyphenylsulfanyl)-quinazolin-4-yl]-thiazolo[5,4-b]pyridin-2-yl-amine, [6-(3-chloropyridin-2-yloxy)-quinazolin-4-yl]-thiazolo[5,4-b]-pyridin-2-yl-amine, [6-(3-cyanopyridin-2-yloxy)-quinazolin-4-yl]-thiazolo[5,4-b]pyridin-2-yl-amine, [6-(3-carboxamido-pyridin-2-yloxy)-quinzaolin-4-yl]-thiazolo[5,4-b]pyridin-2-yl-amine, [6-(pyridin-2-yloxy)-quinazolin-4-yl]-thiazolo-[5,4-b]pyridin-2-yl-amine, [6-(3-methylpyridin-2-yloxy)-quinzaolin-4-yl]-thiazolo[5,4-b]pyridin-2-yl-amine, [6-(methylcarbamoyl-methyloxy)-quinazolin-4-yl]-thiazolo-[5,4-b]pyridin-2-yl-amine, [6-(3-methylsulfonylpyridin-2-yloxy)-quinazolin-4-yl]-thiazolo[5,4-b]pyridin-2-yl-amine, [6-(3-chloropyridin-2-yloxy)-quinazolin-4-yl]-3-methyl-[1,2,4-]thiadiazol-5-yl-amine, [6-(3-fluoropyridin-2-yloxy)-quinazolin-4-yl]-3-methyl-[1,2,4]thiadiazol-5-yl-amine, [6-(3-chloropyridin-2-yloxy)-quinazolin-4-yl]-pyridin-2-yl-amine, [6-(tetrahydro-2H-pyran-4-yloxy)-quinazolin-4-yl]-(1-methyl-1H-pyrazol-3-yl)-amine, [6-(3,5-difluoro-pyridin-2-yloxy)-quinazolin-4-yl]-3-methyl-[1,2,4]thiadiazol-5-yl-amine, [6-(2-chloro-6-(methylsulfonyl)phenoxy)-quinazolin-4-yl]-(1-methyl-1H-pyrazol-3-yl)-amine, [6-(2,4-difluorophenoxy)-quinazolin-4-yl]-(1-methyl-1H-pyrazol-3-yl)-amine, [6-(2-fluoro-6-(5-methyl-[1,2,4]-oxadizol-3-yl)phenoxy)-quinazolin-4-yl]-3-methyl-[1,2,4]-thiadiazol-5-yl-amine, [6-(2-fluoro-6-(methylsulfonyl-phenoxy)-quinazolin-4-yl]-3-methyl-[1,2,4]thiadiazol-5-yl-amine, [6-(2-fluoro-6-(methylsulfonyl)phenoxy)-quinazolin-4-yl]-(1-methyl-1H-pyrazol-3-yl)-amine, [6-(2-fluoro-6-(methylsulfonyl)phenoxy)-quinazolin-4-yl]-(1-ethyl-1H-pyrazol-3-yl)-amine, [6-(2-fluoro-6-(methylsulfonyl)-phenoxy)-quinazolin-4-yl]- pyrazin-2-yl-amine, [6-(2-chloro-6-(methanesulfonylamino) phenoxy)-quinazolin-4-yl]-(1-methyl-1H-pyrazol-3-yl)-amine, 3-fluoro-2-({4-[(pyrazin-2-yl)amino]quinazolin-6-yl}oxy)benzonitrile, [6-(butyllacton-2-yloxy)-quinazolin-4-yl]-(1-methyl-1H-pyrazol-3-yl)-amine, [6-(2,4-difluoro-6-(methylsulfonyl)phenoxy)-quinazolin-4-yl]-(1-methyl-1H-pyrazol-3-yl)-amine, [6-(2-fluoro-6-(methylsulfonyl)phenoxy)-quinazolin-4-yl]-thiazolo[5,4-b]-pyridin-2-yl-amine, N-(1-methyl-1H-pyrazol-3-yl)-6-[2-(methylsulfonyl)phenoxy]quinazolin-6-yl-amine, 3-fluoro-2-({4-[(5-methylpyrazin-2-yl)amino]quinazolin-6-yl}oxy)benzo-nitrile, 6-(3-chloropyridin-2-ylsulfanyl)-(1-methyl-pyrazol-3-yl)quinazolin-4-yl-amine, 6-(3-chloropyridin-2-ylsulfanyl)-(5-methyl-pyrazin-2-yl)quinazolin-4-yl-amine, 6-(3-choropyridin-2-ylsulfanyl)-(1H-pyrazol-3-yl)-quinazolin-4-yl-amine, 6-(acetylpiperidin-4-yl)oxy-N-[1,3]-thiazolo[5,4-d]pyridin-2-ylquinazolin-4-yl-amine, N-(1-methyl-1H-pyrazol-3-yl)-6-(pyrazin-2-yloxy)quinazolin-4-yl-amine, N-(1-methyl-1H-pyrazol-3-yl)-6-(pyrimidin-4-yloxy)-quinazolin-4-yl-amine, 6-[2-fluoro-1-(fluoromethyl) ethoxy]-N-[1,3]thiazolo[5,4-d]pyrimidin-2-ylquinazolin-4-yl-amine, 6-[(3-chloropyridin-2-yl)oxy]-N-1,3-thiazol-2-ylquinazolin-4-amine, (1-methylpyrazol-3-yl)quinazolin-4-yl-amine, 6-(1,3-benzothiazol-2-yloxy)-N-(1-methyl-1H-pyrazol-3-yl)-quinazolin-4-yl-amine, N-(1-methyl-1H-pyrazol-3-yl)-6-(quinazolin-2-yloxy)quinazolin-4-yl-amine, 6-[(5-fluoro-pyridin-2-yl)oxy]-N-(1-methyl-1H-pyrazol-3-yl)quinazolin-4-yl-amine, 6-[(3-chloropyridin-2-yl)oxy]-N-(5-methyl-1H-pyrazol-3-yl)quinazolin-4-yl-amine, N-(1-methyl-1H-pyrazol-3-yl)-6-(pyridin-3-yloxy)quinazolin-4-yl-amine, 6-[(3-chloropyridin-2-yl)oxy]-N-4H-[1,2,4]-triazol-3-yl-quinazolin-4-yl-amine, 6-[(5-fluoropyridin-3-yl)oxy]-N-(1-methyl-1H-pyrazol-3-yl)quinazolin-4-yl-amine, 6-[(3-chloropyridin-2-yl)oxy]-N-[1,2,4]-thiadiazol-5-yl-quinazolin-4-yl-amine, N-(1-methyl-1H-pyrazol-3-yl)-6-[(3-methylpyridin-2-yl)oxy]quinazolin-4-yl-amine, 6-{[3-(di-fluoromethyl)pyridin-2-yl]oxy}-N-(1-methyl-1H-pyrazol-3-yl)quinazolin-4-yl-amine, N-(1-methyl-1H-pyrazol-3-yl)-6-{[3-(trifluoromethyl)pyridin-2-yl]oxy}quinazolin-5-yl-amine, [2-({4-[(1-methyl-1H-pyrazol-3-yl)amino]quinazolin-6-yl}oxy)pyridin-3-yl]methanol, 6-{[3-(fluoromethyl)-pyridin-2-yl]oxy}-N-(1-methyl-1H-pyrazol-3-yl)quinazolin-4-yl-amine, 1-[2-({4-[(1-methyl-1H-pyrazol-3-yl)amino]-quinazolin-6-yl}oxy)pyridin-3-yl]ethanone, 5-chloro-2-methyl-4-({4-[(1-methyl-1H-pyrazol-3-yl)amino]quinazolin-6-yl}oxy)pyridazin-3(2H)-one, 6-[(6-fluoropyridin-2-yl)oxy]-N-(1-methyl-1H-pyrazol-3-yl)quinazolin-4-yl-amine, [3-fluoro-2-({4-[(1-methyl-1H-pyrazol-3-yl)amino]quinazolin-6-yl}oxy)phenyl]methanol, 6-[2-fluoro-6-(fluoromethyl)-phenoxy]-N-(1-methyl-1H-pyrazol-3-yl)quinazolin-4-yl-amine, [3-chloro-4-({4-[(1-methyl-1H-pyrazol-3-yl)amino]-quinazolin-6-yl}oxy)phe-nyl]methanol, methyl 5-(methyl-sulfonyl)-2-({4-[(3-methyl-[1,2,4]-thiadiazol-5-yl)amino]-quinazolin-6-yl}oxy)benzoate, 3-fluoro-2-({4-[(1-pyridin-2-yl-1H-pyrazol-3-yl) amino]quinazolin-6-yl}oxy)benzonitrile, 1-[3-fluoro-2-({4-[(1-methyl-1H-pyrazol-3-yl)amino]-quinazolin-6-yl}oxy)phenyl]ethanone, 6-[(3-chloropyridin-2-yl)oxy]-N-[1-(difluoromethyl)-1H-pyrazol-3-yl]quinazolin-4-yl-amine, 3-chloro-N,N-dimethyl-2-({4-[(3-methyl-[1,2,4]-thiadiazol-5-yl)amino]quinazolin-6-yl}oxy)benzenesulfon-amide, 6-[2-chloro-6-(ethylsulfonyl)phenoxy]-N-(3-methyl-1,2,4-thiadiazol-5-yl)quinazolin-4-yl-amine, 6-[2-fluoro-6-(methylsulfonyl)phenoxy]-N-(5-methylpyrazin-2-yl)-quinazolin-4-yl-amine, 6-[2-chloro-6-(cyclopropylsulfonyl)-phenoxy]-N-(1-methyl-1H-pyrazol-3-yl)quinazolin-4-yl-amine, 6-[2-fluoro-6-(methylsulfonyl)phenoxy]-N-1H-pyrazol-3-yl-quinazolin-4-yl-amine, 6-[3-cyclopropylpyridin-2-yl]oxy)-N-(1-methyl-1H-pyrazol-3-yl)quinazolin-4-yl-amine, [2-({4-[(1-methyl-1H-pyrazol-3-yl)amino]quinazolin-6-yl}oxy)-3-(trifluoroethyl)phenyl]methanol, 6-[2-fluoro-6-(methyl-sulfonyl)phenoxy]-N-pyridazin-3-ylquinazolin-4-yl-amine, N-(5-chloropyrazin-2-yl)-6-[2-fluoro-6-(methylsulfonyl)-phenoxy]quinazolin-4-yl-amine, [3,5-difluoro-4-({4-[(1-methyl-1H-pyrazol-3-yl)amino]quinazolin-6-yl}oxy)phenyl]-methanol, 3-fluoro-2-({4-[(1-methyl-1H-pyrazol-4-yl)amino]-quinazolin-6-yl}oxy)benzonitrile, 6-[4-methyl-2-(methyl-sulfonyl)phenoxy]-N-(1-methyl-1H-pyrazol-3-yl)quinazolin-4-yl-amine, 6-(2,6-difluorophenoxy)-N-(1-methylpyrazol-3-yl)-quinazolin-4-yl-amine, 1-[3-methyl-2-([4-[(1-methyl-pyrazol-3-yl)amino]quinazolin-6-yl]oxy)phenyl]ethanone, 6-[2-(fluoromethyl)-6-(methylsulfonyl)phenoxy]-N-(1-methyl-pyrazol-3-yl)quinazolin-4-yl-amine, 3-methyl-2-({4-[(1-methyl-pyrazol-3-yl)amino]quinazolin-6-yl}oxy)benzonitrile, cyclopropyl[3-fluoro-2-([4-[{1-methyl-pyrazol-3-yl}amino]-quinazolin-6-yl]oxy)phenyl]methanone, 6-[2-fluoro-6-(methoxymethyl)phenoxy]-N-(1-methyl-pyrazol-3-yl)quinazolin-4-yl-amine, [6-(5-chloro-3-fluoropyridin-2-yloxy)-quinazolin-4-yl]-(1-methyl-1H-pyrazol-3-yl)-amine, [6-(3-fluoropyridin-2-yloxy)-quinazolin-4-yl]-(1-methyl-1H-pyrazol-3-yl)-amine, 6-[2-methyl-6-(methylsulfonyl)-phenoxy]-N-(1-methyl-pyrazol-3-yl)quinazolin-4-yl-amine, 6-[2-(fluoromethyl)-6-(methylsulfonyl)phenoxy]-N-(1H-pyrazol-3-yl)quinazolin-4-yl-amine or [6-(2-fluoro-6-(methanesulfonamide) phenoxy)-quinazolin-4-yl]-(1-methyl-1H-pyrazol-3-yl)-amine.

The compounds and pharmaceutically acceptable salts thereof mentioned in the above-mentioned (a) to (i) have a glucokinase activating action. Thus, the present invention provides a glucokinase activator comprising the compounds and pharmaceutically acceptable salts thereof mentioned in the above-mentioned (a) to (i).

From about ten years ago, hypothesis that glucokinase acts as a glucose sensor for pancreatic beta-cells and liver has been proposed (refer, for example, to Garfinkel, D., et al., "Computer modeling identifies glucokinase as glucose sensor of pancreatic beta-cells", *American Journal Physiology*, vol. 247, (3Pt2), 1984, pages 527 to 536). As a result of recent glucokinase gene manipulation mice, it has been made clear that glucokinase actually plays an important role in homeostasis of glucose in total body. Mice where glucokinase gene is destroyed die soon after birth (refer, for example, to Grupe, A, et al. "Transgenic knockouts reveal a critical requirement for pancreatic beta cell glucokinase in maintaining glucose homeostasis", *Cell*, vol. 83, 1995, pages 69 to 78) while, in normal and diabetic mice in which glucokinase is excessively expressed, blood sugar level becomes low (refer, for example, to Ferre, T., et al., "Correction of diabetic alterations by glucokinase", *Proceedings of the National Academy of Sciences of the U.S.A.*, vol. 93, 1996, pages 7225 to 7230). As the glucose concentration rises, although the reactions of pancreatic beta-cells and hepatic cells are different, they both correspond to the direction for lowering the blood sugar level. Pancreatic beta-cells become to secrete more insulin while liver incorporate sugar and to store it as glycogen and, at the same time, it also lowers the release of the sugar.

As such, variation of enzymatic activity of glucokinase plays an important role in glucose homeostasis of mammals via liver and pancreatic beta-cells. In the case where diabetes mellitus appears in young people called MODY 2 (maturity-onset diabetes of the young), mutation of glucokinase gene has been found and lowering of glucokinase activity is a cause of hyperglycemia (refer, for example, to Vionnet, N., "Nonsense mutation in the glucokinase gene causes early-onset non-insulin-dependent diabetes mellitus", *Nature Genetics*, vol. 356, 1992, pages 721-722). On the other hand, families having mutation which rises the glucokinase activity have been also found and those people show hypoglycemia (refer, for example, to Glaser, B., et al., "Familial hyuperinsulinism caused by an activating glucokinase mutation", *New England Journal of Medicine*, vol. 338, 1998, pages 226 to 230).

Those findings show that glucokinase acts as a glucose sensor even in human being and plays an important role for homeostasis of glucose. On the other hand, in many patients suffering from type II diabetes mellitus, it is believed that adjustment of blood sugar level utilizing the glucokinase sensor system is possible. Since glucokinase activating substance is expected to have a promoting action of insulin secretion of pancreatic beta-cells and of sugar incorporation of liver and also to have a suppressive action for sugar release, it is believed that the compounds mentioned in (a) to (i) or pharmaceutically acceptable salts thereof in accordance with the present invention are useful as treating and/or preventive agents for patients suffering from type II diabetes mellitus.

It has been also made clear in recent years that glucokinase of a pancreatic beta-cell type is expressed in a limited manner in brain of rats, particularly in ventromedial hypothalamus (hereinafter, it will be abbreviated as VMH). Nerve cells of about 20% of VMH are called glucose responsive neurons and have been already believed to play an important role in body weight control. When glucose is administered into brain of rats, amount of food ingestion lowers while, when glucose metabolism is suppressed by administration of glucosamine which is an analog of glucose into brain, hyperphagia appears. From electrophysiological experiments, glucose responsive neurons are activated corresponding to changes in physiological glucose concentration (5 to 20 mM) but, when glucose metabolism is suppressed by glucosamine or the like, suppression of activity is noted. In a glucose concentration sensor system of VHM, there is assumed a mechanism via glucokinase the same as in insulin secretion of pancreatic beta-cells.

Those findings suggest that, in addition to liver and pancreatic beta-cells, substances having an glucokinase activating action of VHM have not only blood sugar correcting effect but have a possibility of correction of obesity which has been a problem in many patients suffering from type II diabetes mellitus and it is likely that the compounds according to the present invention are useful not only for type I insulin dependent diabetes but also for type II diabetes which has been unable to achieve a sufficient lowering of the blood sugar level by the conventional agents for diabetes mellitus.

Accordingly, the compounds mentioned in (a) to (i) and pharmaceutically acceptable salts thereof in accordance with the present invention are believed to be useful for the treatment and/or the prevention of obesity.

From the above, the compounds mentioned in (a) to (i) and pharmaceutically acceptable salts thereof in accordance with the present invention have a glucokinase activating action and are useful as therapeutic and/or preventive agents for diabetes mellitus, as therapeutic and/or preventive agents for chronic complications of diabetes such as retinopathy, nephropathy, neuropathy, ischemic cardiac diseases and arteriosclerosis and further as therapeutic and/or preventive agents for obesity.

Complications of diabetes mellitus used here mean diseases accompanied by onset of diabetes mellitus and examples of complications of diabetes mellitus as such are diabetic retinopathy, diabetic nephropathy, diabetic neuropathy and diabetic arteriosclerosis.

BEST MODE FOR CARRYING OUT THE INVENTION

Firstly, meaning of the terms used in the present specification will be illustrated and then the compounds according to the present invention will be illustrated.

"Aryl group" is a $C_{6-14}$ hydrocarbon ring aryl group, etc. and is, for example, phenyl group or naphthyl group.

"Lower alkyl group" is a $C_{1-6}$ straight-chain or branched alkyl group and its examples are methyl group, ethyl group, propyl group, isopropyl group, butyl group, isobutyl group, sec-butyl group, tert-butyl group, pentyl group, isoamyl group, neopentyl group, isopentyl group, 1,1-dimethylpropyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,2,2-trimethylpropyl group and 1-ethyl-2-methylpropyl group.

"Cycloalkyl group" is a $C_{3-7}$ cycloalkyl group and its examples are cyclopropyl group, cyclobutyl group, cyclopentyl group, cyclohexyl group and cycloheptyl group.

"Lower alkenyl group" is a $C_{1-6}$ straight-chain or branched lower alkenyl group and its examples are vinyl group, allyl group, 1-butenyl group, 2-butenyl group and 1-pentenyl group.

"Lower alkoxy group" is a group where hydrogen atom of hydroxyl group is substituted with the above-mentioned lower alkyl group and its examples are methoxy group, ethoxy group, propoxy group, isopropoxy group, butoxy group, sec-butoxy group, tert-butoxy group, pentyloxy group, isopentyloxy group, hexyloxy group and isohexyloxy group.

"Heteroaryl group" is a $C_{5-6}$ monocyclic one having 1 to 3 hetero atom(s) selected from oxygen atom, sulfur atom and nitrogen atom in a ring or a bicyclic heteroaryl group where the hateroaryl group of said monocyclic one is fused with benzene or pyridine ring and its examples are furyl group, thienyl group, pyrrolyl group, imidazolyl group, triazolyl group, thiazolyl group, thiadiaolyl group, isothiazolyl group, oxazolyl group, isoxazolyl group, pyridyl group, pyrimidinyl group, pyridazinyl group, pyrazolyl group, pyrazinyl group, quinolinyl group, isoquinolinyl group, quinazolinyl group, quinolidinyl group, quinoxalinyl group, cinnolinyl group, benzimidazolyl group, imidazopyridyl group, benzofuranyl group, naphthylidinyl group, 1,2-benzoisoxazolyl group, benzoxazolyl group, benzothiazolyl group, oxaxolopyridyl group, thiazolopyridyl group, thiazolopyrazinyl group, isothiazolopyridyl group and benzothienyl group.

"Halogen atom" is, for example, fluorine atom, chlorine atom, bromine atom, iodine atom, etc.

"Hydroxyalkyl group" is a group where one of hydrogen atoms in the above-mentioned lower alkyl group is substituted with hydroxyl group and its examples are hydroxymethyl group, 2-hydroxyethyl group, 1-hydroxypropyl group, 1-hydroxyethyl group, 2-hydroxypropyl group and 2-hydroxy-1-methyl-ethyl group.

"Aminoalkyl group" is a group where one of hydrogen atoms in the above-mentioned alkyl group is substituted with an amino group and its examples are aminomethyl group, aminoethyl group and aminopropyl group.

"Alkanoyl group" is a group where the above-mentioned lower alkyl group is bonded to carbonyl group and its examples are methylcarbonyl group, ethylcarbonyl group, propylcarbonyl group and isopropylcarbonyl group.

"Alkoxycarbonyl group" is a group where hydrogen atom of carboxyl group is substituted with the above-mentioned lower alkyl group and its examples are methoxycarbonyl group, ethoxycarbonyl group, propylcarbonyl group and isopropylcarbonyl group.

"Lower alkylsulfonyl group" is a group where the above-identified lower alkyl group with sulfonyl group and its examples are methylsulfonyl group, ethylsulfonyl group, propylsulfonyl group and isopropylsulfonyl group.

"Cycloalkylsulfonyl group" is a group where the above-mentioned cycloalkyl group is bonded to sulfonyl group and its examples are cyclopropylsulfonyl group, cyclobutylsulfonyl group and cyclopentylsulfonyl group.

"Mono lower alkylcarbamoyl group" is a group where carbamoyl group is mono-substituted with the above lower alkyl group and its examples are methylcarbamoyl group, ethylcarbamoyl group, propylcarbamoyl group, isopropylcarbamoyl group, butylcarbamoyl group, sec-butylcarbamoyl group and tert-butylcarbamoyl group.

"Di lower alkylcarbamoyl group" is a carbamoyl group which is di-substituted with the above lower alkyl groups being same or different and its examples are dimethylcarbamoyl group, diethylcarbamoyl group, ethylmethylcarbamoyl group, dipropylcarbamoyl group, methylpropylcarbamoyl group and diisopropylcarbamoyl group.

"Mono lower alkylamino group" is an amino group which is mono-substituted with the above lower alkyl group and its examples are methylamino group, ethylamino group, propylamino group, isopropylamino group, butylamino group, sec-butylamino group and tert-butylamino group.

"Di lower alkylamino group" is an amino group which is di-substituted with the above lower alkyl groups being same or different and its examples are dimethylamino group, diethylamino group, dipropylamino group, methylpropylamino group and diisopropylamino group.

"Aminoalkyl group" is, for example, aminomethyl group, 1-aminoethyl group and 2-aminoethyl group.

Now, in order to more specifically disclose the compound represented by the formula (I) according to the present invention, referential characters used for the formula (I) will be illustrated.

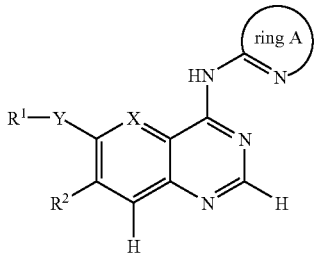

(I)

wherein each symbol has the same meaning as above.

$R^1$ is one group or atom optionally selected from the following (1), (2), (3), (4), (5) and (6):

(1) a five- or six-membered heteroaryl group having one to three hetero atom(s) selected from the group consisting of nitrogen atom, sulfur atom and oxygen atom in a ring;

said heteroaryl group may form a fused ring with phenyl group;

(2) an aryl group;

(3) a straight-chain or branched lower alkyl group;

(4) a cycloalkyl group having 3 to 7 carbon atoms;

one of the carbon atoms constituting said group except for a carbon atom bonding to Y, may be substituted with oxygen atom, NH, N-alkanoyl group or carbonyloxy group;

(5) a straight-chain or branched lower alkenyl group; and (6) hydrogen atom.

Specific examples of "a five- or six-membered heteroaryl group having one to three hetero atom(s) selected from the group consisting of nitrogen atom, sulfur atom and oxygen atom in a ring" for $R^1$ are isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group and pyrazolyl group. Among them, triazolyl group, imidazolyl group, thiazolyl group and pyridyl group are preferred and triazolyl group is more preferred.

The heteroaryl group may also form a 9- or 10-membered bicyclic heteroaryl group by fusing with the same or different heteroaryl group or aryl group.

Examples of the 9- or 10-membered heteroaryl group are isoquinolyl group, isoindolyl group, indolyl group, quinolyl group, thiazolopyridyl group, thiazolopyrazinyl group, benzoimidazolyl group, benzoxazolyl group, benzothiazolyl group, benzotriazolyl group, benzofuranyl group, imidazopyridinyl group and triazopyridinyl group.

Specific examples of "aryl group" for $R^1$ are phenyl group, naphthyl group and biphenyl group. Among them, phenyl or naphthyl group is preferred and phenyl group is more preferred.

Examples of "straight-chain or branched lower alkyl group" for $R^1$ are methyl group, ethyl group, propyl group and isopropyl group.

"$C_{3-7}$ cycloalkyl group" for $R^1$ may be a group which is the same as the already-defined cycloalkyl group, a group where one or two carbon atom(s) constituting the above-defined $C_{3-7}$ cycloalkyl group (excluding the carbon atom bonding to Y) is/are substituted with oxygen atom, nitrogen atom, N-alkanoyl group or carbonyloxy group or a group which have one or two double bond(s) in the ring.

Examples of the $R^1$ are tetrahydrofuranyl group, tetrahydropyranyl group, pyrrolidinyl group, piperidinyl group, N-acetylpiperidinyl group and 3,4-dihydro-pyridazinyl group. Among them, tetrahydrofuranyl group, tetrahydropyranyl group, N-acetylpiperidnyl group or 3,4-dihydro-pyridazinyl group is preferred.

With regard to the "straight-chain or branched lower alkeuyl group" for $R^1$, propenyl group, isopropenyl group and isobutenyl group are preferred and isopropenyl group is more preferred. With regard to $R^1$, among the above-mentioned (1) to (6), the preferred one is (1) a five- or six-membered heteroaryl group having one to three hetero atom(s) selected from the group consisting of nitrogen atom, sulfur atom and oxygen atom in a ring;

said heteroaryl group may form a fused ring with phenyl group;

(2) an aryl group;

(3) a straight-chain or branched lower alkyl group; or (4) a cycloalkyl group having 3 to 7 carbon atoms;

one of the carbon atoms constituting said group except for a carbon atom bonding to Y, may be substituted with oxygen atom, NH, N-alkanoyl group or carbonyloxy group; and one or two double bond(s) may be present in the ring;

and more preferred one is (1) a five- or six-membered heteroaryl group having one to three hetero atom(s) selected from the group consisting of nitrogen atom, sulfur atom and oxygen atom in a ring;

said heteroaryl group may form a fused ring with phenyl group; or (2) an aryl group.

When $R^1$ is the above-mentioned (1) to (5), $R^1$ may have one to three substituent(s), being same or different, selected from the following substituent group α:

Substituent group α:
- a lower alkyl group optionally substituted with one to three halogen atom(s);
- a cycloalkyl group having 3 to 7 carbons;
- a lower alkoxy group;
- a hyhydroxyl group;
- a hydroxyalkyl group;

said hyhydrogen atom of hydroxyl group in said hydroxyalkyl group may be substituted with a lower alkyl group;
- an alkanoyl group;
- halogen atom;
- oxy group;
- a lower alkylsulfonyl group;
- a lower alkylsulfonylamino group;
- a mono- or di-lower alkylcarbamoyl group;
- a mono- or di-lower alkylcarbamoylalkyl group;
- a mono- or di-lower alkylsulfamoyl group;
- amino group;
- a mono- or di-lower alkylamino group;
- cyano group; and
- a five- or six-membered heteroary group which may have one to three hetero atom(s) selected from the group consisting of nitrogen atom, sulfur atom and oxygen atom in a ring "Lower alkyl group" in the substituent group means the same group as the above-identified lower alkyl group or the group where the above-identified lower alkyl group is substituted with one to three halogen atom(s).

Examples of the lower alkyl group are methyl group, ethyl group, isopropyl group, propyl group, 2-fluoro-1-fluoromethyl-ethyl group, trifluoromethyl group and fluoromethyl group.

"$C_{3-7}$ cycloalkyl group" in the substituent group means the same group as the above-defined cycloalkyl group and specific examples thereof are cyclopropyl group, cyclobutyl group and cyclopentyl group.

"Lower alkoxy group" in the substituent group means the same group as the already-defined lower alkoxy group and specific examples thereof are methoxy group, ethoxy group, isopropoxy group and propoxy group.

"Hydroxy lower alkyl group" in the substituent group means the same group as the already-defined hydroxyalkyl group or a group where hydrogen atom of hydroxyl group in the above-defined hydroxyalkyl group is substituted with a lower alkyl group and its specific examples are 2-hydroxyethyl group, 1-hydroxypropyl group, 1-hydroxyethyl group, methoxymethyl group and ethoxymethyl group.

"Alkanoyl group" in the substituent group means the same group as the above-defined alkanoyl group or a group where the above-defined cycloalkyl group is bonded to carbonyl group and its specific examples are methylcarbonyl group, ethylcarbonyl group, propylcarbonyl group, isopropylcarbonyl group and cyclopropylcarbonyl group.

"Halogen atom" in the substituent group means the same group as the above-defined halogen atom and its specific examples are fluorine atom, chlorine atom and bromine atom.

"Lower alkylsulfonyl group" in the substituent group means the same group as the above-defined lower alkylsulfonyl group and its specific examples are methylsulfonyl group, ethylsulfonyl group, propylsulfonyl group and isopropylsulfonyl group.

"Lower alkylsulfonylamino group" in the substituent group means the group where the above-defined lower alkylsulfonylamino group is bonded to amino group and its specific examples are methylsulfonylamino group, ethanesulfonylamino group and isopropylsulfonylamino group.

"Mono lower alkylcarbamoyl group" in the substituent group means the same group as the above-defined mono lower alkylcarbamoyl group and its specific examples are methylcarbamoyl group, ethylcarbamoyl group, propylcarbamoyl group, isopropylcarbamoyl group, butylcarbamoyl group, sec-butylcarbamoyl group and tert-butylcarbamoyl group.

"Di lower alkylcarbamoyl group" in the substituent group means the same group as the above-defined di lower alkylcarbamoyl group and its specific examples are dimethylcarbamoyl group, diethylcarbamoyl group, ethylmethylcarbamoyl group, dipropylcarbamoyl group, methylpropylcarbamoyl group and diisopropylcarbamoyl group.

"Mono lower alkylcarbamoylalkyl group" in the substituent group means the group where the above-defined mono lower alkylcarbamoylalkyl group is bonded to alkyl group and its specific examples are methylcarbamoylmethyl group, ethylcarbamoylmethyl group and propylcarbamoylmethyl group.

"Di lower alkylcarbamoylalkyl group" in the substituent group means the group where the above-defined di lower alkylcarbamoylalkyl group is bonded to alkyl group and its specific examples are dimethylcarbamoylmethyl group, diethylcarbamoylmethyl group and ethylmethylcarbamoylmethyl group.

"Mono lower alkylsulfamoyl group" in the substituent group means a group where one of hydrogen atoms in NH of the sulfamoyl group is substituted with the above-defined lower alkyl group and its specific examples are methylsulfamoyl group, ethylsulfamoyl group and isopropylsulfamoyl group.

"Di lower alkylsulfamoyl group" in the substituent group means a group where two hydrogen atoms in NH of the sulfamoyl group are substituted with the above-defined lower alkyl groups being same or different and its specific examples are dimethylsulfamoyl group, ethylmethylsulfamoyl group, diethylsulfamoyl group and diisopropylsulfamoyl group.

"Mono lower alkylamino group" in the substituent group means the same group as the above-defined mono lower alkylamino group and its specific examples are methylamino group, ethylamino group, propylamino group and isopropylamino group.

"Di lower alkylamino group" in the substituent group means the same group as the above-defined di lower alkylamino group and its specific examples are dimethylamino group, diethylamino group depropylamino and methylpropylamino group.

Y is oxygen atom or sulfur atom.

From the above, examples of —Y—$R^1$ are [1,2,4]triazol-3-ylsulfanyl group, 4-methyl-[1,2,4]-triazol-3-ylsulfanyl group, 5-methyl-[1,2,4]triazol-3-ylsulfanyl group, 5-methoxymethyl-[1,2,4]triazol-3-ylsulfanyl group, 5-amino-[1,2,4]triazol-3-ylsulfanyl group, [1,2,3]triazol-3-ylsulfanyl group, [1,3,4]thiadiazol-3-ylsulfanyl group, 1-ethyl-imidazol-2-ylsulfanyl group, 1-methyl-imidazol-2-yl-sulfanyl group, 1,5-dimethyl-imidazol-2-ylsulfanyl group, imidazol- 2-ylsulfanyl group, 3-methyl-imidazol-2-ylsulfanyl group, 1-methylpyrazol-2-ylsulfanyl group, pyridin-2-yl-sulfanyl group, pyrimidin-2-ylsulfanyl group, pyrazin-2-yl-sulfanyl group, 3-cyanopyridin-2-ylsulfanyl group, 3-carbamoylpyridin-3-ylsulfanyl group, 3-fluoropyridin-3-ylsulfanyl group, 3-chloropyridin-3-ylsulfanyl group, 1-methyl-1H-tetrazol-5-ylsulfanyl group, phenylsulfanyl group, 2-fluorophenylsulfanyl group, 2-methoxycarbonyl-phenylsulfanyl group, 2-cyanophenylsulfanyl group, 2-methoxy-phenylsulfanyl group, 2-hydroxymethylphenylsulfanyl group, benzoic acid-2-ylsulfanyl group, methylsulfanyl group, ethylsulfanyl group, isopropylsulfanyl group, cyclopentylsulfanyl group, cyclohexylsulfanyl group, 2-dimethylamino-ethylsulfanyl group, benzimidazol-2-yl-sulfanyl group, 3-chloropyridin-2-yloxy group, 4-chloropyridin-2-yloxy group, 3-carbamoylpyridin-2-yloxy group, 3-cyanopyridin-2-yloxy group, 3-methylpyridin-2-yl-oxy group, 3-methylsulfonylpyridin-2-yloxy group, 3-difluoro-methylpyridin-2-yloxy group, pyridin-2-yloxy group, pyridin-3-yloxy group, 4-trifluoromethyl-pyridin-3-yloxy group, 3-hydroxymethyl-pyridin-2-yloxy group, 3-fluoro-methylpyridin-2-yloxy group, 3-cyclopropyl-pyridin-2-yloxy group, 3-methoxycarbonylpyridin-2-yloxy group, 3-fluoro-pyridin-2-yloxy group, 5-fluoropyridin-2-yloxy group, 5-fluoropyridin-3-yloxy group, 1,5-difluoropyridin-2-yloxy group, 2,5-chloro-3-fluoropyridin-2-yloxy group, pyrimidin-2-yloxy group, pyrazin-2-yloxy group, phenoxy group, 2-fluorophenoxy group, 2,4-dichlorophenoxy group, 2,6-difluorophenoxy group, 2-acetyl-6-methylphenoxy group, 2-fluoro-6-hydroxymethylphenoxy group, 2-fluoro-6-fluoro-methylphenoxy group, 2-cyano-6-fluorophenoxy group, 2-cyano-6-methylphenoxy group, 2-chloro-4-hydroxymethylphenoxy group, 2-acetyl-6-fluoro-phenoxy group, 2-chloro-6-methylsulfonyl-phenoxy group, 2-chloro-6-ethanesulfonylphenoxy group, 2-chloro-6-cyclopropylsulfonylphenoxy group, 2-methyl-sulfonylphenoxy group, 2-fluoro-6-methylsulfonylphenoxy group, 2-fluoro-4-methylsulfonylphenoxy group, 2-fluoromethyl-6-methylsulfonylphenoxy group, 2-methylsulfonyl-4-methylphenoxy group, 4-methylsulfonyl-2-methoxycarbonylphenoxy group, 2-cyclopropylcarbonyl-6-fluorophenoxy group, 2-chloro-6-(methylsulfonylamino)-phenoxy group, 2,6-dichloro-4-hydroxymethylphenoxy group, 2-fluoro-6-(5-methyl-[1,2,4]oxadiazol-3-yl)phenoxy group, ethoxy group, isopropoxy group, 2-methoxy-1-methyl-ethoxy group, 1-methoxymethyl-propoxy group, 3-hydroxy-1-methyl-propoxy group, 1-hydroxymethyl-propoxy group, 2-amino-1-ethoxy group, 2-hydroxy-propoxy group, 2-methoxy-propoxy group, 2-hydroxy-1-methyl-ethoxy group, 2-hydroxy-ethoxy group, 2-dimethylamino-1-methyl-ethoxy group, 2-fluoro-1-fluoromethyl-ethoxy group, 2-fluoro-1-methyl-ethoxy group, methylcarbamoylmethyloxy group, cyclopentyloxy group, cyclohexyloxy group, cycloheptyloxy group, 2-hydroxy-cyclopentyloxy group, tetrahydropyran-4-yloxy group, butyrolactone-2-yloxy group, 1-acetylpiperidin-4-yloxy group, 3-allyloxy group, 3-isopropenyloxy group, 1-methylallyloxy group, hydroxyl group, benzothiazol-2-yloxy group, quinazolin-2-yloxy group and 5-chloro-2-methyl-3-oxo-2,3-dihydro-pyridazin-2-yloxy group. Among them, preferred examples are cyclopentyloxy group, isopropoxy group, 2-methoxy-1-methyl-ethoxy group, 2-hydroxy-1-methyl-ethoxy group, 2-fluoro-1-fluoromethyl-ethoxy group, phenyl-sulfanyl group, phenoxy group, 2-fluorophenoxy group, 4H-[1,2,4]triazol-3-ylsulfanyl group, 5-methyl-[1,2,4]triazol-3-ylsulfanyl group, 4-methyl-4H-[1, 2,4]triazol-3-ylsulfanyl group, 3H-[1,2,3]triazol-4-yl-sulfanyl group, imidazol-2-ylsulfanyl group, pyridin-2-yl-sulfanyl group, 1-methylpyrazol-3-ylsulfanyl group, 3-chloropyridin-2-yloxy group, 2-fluoro-6-(methylsulfonyl)-phenoxy group, 2-chloro-6-(methylsulfonylamino)phenoxy group, 5-chloro-2-methyl-3-oxo-2,3-dihydro-pyridazin-4-yloxy group, 2-fluoro-6-fluoromethylphenoxy group, 2-cyano-6-fluoro-phenoxy group, 2-fluoro-6-methylsulfonylphenoxy group, 2,6-difluoro-4-hydorxymethylphenoxy group, 2,6-difluoro-phenoxy group, 2-fluoromethyl-6-methylsulfonylphenoxy group, 2-cyclopropylcarbonyl-6-fluorophenoxy group and 3-fluoro-pyridin-2-yloxy group. More preferred examples are 2-hydroxy-1-methyl-ethoxy group, 2-fluoro-1-fluoromethyl-ethoxy group, 2-fluoro-phenoxy group, 4H-[1,2,4]triazol-3-ylsulfanyl group, 5-methyl-[1,2,4]triazol-3-ylsulfanyl group, 4-methyl-4H-[1,2,4]triazol-3-ylsulfanyl group, 2-fluoro-6-(methylsulfonyl)phenoxy group, 2-chloro-6-(methylsulfonyl-amino)phenoxy group, 3-chloropyridin-2-yloxy group, 5-chloro-2-methyl-3-oxo-2,3-dihydro-pyridazin-4-yloxy group, 2-fluoro-6-fluoromethylphenoxy group, 2-cyano-6-fluoro-phenoxy group, 2-fluoro-6-methylsulfonylphenoxy group, 2,6-difluoro-4-hydroxymethylphenoxy group, 2,6-difluoro-phenoxy group, 2-fluoromethyl-6-methylsulfonylphenoxy group, 2-cyano-6-methylphenoxy group, 2-cyclopropylcarbonyl-6-fluorophenoxy group and 3-fluoropyridin-2-yloxy group.

X is nitrogen atom or H.

With regard to X and Y, it is preferred that X is CH and that, when Y is oxygen atom or, X is nitrogen atom and further that Y is sulfur atom.

$R^2$ is hydrogen atom or fluorine atom and, among them, it is preferred to be hydrogen atom.

"Mono- or bicyclic heteroaryl group" of the ring A means that, among the above heteroaryl group shown by $R^1$, a monocyclic or bicyclic heteroaryl group represented by the formula (II)

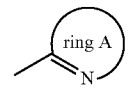

(II)

where it is bonded to 4-position of quinazoline or pyridopyrimidine skeleton in the formula (I).

Said heteroaryl group is a five- or six-membered monocyclic heteroaryl group which may have one to three hetero atom(s) selected from the group consisting of nitrogen atom, sulfur atom and oxygen atom in each ring or is a nine- or ten-membered bicyclic heteroaryl group.

Specific examples of the ring A are thiazolyl group, imidazolyl group, isothiazolyl group, thiadiazolyl group, triazolyl group, oxazolyl group, isoxazolyl group, pyrazinyl group, pyridyl group, pyridazinyl group, pyrazolyl group, pyrimidinyl group, thiazolopyridyl group, thiazolopyrazinyl group and benzothiazolyl group. Among them, preferred ones are thiazolyl group, thiadiazolyl group, isoxazolyl group, pyrazinyl group, thiazolopyridyl group, pyrazolyl group and pyridyl group and more preferred ones are thiazolopyridyl group, thiadiazolyl group, pyrazinyl group and pyrazolyl group.

The ring A may also have one to three substituent(s), being same or different, selected from the above-mentioned substituent group β.

"Lower alkyl group" in the substituent group is the same group as the already-defined lower alkyl group and its examples are methyl group, ethyl group, propyl group and isopropyl group.

"Lower alkoxy group" in the substituent group is the same group as the already-defined lower alkoxy group and its examples are methoxy group, ethoxy group, propoxy group and isopropoxy group.

"Halogen atom" in the substituent group is the same group as the already-defined halogen atom and its examples are fluorine atom, chlorine atom and bromine atom.

"Hydroxyalkyl group" in the substituent group is the same group as the already-defined hydroxyalkyl group or is a group where hydrogen atom of hydroxy group in the already-defined hydroxyalkyl group is further substituted with the already-defined lower alkyl group and its examples are hydroxymethyl group, hydroxyethyl group, methoxymethyl group and ethoxymethyl group.

"Aminoalkyl group" in the substituent group is the same group as the already-defined aminoalkyl group or a group where an amino group in the already-defined aminoalkyl group is further substituted with the already-defined lower alkyl group and its examples are aminomethyl group, 1-aminoethyl group, 2-aminoethyl group, methylaminoethyl group and dimethylaminoethyl group.

"Alkanoyl group" in the substituent group is the same group as the already-defined alkanoyl group and its examples are methylcarbonyl group, ethylcarbonyl group, propylcarbonyl group and isopropylcarbonyl group.

"Alkoxycarbonyl group" in the substituent group is a group where the already-defined lower alkoxy group is bonded to carbonyl group and its examples are methoxycarbonyl group, ehtoxycarbonyl group, isopropoxycarbonyl group and propyloxycarbonyl group.

From the above, with regard to a group represented by the following formula (II-1)

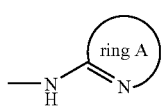

(II-1)

which may have one to three substituent(s) selected from the substituent group β, its specific examples are thiazolo[5,4-b]pyridin-2-ylamino group, 5-fluoro-thiazolo[5,4-b]pyridin-2-ylamino group, 5-methoxy-thiazolo[5,4-b]pyridin-2-ylamino group, thiazol-2-ylamino group, pyradin-2-ylamino group, 3-methyl-[1,2,4]triazol-5-ylamino group, pyrimidin-4-ylamino group, 5-methyl-pyrazin-2-ylamino group, 5-chloropyrazin-2-ylamino group, 1-methyl-1H-pyrazol-3-ylamino group, 1-ethyl-1H-pyrazol-3-ylamino group, 5-methyl-1H-pyrazol-3-ylamino group, 1-(pyridin-2-yl)-1H-pyrazol-3-ylamino group, 1-(difluoromethyl)-1H-pyrazol-3-ylamino group, 1-methyl-1H-pyrazol-5-ylamino group, pyridin-2-ylamino group, 5-methylpyridin-2-ylamino group, 5-fluoropyridin-2-ylamino group, 5-chloro-thiazol-2-ylamino group, isoxazole-3-ylamino group, [1,2,4]thiadiazol-5-ylamino group, 3-methyl-[1,2,4]-thiadiazol-5-ylamino group, 5-cyanopyridin-2-ylamino group, 4-methylthiazol-2-ylamino group, 4H-[1,2,4]triazol-3-ylamino group and pyridazin-3-ylamino group. Among them, preferred ones are thiazolo[5,4-b]pyridin-2-ylamino group, 5-fluoro-thiazolo[5,4-b]pyridin-2-ylamino group, 5-methoxy-thiazolo-[5,4-b]pyridin-2-ylamino group, pyrazin-2-ylamino group, 5-methyl-pyrazin-2-ylamino group, 5-chloropyrazin-2-ylamino group, 1-methyl-1H-pyrazol-3-ylamino group, 1-ethyl-1H-pyrazol-3-ylamino group, 5-methyl-1H-pyrazol-3-ylamino group, 1-(pyridin-2-yl)-1H-pyrazol-3-ylamino group, 1-(difluoromethyl)-1H-pyrazol-3-ylamino group, 1-methyl-1H-pyrazol-5-ylamino group, [1,2,4]thiadiazol-5-ylamino group and 3-methyl-[1,2,4]thiadiazol-5-ylamino group.

With regard to the compound represented by the formula (I) in accordance with the present invention, its specific examples are [6-(4H-[1,2,4]triazol-3-yl-sulfanyl)-quinazolin-4-yl]-thiazolo[5,4-b]pyridin-2-yl-amine, [6-(4-methyl-4H-[1,2,4]triazol-3-ylsulfanyl)-quinazolin-4-yl]-thiazol-2-yl-amine, [6-(4-methyl-4H-[1,2,4]triazol-3-ylsulfanyl)-quinazolin-4-yl]-pyrazin-2-yl-amine, (6-phenoxyquinazolin-4-yl)-pyrazin-2-yl-amine, [6-(4H-[1,2,4]triazol-3-ylsulfanyl)-quinazolin-4-yl]-pyrazin-2-yl-amine, [6-(4-methyl-4H-[1,2,4]triazol-3-ylsulfanyl)-quinazolin-4-yl]-thiazolo[5,4-b]pyridin-2-yl-amine, (6-phenoxy-quinazolin-4-yl)-thiazolo[5,4-b]pyridin-2-yl-amine, [6-(2-fluoro-phenoxy)-quinazolin-4-yl]thiazolo-[5,4-b]pyridin-2-yl-amine, [6-(1-methyl-1H-imidazol-2-yl-sulfanyl)-quinazolin-4-yl]-thiazolo[5,4-b]pyridin-2-yl-amine, [6-(pyridin-2-ylsulfanyl)-quinazolin-4-yl]-thiazolo-[5,4-b]pyridin-2-yl-amine, [6-(4-methyl-4H-[1,2,4]triazol-3-ylsulfanyl)-quinazolin-4-yl]-(3-methyl-[1,2,4]thiadiazol-5-yl-amine, [6-(pyrimidin-2-ylsulfanyl)-quinazolin-4-yl]-thiazolo[5,4-b]pyridin-2-yl-amine, [6-(4-methyl-4H-[1,2,4]-triazol-3-ylsulfanyl)-quinazolin-4-yl]-thiazolo[5,4-b]-pyridin-2-yl-amine, [6-(4-methyl-4H-[1,2,4]triazol-3-yl-sulfanyl)-quinazolin-4-yl]-thiazolo[4,5-b]pyrazin-2-yl-amine, benzothiazol-2-yl-[6-(4-methyl-4H-[1,2,4]triazol-3-ylsulfanyl)-quinazolin-4-yl]-amine, [6-(3H-[1,2,3]triazol-4-ylsulfanyl)-quinazolin-4-yl]-thiazolo[5,4-b]pyridin-2-yl-amine, (1-methyl-1H-pyrazol-3-yl)-[6-(4-methyl-4H-[1,2,4]-triazol-3-ylsulfanyl)-quinazolin-4-yl]-amine, [6-(4-methyl-4H-[1,2,4]triazol-3-ylsulfanyl)-quinazolin-4-yl]-pyrimidin-4-yl-amine, (5-methyl-pyrazin-2-yl)-[6-(4-methyl-4H-[1,2,4]triazol-3-ylsulfanyl)-quinazolin-4-yl]-amine, [6-(4-methyl 4H-[1,2,4]triazol-3-ylsulfanyl)-quinazolin-4-yl]-pyridin-2-yl-amine, (5-chloro-thiazol-2-yl)-[6-(4-methyl-4H-[1,2,4]triazol-3-ylsulfanyl)-quinazolin-4-yl]-amine, [6-(2-fluoro-1-fluoro-methyl-ethoxy)-quinazolin-4-yl]-thiazolo[5,4-b]pyridin-2-yl-amine, (6-isopropoxy-quinazolin-4-yl)-pyrazin-2-yl-amine, (6-isopropoxy-quinazolin-4-yl)-thiazolo[5,4-b]pyridin-2-yl-amine, [6-(2-hydroxy-(1S)-methyl-ethoxy-quinazolin-4-yl)]-thiazole[5,4-b]pyridin-2-yl-amine, (6-cyclopentyloxy-quinazolin-4-yl)-thiazolo[5,4-b]pyridin-2-yl-amine, [6-(2-fluoro-1-fluoromethyl-ethoxy)-quinazolin-4-yl]-(1-methyl-1H-pyrazol-3-yl)-amine, [6-(2-fluoro-1-fluoromethyl-ethoxy)-quinazolin-4-yl]-isoxazol-3-yl-amine, [6-(2-fluoro-1-fluoromethyl-ethoxy)-quinazolin-4-yl]-(5-fluoro-thiazolo-[5,4-b]pyridin-2-yl)-amine, [6-(2-fluoro-1-fluoromethyl-ethoxy)-quinazolin-4-yl]-(5-methoxy-thiazolo[5,4-b]pyridin-2-yl)-amine, [6-(4H-[1,2,4]triazol-3-ylsulfanyl)-pyrido-[3,2-d]pyrimidin-4-yl]-thiazolo[5,4-b]pyridin-2-yl-amine, (6-phenoxy-pyrido[3,2-d]pyrimidin-4-yl)-thiazol-2-yl-amine, [6-(4-methyl-4H-[1,2,4]triazol-3-ylsulfanyl)-pyrido[3,2-d]-pyrimidin-4-yl]-thiazol-2-yl-amine, [6-(4-methyl-4H-[1,2,4]triazol-3-ylsulfanyl)-pyrido[3,2-d]pyrimidin-4-yl]-thiazolo[5,4-b]pyridin-2-yl-amine, [6-(5-methyl-4H-[1,2,4]-triazol-3-ylsulfanyl)-pyrido[3,2-d]pyrimidin-4-yl]-thiazolo[5,4-b]pyridin-2-yl-amine, thiazolo[5,4-b]pyridin-2-yl-[6-(3H-[1,2,3]triazol-4-ylsulfanyl)-pyrido[3,2-d]-pyrimidin-4-yl]-amine, (6-methoxy-quinazolin-4-yl)-pyrazin-2-yl-amine, (6-hydroxy-quinazolin-4-yl)-thiazolo[5,4-b]-pyridin-2-yl-amine, 6-(1-methylpyrazol-3-yl-sulfanyl)-thiazolo[5,4-b]pyridin-2-ylpyrido[3,2-d]-pyrimidin-4-yl-amine, (6-ethylsulfanyl)-thiazolo[5,4-b]-pyridin-2-ylpyrido[3,2-d]pyrimidin-4-yl-amine, (5-methoxy-methyl-1,2,4-triazol-3-ylsulfanyl)thiazolo[5,4-b]pyridin-2-ylpyrido[3,2-d]pyrimidin-4-yl-amine, (5-methylpyrazin-2-yl)-6-(1,2,4-triazol-3-ylsulfanyl)pyrido[3,2-d]pyrimidin-4-yl-amine, 6-(1-methylimidazol-2-ylsulfanyl)-(5-methyl-pyrazin-2-yl)pyrido[3,2-d]pyrimidin-4-yl-amine, 6-(imidazol-2-ylsulfanyl)-(5-methylpyrazin-2-yl)pyrido-[3,2-d]pyrimidin-4-yl-amine, 6-(1-ethylimidazol-2-yl-sulfanyl)-(5-methylpyrazin-2-yl)pyrido[3,2-d]pyrimidin-4-yl-amine, (5-methylpyrazin-2-yl)-6-(1-methylpyrazol-3-ylsulfanyl)pyrido[3,2-d]pyrimidin-4-yl-amine, 6-(1,5-dimethylimidazol-2-ylsulfanyl)-(5-methylpyrazin-2-yl)-pyrido[3,2-d]pyrimidin-4-yl-amine, 6-(4-methylimidazol-2-ylsulfanyl)-(5-methylpyrazin-2-yl)pyrido[3,2-d]pyrimidin-4-yl-amine, (5-methylpyridin-2-yl)-6-(1,2,4-triazol-3-ylsulfanyl)pyrido[3,2-d]pyrimidin-4-yl-amine, (5-fluoro-pyridin-2-yl)-6-(1,2,4-triazol-3-ylsulfanyl)pyrido[3,2-d]-pyrimidin-4-yl-amine, 6-(pyridin-2-ylsulfanyl)-pyrido-[3,2-d]pyrimidin-4-yl]-thiazolo[5,4-b]pyridin-2-yl-amine, [6-(1,3,4-thiadiazol-2-ylsulfanyl)-pyrido[3,2-d]pyrimidin-4-yl]-thiazolo[5,4-b]pyridin-2-yl-amine, [6-(1-methyl-1H-tetrazol-6-ylsulfanyl)-pyrido[3,2-d]pyrimidin-4-yl]-thiazolo[5,4-b]pyridin-2-yl-amine, [6-(4H-[1,2,4]triazol-3-ylsulfanyl)-pyrido[3,2-d]pyrimidin-4-yl]-3-methyl-[1,2,4]thiadiazol-5-yl-amine, [6-(4H-[1,2,4]triazol-3-yl-sulfanyl)-pyrido[3,2-d]pyrimidin-4-yl]-(1-methyl-1H-pyrazol-3-yl)-amine, [6-(3-fluoro-benzonitril-2-yl-sulfanyl)-pyrido[3,2-d]pyrimidin-4-yl]-3-methyl-[1,2,4]-thiadiazol-5-yl-amine, [6-(3H-[1,2,3]triazol-4-ylsulfanyl)-pyrido[3,2-d]pyrimidin-4-yl]-(1-methyl-1H-pyrazol-3-yl)-amine, [6-(5-methyl-4H-[1,2,4]triazol-3-ylsulfanyl)-pyrido-[3,2-d]pyrimidin-4-yl]-(1-methyl-1H-pyrazol-3-yl)-amine, [6-(3-chloro-pyridin-2-ylsulfanyl)pyrido[3,2-d]pyrimidin-4-yl]-(1-methyl-1H-pyrazol-3-yl)-amine, [6-(3-cyano-pyridin-2-ylsulfanyl)-pyrido[3,2-d]pyrimidin-4-yl]-(1-methyl-1H-pyrazol-3-yl)-amine, [6-(3-amido-pyridin-2-yl-sulfanyl)-pyrido[3,2-d]pyrimidin-4-yl]-(1-methyl-1H-pyrazol-3-yl)-amine, 6-[(1H-benzimidazol-2-ylsulfanyl)-N-(1-methyl-1H-pyrazol-3-yl)pyrido[3,2-d]pyrimidin-4-yl-amine, 6-[(5-amino-4H-1,2,4-triazol-3-yl)sulfanyl]-N-(1-methyl-1H-pyrazol-3-yl)pyrido[3,2-d]pyrimidin-4-yl-amine, N-pyrazin-2-yl-6-(4H-1,2,4-triazol-3-ylsulfanyl)pyrido-[3,2-d]pyrimidin-4-yl-amine, N-isoxazaol-3-yl-6-(4H-1,2,4-triazol-3-ylsulfanyl)pyrido[3,2-d]pyrimidin-4-yl-amine, 6-{[6-(4H-1,2,4-triazol-3-ylsulfanyl)pyrido[3,2-d]-pyrimidin-4-yl]amino}nicotinonitrile, (4-methyl-1,3-thiazol-2-yl)-6-(4-methyl-1,2,4-triazol-3-yl-sulfanyl)-quinazolin-4-yl-amine, (5-methyl-1,3-thiazol-2-yl)-6-(4-methyl-1,2,4-triazol-3-ylsulfanyl)-quinazolin-4-yl-amine, 6-(methylbenzoate-2-yl)sulfanyl-thiazolo[5,4-b]pyridin-2-ylquinazolin-4-yl-amine, 6-(2-hydroxymethylphenylsulfanyl)-thiazolo[5,4-b]pyridin-2-ylquinazolin-4-yl-amine, 6-(pyrazin-2-ylsulfanyl)-thiazolo[5,4-b]pyridin-2-yl-quinazolin-4-yl-amine, 6-(3-fluoropyridin-2-ylsulfanyl)-thiazolo[5,4-b]pyridin-2-ylquinazolin-4-yl-amine, 6-(benzoate-2-ylsulfanyl)-thiazolo[5,4-b]pyridin-2-yl-quinazolin-4-yl-amine, 6-(3-chloropyridin-2-ylsulfanyl)-(1-methylpyrazol-3-yl)quinazolin-4-yl-amine, [6-(2-dimethylamino-ethylsulfanyl)-quinazolin-4-yl]-thiazolo-[5,4-b]pyridin-2-yl-amine, [6-(cyclopentylsulfanyl)-quinozolin-4-yl]-thiazolo[5,4-b]pyridin-4-yl-amine, [6-(2-fluorophenylsulfanyl)-quinazolin-4-yl]-thiazolo[5,4-b]-pyridin-2-yl-amine, [6-(2-methoxyphenylsulfanyl)-quinazolin-4-yl]-thiazolo[5,4-b]pyridin-2-yl-amine, [6-(3-chloropyridin-2-yloxy)-quinazolin-4-yl]-thiazolo[5,4-b]-pyridin-2-ylamine, [6-(3-cyanopyridin-2-yloxy)-quinazolin-4-yl]-thiazolo[5,4-b]pyridin-2-yl-amine, [6-(3-carboxamido-pyridin-2-yloxy)-quinzaolin-4-yl]-thiazolo[5,4-b]pyridin-2-yl-amine, [6-(pyridin-2-yloxy)-quinazolin-4-yl]-thiazolo-[5,4-b]pyridin-2-yl-amine, [6-(3-methylpyridin-2-yloxy)-quinzaolin-4-yl]-thiazolo[5,4-b]pyridin-2-yl-amine, [6-(methylcarbamoyl-methyloxy)-quinazolin-4-yl]-thiazolo-[5,4-b]pyridin-2-yl-amine, [6-(3-methylsulfonylpyridin-2-yloxy)-quinazolin-4-yl]-thiazolo[5,4-b]pyridin-2-yl-amine, [6-(3-chloropyridin-2-yloxy)-quinazolin-4-yl]-3-methyl-[1,2,4-]thiazol-5-ylamine, [6-(3-fluoropyridin-2-yloxy)-quinazolin-4-yl]-3-methyl-[1,2,4]thiadiazol-5-yl-amine, [6-(3-chloropyridin-2-yloxy)-quinazolin-4-yl]-pyridin-2-yl-amine, [6-(tetrahydro-2H-pyran-4-yloxy)-quinazolin-4-yl]-(1-methyl-1H-pyrazol-3-yl)-amine, [6-(3,5-difluoro-pyridin-2-yloxy)-quinazolin-4-yl]-3-methyl-[1,2,4]thiadiazol-5-yl-amine, [6-(2-chloro-6-(methylsulfonyl)phenoxy)-quinazolin-4-yl]-(1-methyl-1H-pyrazol-3-yl)-amine, [6-(2,4-difluorophenoxy)-quinazolin-4-yl]-(1-methyl-1H-pyrazol-3-yl)-amine, [6-(2-fluoro-6-(5-methyl-[1,2,4]-oxadizol-3-yl)phenoxy)-quinazolin-4-yl]-3-methyl-[1,2,4]-thiadiazol-5-yl-amine, [6-(2-fluoro-4-(methylsulfonyl-phenoxy)-quinazolin-4-yl]-3-methyl-[1,2,4]thiadiazol-5-yl-amine, [6-(2-fluoro-6-(methylsulfonyl)phenoxy)-quinazolin-4-yl]-(1-methyl-1H-pyrazol-3-yl)-amine, [6-(2-fluoro-6-(methylsulfonyl)phenoxy)-quinazolin-4-yl]-(1-ethyl-1H-pyrazol-3-yl)-amine, [6-(2-fluoro-6-(methylsulfonyl)-phenoxy)-quinazolin-4-yl]-pyrazin-2-yl-amine, [6-(2-chloro-6-(methanesulfonylamino)phenoxy)-quinazolin-4-yl]-(1-methyl-1H-pyrazol-3-yl)-amine, 3-fluoro-2-({4-[(pyrazin-2-yl)amino]quinazolin-6-yl}oxy)benzonitrile, [6-(butyllacton-2-yloxy)-quinazolin-4-yl]-(1-methyl-1H-pyrazol-3-yl)-amine, [6-(2,4-difluoro-6-(methylsulfonyl)phenoxy)-quinazolin-4-yl]-(1-methyl-1H-pyrazol-3-yl)-amine, [6-(2-fluoro-6-(methylsulfonyl)phenoxy)-quinazolin-4-yl]-thiazolo[5,4-b]-pyridin-2-yl-amine, N-(1-methyl-1H-pyrazol-3-yl)-6-[2-(methylsulfonyl)phenoxy]quinazolin-6-yl-amine, 3-fluoro-2-({4-[(5-methylpyrazin-2-yl)amino]quinazolin-6-yl}oxy)benzo-nitrile, 6-(3-chloropyridin-2-ylsulfanyl)-(1-methyl-pyrazol-3-yl)quinazolin-4-yl-amine, 6-(3-chloropyridin-2-ylsulfanyl)-(5-methyl-pyrazin-2-yl)quinazolin-4-yl-amine, 6-(3-chloropyridin-2-ylsulfanyl)-(1H-pyrazol-3-yl)-quinazolin-4-yl-amine, 6-(acetylpiperidin-4-yl)oxy-N-[1,3]-thiazolo[5,4-d]pyridin-2-ylquinazolin-4-yl-amine, N-(1-methyl-1H-pyrazol-3-yl)-6-(pyrazin-2-yloxy)quinazolin-4-yl-amine, N-(1-methyl-1H-pyrazol-3-yl)-6-(pyrimidin-4-yloxy)-quinazolin-4-yl-amine, 6-[2-fluoro-1-(fluoromethyl)ethoxy]-N-[1,3]thiazolo[5,4-d]pyrimidin-2-ylquinazolin-4-yl-amine, 6-[(3-chloropyridin-2-yl)oxy]-N-1,3-thiazol-2-ylquinazolin-4-amine(1-methylpyrazol-3-yl)quinazolin-4-yl-amine, 6-(1,3-benzothiazol-2-yloxy)-N-(1-methyl-1H-pyrazol-3-yl)-quinazolin-4-yl-amine, N-(1-methyl-1H-pyrazol-3-yl)-6-(quinazolin-2-yloxy)quinazolin-4-yl-amine, 6-[(5-fluoro-pyridin-2-yl)oxy]-N-(1-methyl-1H-pyrazol-3-yl)quinazolin-4-yl-amine, 6-[(3-chloropyridin-2-yl)oxy]-N-(5-methyl-1H-pyrazol-3-yl)quinazolin-4-yl-amine, N-(1-methyl-1H-pyrazol-3-yl)-6-(pyridin-3-yloxy)quinazolin-4-yl-amine, 6-[(3-chloropyridin-2-yl)oxy]-N-4H-[1,2,4]-triazol-3-yl-quinazolin-4-yl-amine, 6-[(5-fluoropyridin-3-yl)oxy]-N-(1-methyl-1H-pyrazol-3-yl)quinazolin-4-yl-amine, 6-[(3-chloropyridin-2-yl)oxy]-N-[1,2,4]-thiadiazol-5-yl-quinazolin-4-yl-amine, N-(1-methyl-1H-pyrazol-3-yl)-6-[(3-methylpyridin-2-yl)oxy]quinazolin-4-yl-amine, 6-{[3-(di-fluoromethyl)pyridin-2-yl]oxy}-N-(1-methyl-1H-pyrazol-3-yl)quinazolin-4-yl-amine, N-(1-methyl-1H-pyrazol-3-yl)-6-{[3-(trifluoromethyl)pyridin-2-yl]oxy}quinazolin-4-yl-amine, [2-({4-[(1-methyl-1H-pyrazol-3-yl)amino]quinazolin-6-yl}oxy)pyridin-3-yl]methanol, 6-{[3-(fluoromethyl)-pyridin-2-yl]oxy}-N-(1-methyl-1H-pyrazol-3-yl)quinazolin-4-yl-amine, 1-[2-({4-[(1-methyl-1H-pyrazol-3-yl)amino]-quinazolin-6-yl}oxy)pyridin-3-yl]ethanone, 5-chloro-2-methyl-4-({4-[(1-methyl-1H-pyrazol- 3-yl)amino]quinazolin-6-yl}oxy)pyridazin-3(2H)-one, 6-[(6-fluoropyridin-2-yl)oxy]-N-(1-methyl-1H-pyrazol-3-yl)quinazolin-4-yl-amine, [3-fluoro-2-({4-[(1-methyl-1H-pyrazol-3-yl)amino]quinazolin-6-yl}oxy)phenyl]methanol, 6-[2-fluoro-6-(fluoromethyl)-phenoxy]-N-(1-methyl-1H-pyrazol-3-yl)quinazolin-4-yl-amine, [3-chloro-4-({4-[(1-methyl-1H-pyrazol-3-yl)amino]-quinazolin-6-yl}oxy)phenyl]methanol, methyl 5-(methyl-sulfonyl)-2-({4-[(3-methyl-[1,2,4]-thiadiazol-5-yl)amino]-quinazolin-6-yl}oxy)benzoate, 3-fluoro-2-({4-[(1-pyridin-2-yl-1H-pyrazol-3-yl)amino]quinazolin-6-yl}oxy)benzonitrile, 1-[3-fluoro-2-({4-[(1-methyl-1H-pyrazol-3-yl)amino]-quinazolin-6-yl}oxy)phenyl]ethanone, 6-[(3-chloropyridin-2-yl)oxy]-N-[1-(difluoromethyl)-1H-pyrazol-3-yl]quinazolin-4-yl-amine, 3-chloro-N,N-dimethyl-2-({4-[(3-methyl-[1,2,4]-thiadiazol-5-yl)amino]quinazolin-6-yl}oxy)benzenesulfon-amide, 6-[2-chloro-6-(ethylsulfonyl)phenoxy]-N-(3-methyl-1,2,4-thiadiazol-5-yl)quinazolin-4-yl-amine, 6-[2-fluoro-6-(methylsulfonyl)phenoxy]-N-(5-methylpyrazin-2-yl)-quinazolin-4-yl-amine, 6-[2-chloro-6-(cyclopropylsulfonyl)-phenoxy]-N-(1-methyl-1H-pyrazol-3-yl)quinazolin-4-yl-amine, 6-[2-fluoro-6-(methylsulfonyl)phenoxy]-N-1H-pyrazol-3-yl-quinazolin-4-yl-amine, 6-[3-cyclopropylpyridin-2-yl]oxy)-N-(1-methyl-1H-pyrazol-3-yl)quinazolin-4-yl-amine, [2-({4-[(1-methyl-1H-pyrazol-3-yl)amino]quinazolin-6-yl}oxy)-3-(trifluoroethyl)phenyl]methanol, 6-[2-fluoro-6-(methyl-sulfonyl)phenoxy]-N-pyridazin-3-ylquinazolin-4-yl-amine, N-(5-chloropyrazin-2-yl)-6-[2-fluoro-6-(methylsulfonyl)-phenoxy]quinazolin-4-yl-amine, [3,5-difluoro-4-({4-[(1-methyl-1H-pyrazol-3-yl)amino]quinazolin-6-yl}oxy)phenyl]-methanol, 3-fluoro-2-({4-[(1-methyl-1H-pyrazol-5-yl)amino]-quinazolin-6-yl}oxy)benzonitrile, 6-[4-methyl-2-(methylsulfonyl)phenoxy]-N-(1-methyl-1H-pyrazol-3-yl)quinazolin-4-yl-amine, 6-(2,6-difluorophenoxy)-N-(1-methylpyrazol-3-yl)-quinazolin-4-yl-amine, 1-[3-methyl-2-([4-[(1-methylpyrazol-3-yl)amino]quinazolin-6-yl]oxy)phenyl]ethanone, 6-[2-(fluoromethyl)-6-(methylsulfonyl)phenoxy]-N-(1-methyl-pyrazol-3-yl)quinazolin-4-yl-amine, 3-methyl-2-({4-[(1-methylpyrazol-3-yl)amino]quinazolin-6-yl}oxy)benzonitrile, cyclopropyl [3-fluoro-2-([4-[{1-methylpyrazol-3-yl}amino]-quinazolin-6-yl]oxy)phenyl]methanone, 6-[2-fluoro-6-(methoxymethyl)phenoxy]-N-(1-methylpyrazol-3-yl) quinazolin-4-yl-amine, [6-(5-chloro-3-fluoropyridin-2-yloxy)-quinazolin-4-yl]-(1-methyl-1H-pyrazol-3-yl)-amine, [6-(3-fluoropyridin-2-yloxy)-quinazolin-4-yl]-(1-methyl-1H-pyrazol-3-yl)-amine, 6-[2-methyl-6-(methylsulfonyl)-phenoxy]-N-(1-methylpyrazol-3-yl)quinazolin-4-yl-amine, 6-[2-(fluoromethyl)-6-(methylsulfonyl)phenoxy]-N-(1H-pyrazol-3-yl)quinazolin-4-yl-amine and [6-(2-fluoro-6-(methanesulfonamide)phenoxy)-quinazolin-4-yl]-(1-methyl-1H-pyrazol-3-yl)-amine. Among them, preferred examples are [6-(4H-[1,2,4]triazol-3-ylsulfanyl)-quinazolin-4-4-yl]-thiazole[5,4-b]pyridin-2-yl-amine, [6-(3H-[1,2,3]triazol-4-ylsulfanyl)-quinazolin-4-4-yl]-thiazolo[5,4-b]pyridin-2-ylamine[6-(2-fluoro-1-fluoromethyl-ethoxy)-quinozolin-4-yl]-thiazolo[5,4-b]pyridin-2-yl-amine, [6-(2-hydroxy-(1S)-methyl-ethoxy-quinazolin-4-yl)]-thiazolo[5,4-b]pyridin-2-yl-amine, [6-(4H-[1,2,4]triazol-3-ylsulfanyl)-pyrido-[3,2-d]pyrimidin-4-yl]-thiazolo[5,4-b]pyridin-2-yl-amine, (5-methylpyrazin-2-yl)-6-(1,2,4-triazol-3-ylsulfanyl)-pyrido[3,2-d]pyrimidin-4-yl-amine, (5-methylpyrazin-2-yl)-6-(1-methylpyrazol-3-ylsulfanyl) pyrido[3,2-d]pyrimidin-4-yl-amine, [6-(4H-[1,2,4]triazol-3-ylsulfanyl)-pyrido-[3,2-d]pyrimidin-4-yl]-(1-methyl-1H-pyrazol-3-yl)-amine, [6-(2-fluoro-6-(methylsulfonyl) phenoxy)-quinazolin-4-yl]-(1-methyl-1H-pyrazol-3-yl)-amine, [6-(2-fluoro-6-(methyl-sulfonyl)phenoxy)-quinazolin-4-yl]-(1-ethyl-1H-pyrazol-3-yl)-amine, [6-(2-chlor-6-(methanesulfonylamino)phenoxy)-quinazolin-4-yl]-(1-methyl-1H-pyrazol-3-yl)-amine, 6-(3-chloropyridin-2-ylsulfanyl)-(1-methylpyrazol-3-yl)-quinazolin-4-yl-amine, 6-(3-chloropyridin-2-yl)sulfanyl-(1H-pyrazol-3-yl)quinazolin-4-yl-amine, 5-chloro-2-methyl-4-({4-[(1-methyl-1H-pyrazol-3-yl)amino]quinazolin-6-yl}-oxy)pyridazin-3(2H)-one, 6-[2-fluoro-6-(fluoromethyl)-phenoxy]-N-(1-methyl-1H-pyrazol-3-yl)quinazolin-4-yl-amine, 1-[3-fluoro-2-({4-[(1-methyl-1H-pyrazol-3-yl)amino]-quinazolin-6-yl}oxy)phenyl]ethanone, 6-[(3-chloropyridin-2-yl)oxy]-N-[1-(difluoromethyl)-1H-pyrazol-3-yl]quinazolin-4-yl-amine, 6-[2-chloro-6-(ethylsulfonyl)phenoxy]-N-(3-methyl-1,2,4-thiadiazol-5-yl)quinazolin-4-yl-amine, 6-[2-fluoro-6-(methylsulfonyl)phenoxy]-N-(5-methylpyrazin-2-yl)-quinazolin-4-yl-amine, 6-[2-fluoro-6-(methylsulfonyl)-phenoxy]-N-1H-pyrazol-3-ylquinazolin-4-yl-amine, [3,5-di-fluoro-4-({4-[(1-methyl-1H-pyrazol-3-yl)amino]quinazolin-6-yl}oxy)phenyl]methanol, 6-(2,6-difluorophenoxy)-N-(1-methylpyrazol-3-yl)quinazolin-4-yl-amine, 1-[3-methyl-2-([4-[(1-methylpyrazol-3-yl)amino]quinazolin-6-yl]oxy)-phenyl]ethanone, 6-[2-(fluoromethyl)-6-(methylsulfonyl)-phenoxy]-N-(1-methyl-pyrazol-3-yl)quinazolin-4-yl-amine, 3-methyl-2-({4-[(1-methylpyrazol-3-yl)amino]quinazolin-6-yl}oxy)benzonitrile, cyclopropyl[3-fluoro-2-([4-[{1-methyl-pyrazol-3-yl}amino]quinazolin-6-yl]oxy)phenyl]methanone, [6-(3-fluoropyridin-2-yloxy)-quinazolin-4-yl]-(1-methyl-1H-pyrazol-3-yl)-amine, 3-fluoro-2-({4-[(pyrazin-2-yl)amino]-quinazolin-6-yl}oxy)benzonitrile, 6-[2-methyl-6-(methyl-sulfonyl)phenoxy]-N-(1-methyl-pyrazol-3-yl)quinazolin-4-yl-amine, 6-[2-(fluoromethyl)-6-(methylsulfonyl)phenoxy]-N-(1H-pyrazol-3-yl)quinazolin-4-yl-amine and [6-(2-fluoro-6-(methanesulfonamide)phenoxy)-quinazolin-4-yl]-(1-methyl-1H-pyrazol-3-yl)-amine.

Incidentally, with regard to preferred embodiments of the above-illustrated $R^1$, $R^2$, X, Y, ring A, substituent group α and substituent group β, any of them may be combined.

Among the compounds according to the present invention, the compound represented by the formula (I-3)

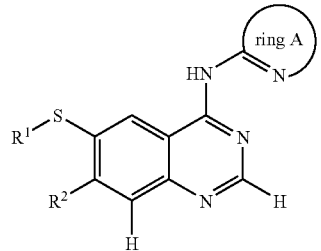

(I-3)

may be manufactured by, for example, the following process.

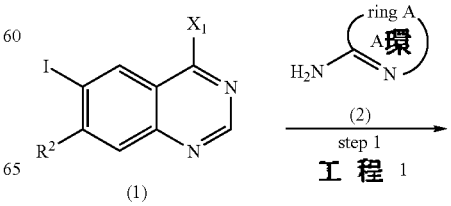

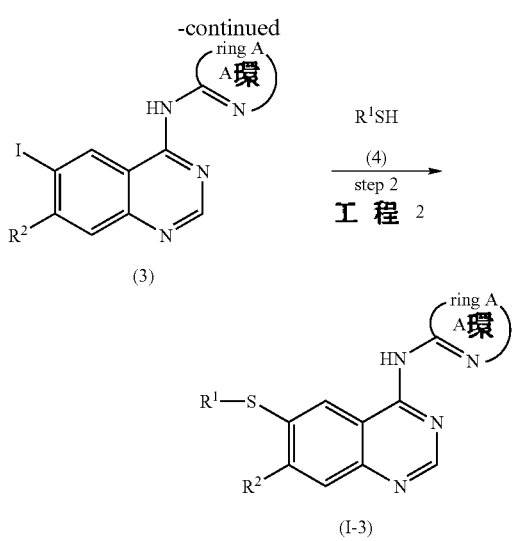

In the formulae, $X_1$ is halogen atom and other symbols as the same as those defined already.

(Step 1) This is a step where the compound (1) is made to react with the compound (2) to produce the compound (3).

$X_1$ in the compound (2) is preferred to be chlorine atom.

Amount of the compound (2) used in this step to one equivalent of the compound (1) is usually 0.5 to 10 equivalent(s) and, preferably, 1 to 3 equivalent(s).

Reaction time is usually 0.1 to 24 hour(s) and, preferably 1 to 10 hour(s).

Reaction temperature is usually from room temperature to boiling point of the solvent or 200° C. and, preferably, 80 to 150° C.

There is no particular limitation for the reaction solvent so far as it does not affect the reaction and, to be more specific, its examples are phenol, toluene, xylene, N,N-dimethylformamide (hereinafter, abbreviated as DMF), N,N-dimethylacetamide (hereinafter, abbreviated as DMA), N-methylpyrrolidone (hereinafter, abbreviated as NMP), tetrahydrofuran (hereinafter, abbreviated as THF), dioxane, dimethoxyethane, ethanol, isopropanol, butanol, methylene chloride and chloroform. Among them, phenol, ethanol and isopropanol are preferred and phenol is more preferred.

The compound (3) prepared as such is able to be subjected to the next step with or without isolation and purification by known separating and purifying means such as concentration, concentration in vacuo, re-precipitation, extraction with solvent, crystallization or chromatography.

(Step 2) This is a step where the compound (3) is made to react with a thiol compound (4) in the presence of a base and a copper salt to produce the compound (I-3) according to the present invention.

Examples of the copper salt used in this step are copper iodide, copper bromide, copper chloride and copper oxide.

Amount of the copper salt used in this step to one equivalent of the compound (3) is usually 0.01 to 20 equivalent(s), preferably 0.1 to 3 equivalent(s) and, more preferably, 0.2 to 1 equivalent.

Examples of the base used in this step are a tertiary aliphatic amine such as triethylamine, N,N-diisopropyl-ethylamine, N,N-dimethylaniline, 1,8-diazabicyclo[5,4,0]-undeca-7-ene (DBU) and 1,5-azabicyclo[4,3,0]nona-5-ene (DBN); an aromatic amine such as pyridine, 4-dimethylaminopyridine, picoline, lutidine, quinoline and isoquinoline; an alkali metal alkoxide such as potassium tert-butylate, sodium ethylate and sodium methylate; an alkalimetal hydroxide such as potassium hydroxide and sodium hydroxide and an alkali metal carbonate such as potassium carbonate, sodium carbonate and cesium carbonate. Among them, alkali metal carbonate and aromatic amine such as pyridine are preferred and potassium carbonete, cesium carbonate, pyridine, etc. are more preferred.

Amount of the base used in this step varies depending upon the amount of the compound (3) used and upon the type of the solvent and, to one equivalent of the compound (3), it is usually 0.5 to 10 equivalent(s), preferably 1 to 5 equivalent(s) and, more preferably, 1 to 3 equivalent(s).

Reaction time is usually 0.1 to 50 hour(s), preferably 0.5 to 20 hour(s) and, more preferably, 1 to 10 hour(s).

Reaction temperature is usually 50 to 200° C., preferably 80 to 170° C. and, more preferably, 100 to 160° C.

There is no particular limitation for the reaction solvent so far as it does not effect the reaction and its examples are DMA, DMF, NMP, pyridine, quinoline, ethanol, isopropanol and dimethoxyethane. Among them, DMA, DMF, NMP, pyridine and quinoline are preferred and DMA or DMF is more preferred.

The compound (I-3) of the present invention prepared as such is able to be isolated and purified by known separating and purifying means such as concentration, concentration in vacuo, extraction with solvent, crystallization, re-precipitation and chromatography.

The compound (I-4) according to the present invention is able to be produced by, for example, the following process.

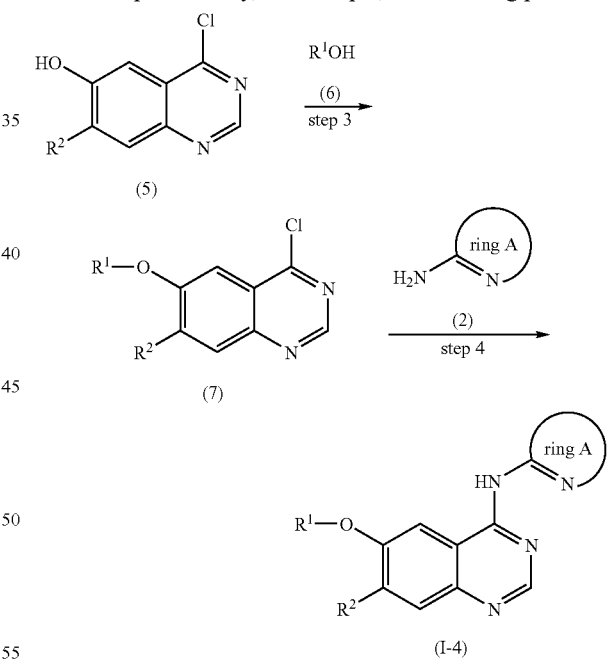

In the formulae, each symbol is the same as that mentioned already.

(Step 3) This step is a reaction where the compound (5) is made to react with the compound (6) to produce the compound (7). This reaction is the so-called Mitsunobu reaction and is able to be carried out, in the presence of a phosphine compound or an azo compound, by the method mentioned in the literature (such as Mitsunobu, O., The use of diethyl azodicarboxylate and triphenylphosphine in synthesis and transformation of natural products, *Synthesis*, vol. 1, 1981, pages 1 to 28), by a method similar thereto or by combination of the above with conventional method.

Amount of the compound (6) used in this step to one equivalent of the compound (5) is usually 0.5 to 10 equivalent(s) and, preferably, 1 to 3 equivalent(s).

Examples of the phosphine compound used in this step are usually triphenylphosphine and tributylphosphine.

Amount of the phosphine compound used therefor to one equivalent of the compound (5) is usually 0.5 to 10 equivalent(s) and, preferably, 1 to 3 equivalent(s).

Examples of the azo compound used are diethylazo dicarboxylate and diisopropylazo dicarboxylate.

Amount of the azo compound used therefor to one equivalent of the compound (5) is usually 0.5 to 10 equivalent(s) and, preferably, 1 to 3 equivalent(s).

Reaction time is usually 1 to 48 hour(s) and, preferably, 4 to 12 hours.

Reaction temperature is usually from 0° C. to refluxing temperature of the reaction solvent and, preferably, 15 to 30° C.

There is no particular limitation for the reaction solvent used in this step so far as it does not affect the reaction and, to be more specific, its examples are THF and toluene.

The compound (7) prepared as such is able to be isolated and purified by known separating and purifying means such as concentration, concentration in vacuo, re-precipitation, extraction with solvent, crystallization and chromatography.

(Step 4) This step is a process for producing the compound (I-4) of the present invention by the reaction of the compound (7) with the aforementioned compound (2).

Reaction conditions such as equivalent numbers of the compounds, reaction temperature and reaction solvent in this step are the same as those in the aforementioned step 1.

The compound (I-4) of the present invention prepared as such is able to be isolated and purified by known separating and purifying means such as concentration, concentration in vacuo, re-precipitation, extraction with solvent, crystallization and chromatography.

The compound (I-5) according to the present invention is also able to be produced by, for example, the following method.

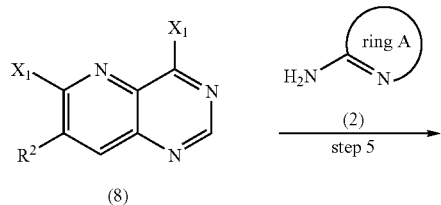

(8)

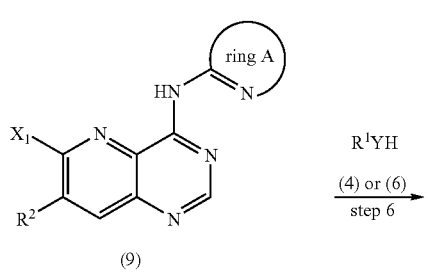

(9)

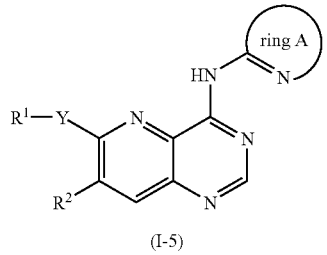

(I-5)

In the formulae, each symbol is the same as that mentioned already.

(Step 5) This step is a process for producing the compound (9) by the reaction of the compound (8) with the aforementioned compound (2).

With regard to $X_1$, it is preferred to be chlorine atom.

Reaction conditions such as equivalent numbers of the compounds, reaction temperature and reaction solvent in this step are the same as those in the aforementioned step 1.

The compound (9) of the present invention prepared as such is able to be subjected to the next step with or without isolation and purification by known separating and purifying means such as concentration, concentration in vacuo, re-precipitation, extraction with solvent, crystallization and chromatography.

(Step 6) This step is a process for producing the compound (I-5) of the present invention by the reaction of the compound (9) with the compound (4) or (6) in the presence of a base.

Amount of the compound (4) or (6) used in this step to one equivalent of the compound (9) is usually 0.2 to 10 equivalent(s) and, preferably, 1 to 3 equivalent(s).

Examples of the base used in this step are a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5,4,0]-undeca-7-ene (DBU) and 1,5-azabicyclo[4,3,0]nona-5-ene (DBN); an aromatic amine such as pyridine, 4-dimethylaminopyridine, picoline, lutidine, quinoline and isoquinoline; an alkali metal such as metal potassium, metal sodium and metal lithium; an alkali metal hydride such as sodium hydride and potassium hydride; alkylated product of alkali metal such as butyl lithium; an alkali metal alkoxide such as potassium tert-butylate, sodium ethylate and sodium methylate; an alkali metal hydroxide such as potassium hydroxide and sodium hydroxide; and alkali metal carbonate such as potassium carbonate, sodium carbonate and cesium carbonate. Among them, tertiary aliphatic amine, alkali metal hydride, alkali metal carbonate and alkali metal alkoxide are preferred and triethylamine, N,N-diisopropylamine, 1,8-diazabicyclo-[5,4,0]undeca-7-ene (DBU), sodium hydride, potassium carbonate and alkali metal alkoxide such as potassium tert-butylate, sodium ethylate or sodium methylate are more preferred.

Amount of the base used in this step to one equivalent of the compound (9) is usually 0.2 to 10 equivalent(s) and, preferably, 1 to 5 equivalent(s).

There is no particular limitation for the reaction solvent used therefor so far as it does not affect the reaction and, for example, an inert solvent is preferred. Specific examples thereof are methylene chloride, chloroform, 1,2-dichloroethane, trichloroethane, DMF, DMA, NMP, acetone, ethanol, isopropanol, tert-butanol, tert-amyl alcohol, ethyl acetate, methyl acetate, acetonitrile, benzene, xylene, toluene, 1,4- dioxane, THF, dimethoxyethane and a mixed solvent thereof. DMF, DMA, NMP, acetonitrile, isopropanol, tert-amyl alcohol are preferred and DMF or DMA is more preferred.

Reaction time is usually 0.2 to 100 hour(s) and, preferably, 1 to 40 hour(s).

Reaction temperature is usually from −20° C. to boiling temperature of the solvent and, preferably, 0° C. to boiling temperature of the solvent.

The compound (I-5) of the present invention prepared as such is able to be isolated and purified by known separating and purifying means such as concentration, concentration in vacuo, re-precipitation, extraction with solvent, crystallization or chromatography.

The substituted quinazoline or pyridopyrimidine derivatives provided by the present invention are able to exist as pharmaceutically acceptable salts and the salts are able to be produced by a common method using the compound for the above-mentioned formula (I-3), (I-4) or (I-5) covered by the compound (I) according to the present invention.

The compound according to the present invention is also able be made into a pharmaceutically acceptable salt or ester by a common method and, reversely, conversion of salt or ester to a free compound is also able to be carried out by a common method.

Examples of an acid addition salt as such are a salt with hydrogen halide such as hydrochloride, hydrofluoride, hydrobromide and hydroiodide; an inorganic acid salt such as nitrate, perchlorate, sulfate, phosphate and carbonate; a lower alkylsulfonate such as methanesulfonate, trifluoromethanesulfonate and ethanesulfonate; an arylsulfonate such as benzenesulfonate and p-toluenesulfonate; an organic acid salt such as fumarate, succinate, citrate, tartrate, oxalate and maleate; and acid addition salt where the acid is an organic acid including an amino acid such as glutamate and asparate.

When the compound of the present invention has an acidic group such as carboxyl group in the group, it is also possible to convert to the corresponding pharmaceutically acceptable salt by treating the compound with a base. Examples of the base addition salt as such are salt with alkali metal such as sodium and potassium; salt with alkali earth metal such as calcium and magnesium; ammonium salt; and salt with an organic base such as guanidine, triethylamine and dicyclohexylamine.

The compound of the present invention may also be present as any hydrate or solvate of the free compound or a salt thereof.

Reversely, it is also possible to convert salt or ester into a free compound by a conventional method.

The compound of the present invention may have tautomer or stereoisomer such as optical isomer, diastereomer and geometrical isomer corresponding to the mode of the substituent. It goes without saying that all of those isomers are covered by the compound according to the present invention. It further goes without saying that any mixture of those isomers is covered by the compound according to the present invention.

When the compound of the present invention is used clinically, pharmaceutically acceptable additives may be added depending upon the dosage form to make into pharmaceutical preparations. As to the additives at that time, various kinds of additives which have been commonly used in the field of pharmaceutical preparations are able to be used and examples thereof are gelatin, lactose, sugar, titanium oxide, starch, crystalline cellulose, hydroxypropyl methyl cellulose, carboxymethyl cellulose, potato starch, microcrystalline wax, white Vaseline, magnesium metasilicate aluminate, anhydrous calcium phosphate, citric acid, trisodium citrate, hydroxypropyl cellulose, sorbitol, sorbitan fatty acid ester, polysolvate, sucrose fatty acid ester, polyoxyethylene, hydrogenated castor oil, polyvinylpyrrolidone, magnesium stearate, light anhydrous silicic acid, talc, vegetable oil, benzyl alcohol, acacia, propylene glycol, polyalkylene glycol, cyclodextrin and hydroxypropyl cyclodextrin.

A mixture of the compound of the present invention and the above-mentioned additive may be used as a solid preparation (such as tablets, capsules, granules, diluted powder and suppository) or a liquid preparation (such as syrup, elixir and injection). Those preparations may be prepared by a common method in the field of pharmaceutical preparations. A liquid preparation may be in such a form of being dissolved or suspended in water or in other appropriate medium. Particularly in the case of injection preparation, it is also possible, if necessary, to dissolve or suspend in a physiological saline solution or in a glucose solution and to add buffer or preservative further. Those preparations are able to contain the compound of the present invention in a rate of 1.0 to 100% by weight or, preferably, 1.0 to 60% by weight.

It is possible to make the compound of the present invention into pharmaceutical preparations according to, for example, the following Preparation Examples.

Preparation Example 1

The compound of Example 1 which will be mentioned later (10 parts), 15 parts of heavy magnesium oxide and 75 parts of lactose were uniformly mixed and made into diluted powder in a form of powder of fine particles of not larger than 350 μm. The diluted powder is placed in a capsule container to prepare a capsule preparation.

Preparation Example 2

The compound of Example 1 which will be mentioned later (45 parts), 15 parts of starch, 16 parts of lactose, 21 parts of crystalline cellulose, 3 parts of polyvinyl alcohol and 30 parts of distilled water were uniformly mixed, disintegrated, granulated, dried and sieved to prepare a granular preparation where diameter is 1410 to 177 μm.

Preparation Example 3

Granular preparation is prepared by the same method as Preparation Example 2, then 3 parts of calcium stearate is added to 96 parts of the granular preparation and the mixture is subjected to a compression molding to prepare tablets where diameter is 10 mm.

Preparation Example 4

To 90 parts of the granular preparation prepared by the method of Preparation Example 2 are added 10 parts of crystalline cellulose and 3 parts of calcium stearate and the mixture is subjected to a compression molding to prepare tablets where diameter is 8 mm. A mixed suspension of syrup-gelatin and precipitated calcium carbonate is added thereto to prepare a sugar-coated tablet preparation.

When the compound of the present invention is used in a clinical field, its dosage and administration frequency vary depending upon sex, age and body weight of a patient, degree of symptom, type/range of aimed treating effect, etc. In the case of oral administration, the dairy dose for an adult is usually about 0.001 to 100 mg/kg, preferably about 0.01 to 50 mg/kg and, more preferably, about 0.1 to 10 mg/kg. There may be some cases where the use of dose within a range exceeding the limitation as such is necessary.

Examples of the appropriate dose by oral administration are at least about 0.01 mg to 2.0 g at the largest in the case of a single administration or plural administrations of two to four times per day. Preferably, the range of the dose is about 1.0 mg to about 200 mg once or twice daily. More preferably, the range of the dose is about 10 mg to 100 mg once daily.

In the case of intravenous administration or oral administration, representative administration range is about 0.001 mg to about 100 mg (preferably, 0.01 mg to about 10 mg) of the compound of the formula (I) per kg of body weight a day. More preferably, it is about 0.1 mg to 10 mg of the compound of the formula (I) per kg of body weight a day.

As mentioned above, the pharmaceutical composition contains the compound of the formula (I) and a pharmaceutically acceptable carrier. The term "composition" includes not only a product prepared by combination, compounding or aggregation of two or more of any component either directly or indirectly, a product prepared by dissociation of one or more component(s) and a product prepared as a result of action of other type or interaction between/among the components but also active and inactive components (pharmaceutically acceptable excipients) constituting the carrier.

A composition containing the compound of the formula (I) in an effective amount for treatment, prevention or retardation of onset of type II diabetes mellitus by a combination with a pharmaceutically acceptable carrier is preferred.

For administration of the effective dose of the compound of the present invention to mammals or, particularly, to humans, any of appropriate administering routes may be used. For example, administration via mouth, rectum, local area, vein, eye, lung, nose, etc. may be carried out. Examples of the dosage form are tablets, troche, diluted powder, suspension, solution, capsule agent, cream and aerosol and tablets for oral use are preferred.

In preparing a composition for oral use, any of common pharmaceutical media may be used and examples thereof are water, glycol, oil, alcohol, perfume additive, preservative and coloring agent. In preparing a liquid composition for oral use, examples thereof are suspension, elixir preparation and solution. Examples of a carrier are starch, sugar, microcrystalline cellulose, diluent, granulating agent, lubricant, binder and disintegrating agent. In preparing a solid composition for oral use, examples thereof are powder, capsule agent and tablets and, among them, a solid composition for oral use is preferred.

In view of easy administration, tablets and capsule agent are the most advantageous oral dosage form. If necessary, tablets may be coated by means of a standard aqueous or non-aqueous art.

In addition to the above-mentioned common dosage form, the compound of the formula (I) may be administered by a sustained release means and/or delivery equipments mentioned, for example, in U.S. Pat. Nos. 3,845,770, 3,916,899, 3,536,809, 3,598,123, 3,630,200 and 4,008,719.

With regard to powder or granules or with regard to a water-soluble liquid, a water-insoluble liquid, an oil-in-water type emulsion or a water-in-oil type emulsion, examples of the pharmaceutical composition of the present invention suitable for oral administration are capsule agent, cachet agent or tablets containing a predetermined amount of active ingredient. Such a composition may be prepared by any method in the field of pharmaceutical science and all methods also include a method where an active ingredient and a carrier comprising one or more necessary component(s) are combined.

Usually, an active ingredient and a liquid carrier or a well-separated solid carrier or both are uniformly and well mixed and then the product is made into an appropriate shape if necessary whereupon a composition is prepared. For example, tablets are prepared by means of compression and molding together, if necessary, with one or more auxiliary component(s). Compressed tablets are prepared by optionally compressing the active ingredient into a shape such as powder or granules using an appropriate machine by mixing, if necessary, with binder, lubricant, inactive excipient, surfactant or dispersing agent.

The molded tablets are prepared by molding a mixture of a powdery wet compound with an inactive liquid diluent using an appropriate machine.

Preferably, each tablet contains about 1 mg to 1 g of an active ingredient and each cachet or capsule preparation contains about 1 mg to 500 mg of an active ingredient.

Examples of pharmaceutical dosage forms for the compound of the formula (I) are as follows.

TABLE 1

Suspension for Injection (I.M.)

|  | mg/ml |
|---|---|
| Compound of the formula (I) | 10 |
| Methyl cellulose | 5.0 |
| Tween 80 | 0.5 |
| Benzyl alcohol | 9.0 |
| Benzalkonium chloride | 1.0 |

Water for injection was added to make 1.0 ml.

TABLE 2

Tablets

|  | mg/tablet |
|---|---|
| Compound of the formula (I) | 25 |
| Methyl cellulose | 415 |
| Tween 80 | 14.0 |
| Benzyl alcohol | 43.5 |
| Magnesium stearate | 2.5 |

TABLE 3

Capsule preparation

|  | mg/capsule |
|---|---|
| Compound of the formula (I) | 25 |
| Lactose powder | 573.5 |
| Magnesium stearate | 1.5 |
| Total: | 600 mg |

TABLE 4

Aerosol

|  | per container |
|---|---|
| Compound of the formula (I) | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I.

When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) other glucokinase activator,
(b) biguanide (such as buformin, metformin and phenformin),
(c) PPAR agonist (such as troglitazone, pioglitazone and rosiglitazone),
(d) insulin,
(e) somatostatin,
(f) α-glucosidase inhibitor (such as voglibose, miglitol and acarbose) and
(g) insulin secretagogues (such as acetohexamide, carbutamide, chlorpropamide, glibomuride, gliclazide, glimepiride, glipizide, gliquidone, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Ordinary physicians, veterinarians or clinical doctors are able to easily decide an effective dose which is necessary for inhibit, suppress or stop the progress of the symptoms.

EXAMPLES

The present invention will now be more specifically illustrated by listing Examples as hereunder although the present invention is never limited by those Examples.

In a silica gel column chromatography in Examples, Wakogel (registered trade mark) C-300 manufactured by Wako Pure Chemicals or KP-Sil (registered trade mark) Silica Prepacked Column manufactured by Biotarge was used. For a preparatory thin layer chromatography, Kieselgel™ 60F$_{254}$, Art. 5744 manufactured by Merck was used. For a basic silica gel column chromatography, Chromatorex (registered trade mark) NH (100 to 250 mesh or 200 to 350 mesh) manufactured by Fuji Silicia Kagaku was used.

Mass spectrum was measured by an electrospray ionization method (ESI) or an atmospheric chemical ionization method (APCI) using Micromass ZQ manufactured by Waters.

With regard to NMR spectrum, measurement was conducted using a spectrometer of a type of Gemini-200 (200 MHz; Varian), Gemini-300 (300 MHz; Varian), Mercury 400 (400 MHz; Varian) or Inova 400 (400 MHz; Varian) where dimethyl sulfoxide was used as an internal standard in case the measurement was done in a heavy dimethyl sulfoxide solution and all δ values were shown in terms of ppm.

Meanings of the abbreviations mentioned in the following Examples will be shown as hereunder.

i-Bu: isobutyl group
n-Bu: n-butyl group
t-Bu: tert-butyl group
Me: methyl group
Et: ethyl group
Ph: phenyl group
i-Pr: isopropyl group
n-Pr: n-propyl group
CDCl$_3$: heavy chloroform
CD$_3$OD: heavy methanol
DMSO-d6: heavy dimethyl sulfoxide Meanings of the abbreviations in nuclear magnetic resonance spectrum are shown as hereunder.

s: singlet
d: doublet
dd: double doublet
t: triplet
m: multiplet
br: broad
q: quartet
J: coupling constant
Hz: Herz Example 1

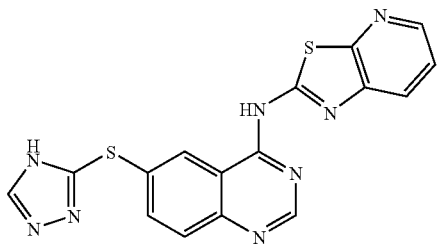

[6-(4H-[1,2,4]Triazol-3-ylsulfanyl)-quinazolin-4-yl]-thiazolo[5,4-b]pyridin-2-yl-amine 4-Chloro-6-iodo-quinazoline (1.00 g; 3.44 mmol) and 0.70 g (4.64 mmol) of thiazolo[5,4-b]pyridin-2-yl-amine were heated at 135° C. for 4 hours with stirring in 10 ml of phenol. Chloroform was added to the reaction solution followed by washing with a 1 N aqueous solution of sodium hydroxide. The organic layer was dried and concentrated and the resulting residue was purified by a silica gel column chromatography (chloroform:methanol=50:1) to give 486 mg (yield: 35%) of (6-iodo-qunazolin-4-yl)-thiazolo[5,4-b]pyridin-2-yl-amine as a yellow solid.

To a solution of 80 mg (0.197 mmol) of the resulting iodine compound in 2 ml of N,N-dimethylacetamide were added 38 mg (0.197 mmol) of copper iodide, 128 mg (0.394 mmol) of cesium carbonate and 30 mg (0.295 mmol) of 3-mercapto-1, 2,4-triazole followed by stirring at 140° C. for 5 hours. Water was added to the reaction solution followed by extracting with chloroform. The organic layer was dried and concentrated and the resulting residue was purified by a thin layer silica gel chromatography (chloroform:methanol=8:1) to give 15 mg (yield: 20%) of the title compound as a yellow solid.

$^1$HNMR (CDCl$_3$) δ: 7.43-7.46 (1H, m), 7.82 (1H, d, J=8.8Hz), 7.90 (1H, d, J=8.8Hz), 8.05 (1H, d, J=8.0Hz), 8.18 (1H, s), 8.31 (1H, s), 8.43 (1H, d, J=3.6Hz), 8.69 (1H, s)

ESI-MS (m/e): 379 [M+H]$^+$

Compounds of Examples 2 to 21 were prepared by the same method as in the above Example 1. Hereinafter, analytical data of those compounds are shown.

Example 2

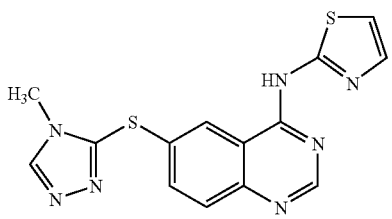

[6-(4-Methyl-4H-[1,2,4]triazol-3-ylsulfanyl)-quinazolin-4-yl]-thiazol-2-yl-amine The compound of Example 2 was manufactured by the same method as in Example 1, by a similar method thereto or by a combination of such a method with a conventional method using 4-chloro-6-iodo-quinazoline, 2-amino-thiazole and 3-mercapto-4-methyl-1,2,4-triazole.

$^1$HNMR (CDCl$_3$) δ: 3.66 (3H, s), 7.02 (1H, d, J=3.6Hz), 7.51 (1H, d, J=3.6Hz), 7.60-7.80 (2H, m), 8.00-8.35 (2H, m), 8.49 (1H, brs)

ESI-MS (m/e): 342 [M+H]$^+$

Example 3

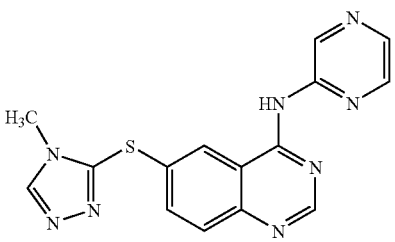

[6-(4-Methyl-4H-[1,2,4]triazol-3-ylsulfanyl)-quinazolin-4-yl]-pyrazin-2-yl-amine The compound of Example 3 was manufactured by the same method as in Example 1, by a similar method thereto or by a combination of such a method with a conventional method using 4-chloro-6-iodo-quinazoline, 2-amino-pyrazine and 3-mercapto-4-methyl-1,2,4-triazole.

$^1$HNMR (CDCl$_3$) δ: 3.68 (3Hx2/3, s), 3.70 (3Hx1/3, s), 7.38-7.70 (2Hx2/3, m), 7.77-7.98 (2Hx1/3, m), 8.03-8.62 (4H, m), 8.62 (1Hx2/3, brs), 8.70 (1Hx2/3, brs), 8.99 (1Hx1/3, brs), 10.00 (1Hx1/3, brs)

ESI-MS (m/e): 337 [M+H]$^+$

Example 4

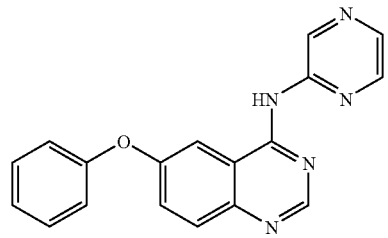

(6-Phenoxyquinazolin-4-yl)-pyrazin-2-yl-amine

The compound of Example 4 was manufactured by the same method as in Example 1, by a similar method thereto or by a combination of such a method with a conventional method using 4-chloro-6-iodo-quinazoline, 2-amino-pyrazine and phenol.

$^1$HNMR (CDCl$_3$) δ: 7.06-7.20 (2H, m), 7.35-7.52 (3H, m), 7.60-8.30 (5H, m), 8.37 (1Hx1/2, brs), 8.62 (1Hx1/2, brs), 8.89 (1Hx1/2, brs), 10.07 (1Hx1/2, brs)

ESI-MS (m/e): 316 [M+H]$^+$

Example 5

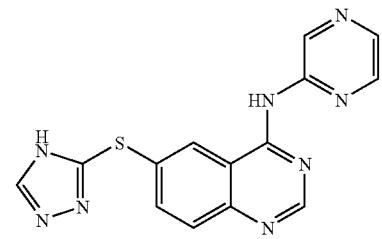

[6-(4H-[1,2,4]Triazol-3-ylsulfanyl)-quinazolin-4-yl]-pyrazin-2-yl-amine

The compound of Example 5 was manufactured by the same method as in Example 1, by a similar method thereto or by a combination of such a method with a conventional method using 4-chloro-6-iodo-quinazoline, 2-amino-pyrazine and 3-mercapto-1,2,4-triazole.

$^1$HNMR (CDCl$_3$) δ: 7.85-7.98 (2H, m), 8.04-8.60 (4H, m), 8.63 (1Hx1/3, brs), 8.74 (1Hx1/3, brs), 8.85 (1Hx2/3, brs), 9.95 (1Hx2/3, brs)

ESI-MS (m/e): 323 [M+H]$^+$

Example 6

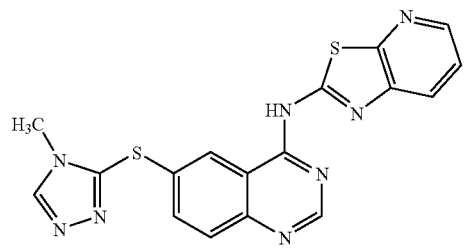

[6-(4-Methyl-4H-[1,2,4]triazol-3-ylsulfanyl)-quinazolin-4-yl]-thiazolo[5,4-b]pyridin-2-yl-amine The compound of Example 6 was manufactured by the same method as in Example 1, by a similar method thereto or by a combination of such a method with a conventional method using 4-chloro-6-iodo-quinazoline, thiazolo[5,4-b]pyridin-2-yl-amine and 3-mercapto-4-methyl-1,2,4-triazole.

$^1$HNMR (CDCl$_3$) δ: 3.72 (3H, s), 7.38 (1H, dd, J=8.0, 4.4 Hz), 7.70-7.83 (3H, m), 7.98 (1H, d, J=8.0Hz), 8.35 (1H, s), 8.45 (1H, dd, J=4.4, 1.6Hz), 8.57 (1H, s)

ESI-MS (m/e): 393 [M+H]$^+$

Example 7

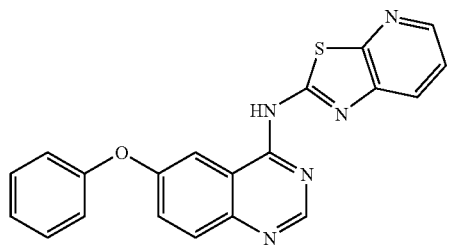

(6-Phenoxy-quinazolin-4-yl)-thiazolo[5,4-b]pyridin-2-yl-amine

The compound of Example 7 was manufactured by the same method as in Example 1, by a similar method thereto or by a combination of such a method with a conventional method using 4-chloro-6-iodo-quinazoline, thiazolo[5,4-b]pyridin-2-yl-amine and phenol.

$^1$HNMR (CDCl$_3$) δ: 7.07-7.27 (3H, m), 7.32-7.58 (4H, m), 7.77 (1H, d, J=8.7Hz), 7.99 (1H, dd, J=8.1, 1.5Hz), 8.13 (1H, d, J=3.0Hz), 8.23 (1H, s), 8.44 (1H, dd, J=4.7, 1.5Hz)

ESI-MS (m/e): 372 [M+H]$^+$

Example 8

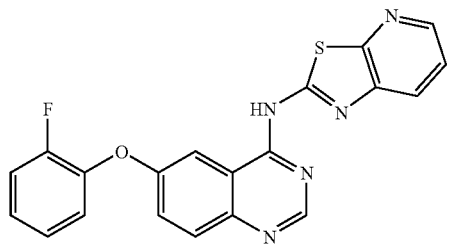

[6-(2-Fluoro-phenoxy)-quinazolin-4-yl]-thiazolo[5,4-b]pyridin-2-yl-amine

The compound of Example 8 was manufactured by the same method as in Example 1, by a similar method thereto or by a combination of such a method with a conventional method using 4-chloro-6-iodo-quinazoline, thiazolo[5,4-b]pyridin-2-yl-amine and 2-fluorophenol.

$^1$HNMR (CDCl$_3$) δ: 7.19-7.77 (6H, m), 7.77 (1H, d, J=9.0Hz), 7.99 (1H, br-d, J=7.5Hz), 8.04 (1H, m), 8.22 (1H, s), 8.45 (1H, m)

ESI-MS (m/e): 390 [M+H]$^+$

Example 9

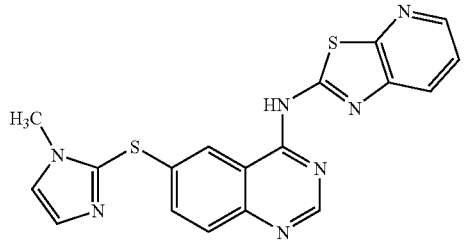

[6-(1-Methyl-1H-imidazol-2-ylsulfanyl)-quinazolin-4-yl]-thiazolo[5,4-b]pyridin-2-yl-amine The compound of Example 9 was manufactured by the same method as in Example 1, by a similar method thereto or by a combination of such a method with a conventional method using 4-chloro-6-iodo-quinazoline, thiazolo[5,4-b]pyridin-2-yl-amine and 2-mercapto-1-methyl-imidazole.

$^1$HNMR (CDCl$_3$) δ: 3.74 (3H, s), 7.15 (1H, brs), 7.41 (1H, brs), 7.41 (1H, dd, J=8.1, 4.8Hz), 7.43-8.00 (3H, m), 8.03 (1H, dd, J=8.1, 1.5Hz), 8.40-8.52 (2H, m)

ESI-MS (m/e): 392 [M+H]$^+$

Example 10

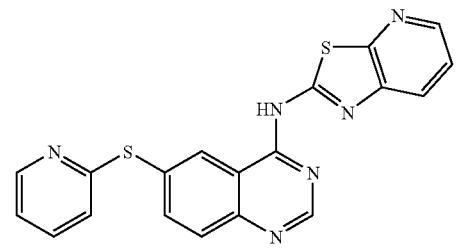

[6-(Pyridin-2-ylsulfanyl)-quinazolin-4-yl]-thiazolo-[5,4-b]pyridin-2-yl-amine

The compound of Example 10 was manufactured by the same method as in Example 1, by a similar method thereto or by a combination of such a method with a conventional method using 4-chloro-6-iodo-quinazoline, thiazolo[5,4-b]pyridin-2-yl-amine and 2-mercaptopyridine.

$^1$ HNMR (CDCl$_3$) δ: 7.04-7.16 (2H, m), 7.39 (1H, dd, J=8.1, 4.8Hz), 7.64 (1H, m), 7.78 (1H, br-d, J=8.7), 7.90-8.04 (2H, m), 8.29 (1H, brs), 8.41-8.52 (2H, m), 8.33 (1H, brs)

ESI-MS (m/e): 389 [M+H]$^+$

Example 11

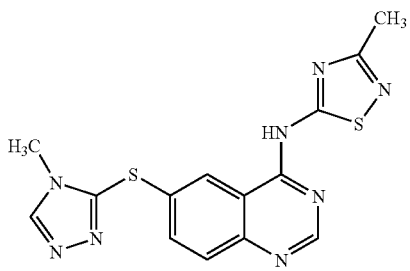

[6-(4-Methyl-4H-[1,2,4]triazol-4-ylsulfanyl)-quinazolin-4-yl]-(3-methyl-[1,2,4]thiadiazol-5-yl-amine The compound of Example 11 was manufactured by the same method as in Example 1, by a similar method thereto or by a combination of such a method with a conventional method using 4-chloro-6-iodo-quinazoline, 5-amino-2-methyl-1,2,4-thiadiazole and 3-mercapto-4-methyl-1,2,4-triazole.

$^1$HNMR (CDCl$_3$) δ2.59 (3H, s), 3.73 (3H, s), 7.87 (1H, d, J=8.8Hz), 7.95 (1H, d, J=8.8Hz), 8.37 (1H, s), 8.55 (1H, s), 8.97 (1H, s)

ESI-MS (m/e): 357 [M+H]$^+$

Example 12

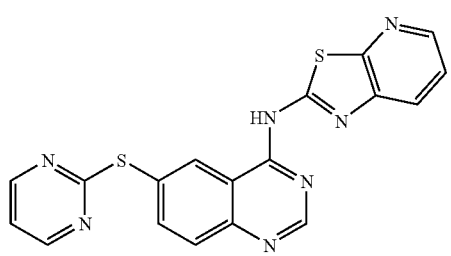

[6-(Pyrimidin-2-ylsulfanyl)-quinazoli-4-yl]-thiazolo[5,4-b]-pyridin-2-yl-amine

The compound of Example 12 was manufactured by the same method as in Example 1, by a similar method thereto or by a combination of such a method with a conventional method using 4-chloro-6-iodo-quinazoline, thiazolo[5,4-b]pyridin-2-yl-amine and 2-mercaptopyrimidine.

$^1$HNMR (CDCl$_3$) δ: 7.07 (1H, t, J=4.8), 7.39 (1H, dd, J=8.1, 4.8Hz), 7.80-8.12 (3H, m), 8.40-8.60 (4H, m), 8.78 (1H, m)

ESI-MS (m/e): 390 [M+H]$^+$

Example 13

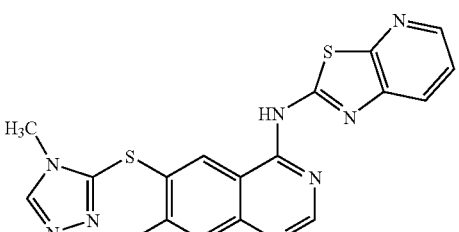

[6-(4-Methyl-4H-[1,2,4]triazol-3-ylsulfanyl)-quinazolin-4-yl]-thiazolo[5,4-b]-pyridin-2-yl-amine The compound of Example 13 was manufactured by the same method as in Example 1, by a similar method thereto or by a combination of such a method with a conventional method using 4-chloro-7-fluoro-6-iodo-quinazoline, thiazolo[5,4-b]-pyridin-2-yl-amine and 3-mercapto-4-methyl-1,2,4-triazole.

$^1$HNMR (CDCl$_3$) δ: 3.82 (3H, s), 7.41 (1H, dd, J=8.1, 4.8Hz), 7.59 (1H, br-d, J=11.1Hz), 7.98 (1H, br-d, J=8.1Hz), 8.37 (1H, s), 8.46 (1H, br-d, J=4.8Hz), 8.60-8.90 (2H, m)

ESI-MS (m/e): 411 [M+H]$^+$

Example 14

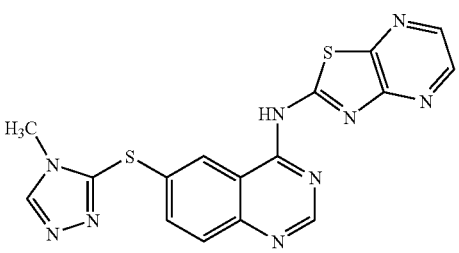

[6-(4-Methyl-4H-[1,2,4]triazol-3-ylsulfanyl)-quinazolin-4-yl]-thiazolo[4,5-b]-pyrazin-2-yl-amine The compound of Example 14 was manufactured by the same method as in Example 1, by a similar method thereto or by a combination of such a method with a conventional method using 4-chloro-6-iodo-quinazoline, thiazolo[5,4-b]-pyrazin-2-yl-amine and 3-mercapto-4-methyl-1,2,4-triazole.

$^1$HNMR (CDCl$_3$) δ: 3.72 (3H, s), 7.74-7.81 (2H, m), 8.26 (1H, d, J=2.8Hz), 8.37 (1H, d, J=2.8Hz), 8.49 (1H, s), 8.62 (1H, d, J=1.6Hz), 8.77 (1H, s)

ESI-MS (m/e): 394 [M+H]$^+$

Example 15

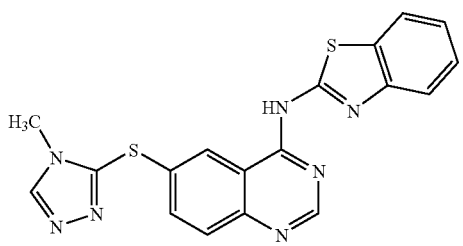

Benzothiazol-2-yl-[6-(4-methyl-4H-[1,2,4]-triazol-3-yl-sulfanyl)-quinazolin-4-yl]-amine The compound of Example 15 was manufactured by the same method as in Example 1, by a similar method thereto or by a combination of such a method with a conventional method using 4-chloro-6-iodo-quinazoline, 2-amino-benzothiazole and 3-mercapto-4-methyl-1,2,4-triazole.

$^1$HNMR (CDCl$_3$) δ3.68 (3H, s), 7.32 (1H, m), 7.45 (1H, m), 7.67-7.72 (2H, m), 7.79-7.81 (2H, m), 8.31-8.34 (2H, m) 8.60 (1H, s)

ESI-MS (m/e): 392 [M+H]$^+$

Example 16

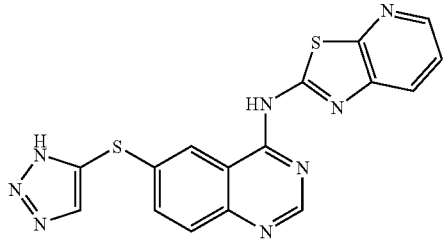

[6-(3H-[1,2,3]Triazol-4-ylsulfanyl)-quinazolin-4-yl]-thiazolo[5,4-b]pyridin-2-yl-amine The compound of Example 16 was manufactured by the same method as in Example 1, by a similar method thereto or by a combination of such a method with a conventional method using 4-chloro-6-iodo-quinazoline, thiazolo[5,4-b]pyridin-2-yl-amine and 3H-[1,2,3]triazole-4-thiol.

$^1$HNMR (CDCl$_3$) δ: 7.43 (1H, dd, J=8.1, 4.8Hz), 7.65-7.86 (2H, m), 7.88 (1H, s), 8.03 (1H, dd, J=8.1, 1.5Hz), 8.39-8.60 (3H, m)

ESI-MS (m/e): 379 [M+H]$^+$

Example 17

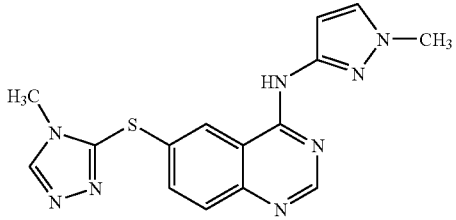

(1-Methyl-1H-pyrazol-3-yl)-[6-4-methyl-4H-[1,2,4]-triazol-3-ylsulfanyl)-quinazolin-4-yl]-amine The compound of Example 17 was manufactured by the same method as in Example 1, by a similar method thereto or by a combination of such a method with a conventional method using 4-chloro-6-iodo-quinazoline, 3-amino-1-methyl-1H-[1,2]-pyrazole and 3-mercapto-4-methyl-1,2,4-triazole.

$^1$HNMR (CDCl$_3$) δ3.74 (3H, s), 3.91 (3H, s), 6.88 (1H, d, J=2.4Hz), 7.42 (1H, d, J=2.4Hz), 7.89 (1H, dd, J=2.0, 8.4Hz), 8.03 (1H, d, J=8.4Hz), 8.36 (1H, s), 8.56 (1H, d, J=2.0Hz), 8.78 (1H, s)

ESI-MS (m/e): 339 [M+H]$^+$

Example 18

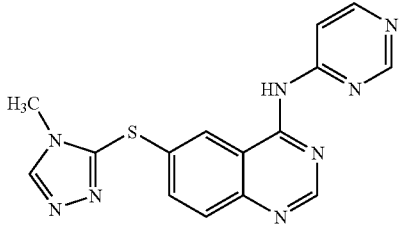

[6-(4-Methyl-4H-[1,2,4]-triazol-3-ylsulfanyl)-quinazolin-4-yl]-pyrimidin-4-yl-amine The compound of Example 18 was manufactured by the same method as in Example 1, by a similar method thereto or by a combination of such a method with a conventional method using 4-chloro-6-iodo-quinazoline, 4-aminopyrimidine and 3-mercapto-4-methyl-1,2,4-triazole.

$^1$HNMR (CDCl$_3$) δ: 3.82 (3H, s), 7.45 (1H, m), 7.59-7.63 (2H, m), 7.95 (1H, dd, J=8.8, 1.6Hz), 7.69 (1H, d, J=8.0Hz), 7.92 (1H, brs), 8.07 (1H, d, J=8.8Hz), 8.45 (1H, s), 8.50 (1H, d, J=1.6Hz), 8.87 (1H, s)

ESI-MS (m/e): 336 [M+H]$^+$

Example 19

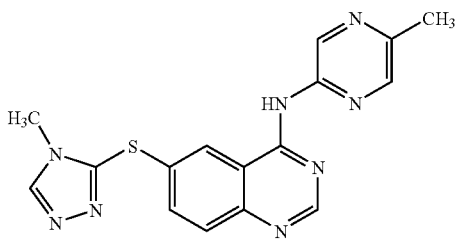

(5-Methyl-pyrazin-2-yl)-[6-(4-methyl-4H-[1,2,4]-triazol-3-ylsulfanyl)-quinazolin-4-yl]-amine The compound of Example 19 was manufactured by the same method as in Example 1, by a similar method thereto or by a combination of such a method with a conventional method using 4-chloro-6-iodo-quinazoline, 2-amino-5-methylpyrazine and 3-mercapto-4-methyl-1,2,4-triazole.

$^1$HNMR (CD$_3$OD) δ: 2.61 (3H, s), 3.78 (3H, s), 7.87 (1H, d, J=8.8Hz), 7.95 (1H, dd, J=8.8, 2.0Hz), 8.44 (1H, brs), 8.70 (1H, s), 8.74 (1H, d, J=2.0Hz), 8.83 (1H, s), 9.35 (1H, s)

ESI-MS (m/e): 351 [M+H]$^+$

Example 20

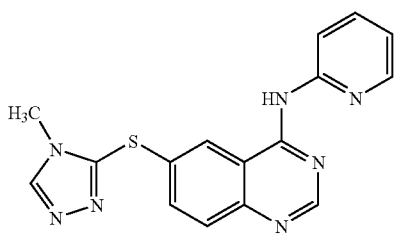

[6-(4-Methyl-4H-[1,2,4]triazol-3-ylsulfanyl)-quinazolin-4-yl]-pyridin-2-yl-amine The compound of Example 20 was manufactured by the same method as in Example 1, by a similar method thereto or by a combination of such a method with a conventional method using 4-chloro-6-iodo-quinazoline, 2-aminopyridine and 3-mercapto-4-methyl-1,2,4-triazole.

$^1$HNMR (CDCl$_3$) δ3.76 (3H, s), 7.33 (1H, m), 7.85-7.95 (2H, m), 8.12 (1H, m), 8.26-8.37 (2H, m), 8.42 (1H, s), 8.63 (1H, s), 8.83 (1H, s)

ESI-MS (m/e): 336 [M+H]$^+$

Example 21

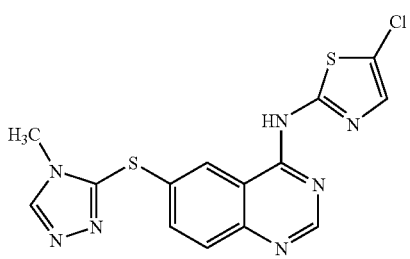

(5-Chloro-thiazol-2-yl)-[6-(4-methyl-4H-[1,2,4]-triazol-3-ylsulfanyl)-quinazolin-4-yl]-amine The compound of Example 21 was manufactured by the same method as in Example 1, by a similar method thereto or by a combination of such a method with a conventional method using 4-chloro-6-iodo-quinazoline, 2-amino-5-chlorothiazole and 3-mercapto-4-methyl-1,2,4-triazole.

$^1$HNMR (CD$_3$OD) δ: 3.72 (3H, s), 7.35 (1H, s), 7.70-7.78 (2H, m), 8.48 (1H, s), 8.53 (1H, d, J=1.6Hz), 8.68 (1H, s)

ESI-MS (m/e): 376 [M+H]$^+$

Example 22

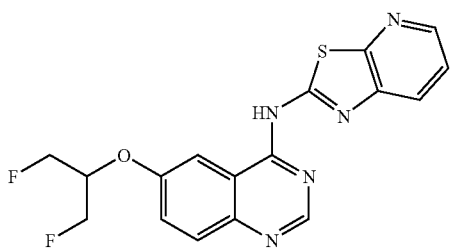

[6-(2-Fluoro-1-fluoromethyl-ethoxy)-quinazolin-4-yl]-thiazolo[5,4-b]pyridin-2-yl-amine 4-Chloro-6-hydroxy-quinazoline (500 mg; 2.78 mmol), 800 mg (8.33 mmol) of 1,3-difluoro-2-propanol and 2.18 g (8.33 mmol) of triphenyl phosphine were dissolved in 30 ml of THF and 3.62 g (8.33 mmol) was added thereto at room temperature. The reaction solution was stirred at room temperature for 3 hours more, a saturated aqueous solution of sodium hydrogen carbonate was added and the mixture was extracted with chloroform. The organic layer was dried and concentrated and the resulting residue was purified by a silica gel column chromatography (hexane:ethyl acetate=1:2) to give 530 mg (yield: 74%) of 4-chloro-6-(2-fluoro-1-fluoromethyl-ethoxy)-quinazoline as a yellow solid.

The resulting chloro compound (38 mg; 0.147 mmol) and 22 mg (0.147 mmolo) of thiazolo[5,4-b]pyridin-2-yl-amine were heated at 140° C. for 2 hours with stirring in 0.2 ml of phenol. Chloroform was added to the reaction solution and the mixture was washed with 1N aqueous solution of sodium hydroxide. The organic layer was dried and concentrated and the resulting residue was purified by a thin layer silica gel chromatography (chloroform:methanol=10:1) to give 15 mg (yield: 27%) of the title compound as a yellow solid.

$^1$HNMR (CDCl$_3$) δ: 4.70-4.73 (2H, m), 4.84-4.86 (2H, m), 4.90-5.02 (2H, m), 7.36 (1H, dd, J=8.0, 4.4Hz), 7.49 (1H, dd, J=8.8, 2.8Hz), 7.74 (1H, d, J=8.8Hz), 7.98 (1H, dd, J=8.0, 1.6Hz), 8.04 (1H, d, J=2.8Hz), 8.22 (1H, s), 8.45 (1H, dd, J=4.4, 1.2Hz)

ESI-MS (m/e): 374 [M+H]$^+$

Example 23

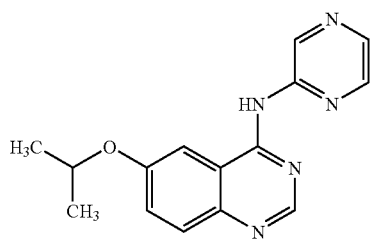

(6-Isopropoxy-quinazolin-4-yl)-pyrazin-2-yl-amine

The compound of Example 23 was manufactured by the same method as in Example 22, by a similar method thereto or by a combination of such a method with a conventional method using 4-chloro-6-hydroxy-quinazoline, 2-propanol and 2-aminopyrazine.

$^1$HNMR (CDCl$_3$) δ: 1.43 (6H, d, J=6.0Hz), 4.70-4.90 (1H, m), 7.19-7.68 (2H, m), 7.89-8.08 (1Hx3/2, m), 8.18-8.40 (2H, m), 8.71 (1Hx1/2, brs), 8.83 (1Hx1/2, brs), 10.10 (1Hx1/2, brs)

ESI-MS (m/e): 282 [M+H]$^+$

Example 25

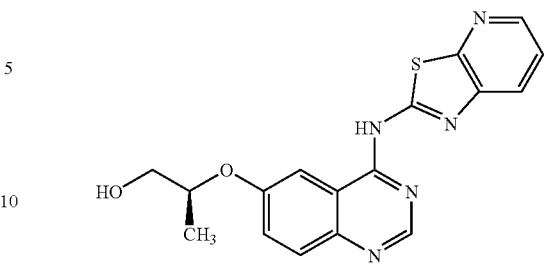

[6-(2-Hydroxy-(1S)-methyl-ethoxy-quinazolin-4-yl]-thiazolo[5,4-b]pyridin-2-yl-amine The compound of Example 25 was manufactured by the same method as in Example 22, by a similar method thereto or by a combination of such a method with a conventional method using 4-chloro-6-hydroxy-quinazoline, (2S)-1-(tert-butyldimethyl-silyloxy)-2-propanol and thiazolo[5,4-b]pyridin-2-yl-amine.

$^1$HNMR (DMSO) δ: 1.35 (3H, d, J=6.0Hz), 3.61-3.67 (2H, m), 4.75 (1H, m), 7.61 (1H, dd, J=8.0, 4.8Hz), 7.76 (1H, dd, J=8.8, 2.4Hz), 8.04 (1H, d, J=8.8Hz), 8.14 (1H, dd, J=8.0, 1.6Hz), 8.19 (1H, d, J=2.4Hz), 8.58 (1H, dd, J=4.8, 1.6Hz), 9.27 (1H, s)

ESI-MS (m/e): 354 [M+H]$^+$

Example 24

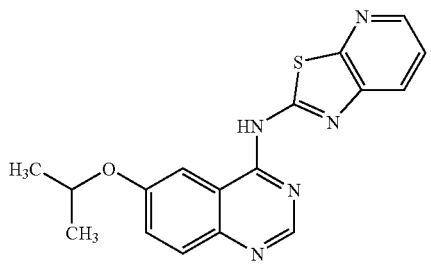

(6-Isopropoxy-quinazolin-4-yl)-thiazolo[5,4-b]pyridin-2-yl-amine

The compound of Example 24 was manufactured by the same method as in Example 22, by a similar method thereto or by a combination of such a method with a conventional method using 4-chloro-6-hydroxy-quinazoline, 2-propanol and thiazolo[5,4-b]pyridin-2-yl-amine.

$^1$HNMR (CDCl$_3$) δ: 1.43 (6H, d, J=6.0Hz), 4.85 (1H, brs), 7.34 (1H, dd, J=8.4, 4.0Hz), 7.38 (1H, d, J=8.0Hz), 7.71 (1H, brs), 7.90 (1H, brs), 7.95 (1H, dd, J=8.0, 1.2Hz), 8.20 (1H, brs), 8.43 (1H, d, J=4.0Hz)

ESI-MS (m/e): 338 [M+H]$^+$

Example 26

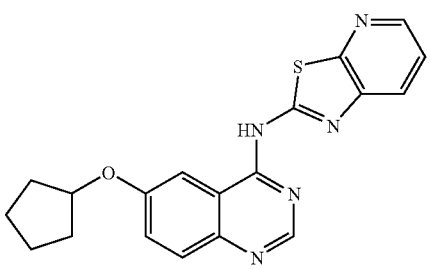

(6-Cyclopentyloxy-quinazolin-4-yl)-thiazolo[5,4-b]-pyridin-2-yl-amine

The compound of Example 26 was manufactured by the same method as in Example 22, by a similar method thereto or by a combination of such a method with a conventional method using 4-chloro-6-hydroxy-quinazoline, cyclopentanol and thiazolo[5,4-b]pyridin-2-yl-amine.

$^1$HNMR (CDCl$_3$) δ: 1.69-2.05 (8H, m), 5.00 (1H, m), 7.34 (1H, dd, J=8.0, 6.4Hz), 7.37 (1H, brs), 7.69 (1H, d, J=8.0Hz), 7.92 (1H, brs), 7.94 (1H, d, J=8.0Hz), 8.17 (1H, brs), 8.43 (1H, brs)

ESI-MS (m/e): 364 [M+H]$^+$

Example 27

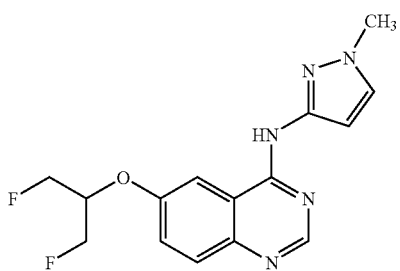

[6-(2-Fluoro-1-fluoromethyl-ethoxy)-quinazolin-4-yl]-(1-methyl-1H-pyrazol-3-yl)-amine The compound of Example 27 was manufactured by the same method as in Example 22, by a similar method thereto or by a combination of such a method with a conventional method using 4-chloro-6-hydroxy-quinazoline, 1,3-difluoro-2-propanol and 3-amino-1-methyl-1H-[1,2]pyrazole.

$^1$HNMR (CDCl$_3$) δ: 3.86 (3H, s), 4.60-4.70 (2H, m), 4.74-4.85 (2H, m), 4.90 (1H, m), 7.00 (1H, d, J=2.4Hz), 7.38 (1H, d, J=2.4Hz), 7.49 (1H, dd, J=8.8, 2.4Hz), 7.61 (1H, d, J=2.4Hz), 7.83 (1H, d, J=8.8Hz), 8.66 (1H, s)

ESI-MS (m/e): 307 [M+H]$^+$

Example 28

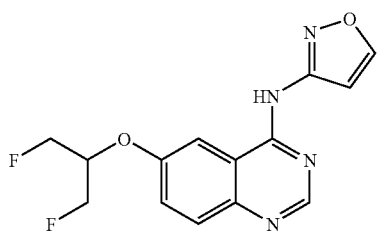

[6-(2-Fluoro-1-fluoromethyl-ethoxy)-quinazolin-4-yl]-isoxazol-3-yl-amine

The compound of Example 28 was manufactured by the same method as in Example 22, by a similar method thereto or by a combination of such a method with a conventional method using 4-chloro-6-hydroxy-quinazoline, 1,3-difluoro-2-propanol and 3-aminoisoxazole.

$^1$HNMR (CD$_3$OD) δ: 4.72-4.84 (2H, m), 4.85-4.88 (2H, m), 5.05 (1H, m), 7.35 (1H, s), 7.58 (1H, d, J=8.8Hz), 7.85 (1H, d, J=8.8Hz), 7.94 (1H, s), 8.45 (1H, s), 8.69 (1H, s)

ESI-MS (m/e): 307 [M+H]$^+$

Example 29

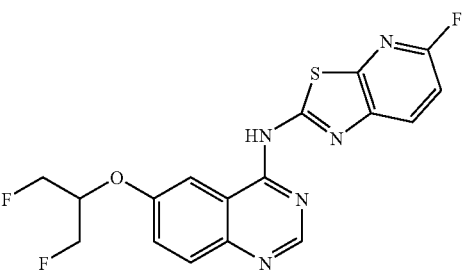

[6-(2-Fluoro-1-fluoromethyl-ethoxy)-quinazolin-4-yl]-(5-fluoro-thiazolo[5,4-b]pyridin-2-yl)-amine The compound of Example 29 was manufactured by the same method as in Example 22, by a similar method thereto or by a combination of such a method with a conventional method using 4-chloro-6-hydroxy-quinazoline, 1,3-difluoro-2-propanol and 5-fluoro-thiazolo[5,4-b]pyridin-2-yl-amine.

$^1$HNMR (CD$_3$OD) δ: 4.71-4.73 (2H, m), 4.83-4.85 (2H, m), 5.00 (1H, m), 7.00 (1H, dd, J=8.8, 1.6Hz), 7.47 (1H, dd, J=8.8, 2.8Hz), 7.73 (1H, d, J=8.8Hz), 8.01 (1H, d, J=2.8Hz), 8.04 (1H, dd, J=8.8, 1.6Hz), 8.20 (1H, s)

ESI-MS (m/e): 392 [M+H]$^+$

Example 30

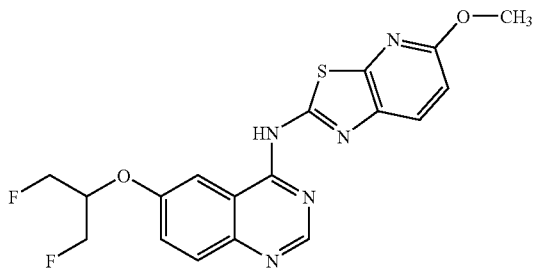

[6-(2-Fluoro-1-fluoromethyl-ethoxy)-quinazolin-4-yl]-(5-methoxy-thiazolo[5,4-b]pyridin-2-yl)-amine The compound of Example 30 was manufactured by the same method as in Example 22, by a similar method thereto or by a combination of such a method with a conventional method using 4-chloro-6-hydroxy-quinazoline, 1,3-difluoro-2-propanol and 5-methoxy-thiazolo[5,4-b]pyridin-2-yl-amine.

$^1$HNMR (CD$_3$OD) δ: 4.04 (3H, s), 4.70-4.75 (2H, m), 4.80-4.86 (2H, m), 5.08 (1H, m), 6.94 (1H, d, J=8.4Hz), 7.70 (1H, d, J=8.4Hz), 7.78-7.91 (2H, m), 8.12 (1H, d, J=2.8Hz), 8.80 (1H, s)

ESI-MS (m/e): 404 [M+H]$^+$

Example 31

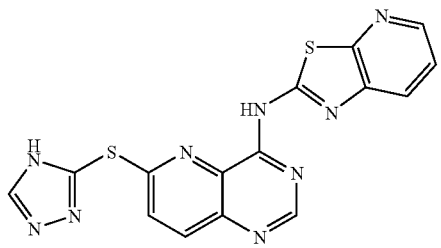

[6-(4H-[1,2,4]Triazol-3-ylsulfanyl)-pyrido[3,2-d]-pyrimidin-4-yl]-thiazolo[5,4-b]pyridin-2-yl)-amine 4,6-Dichloro-pyrido[3,2-d]pyrimidine (100 mg; 0.503 mmol) and 76 mg (0.503 mmol) of thiazolo[5,4-b]pyridin-2-yl-amine in 0.3 mol of phenol were heated at 140° C. for 2 hours with stirring. Ethyl acetate was added to the reaction solution and the resulting solid was purified by a thin layer silica gel column chromatography (chloroform:methanol=10:1) to give 78 mg (yield: 45%) of (6-chloro-pyrido[3,2-d]pyrimidin-4-yl)-thiazolo[5,4-b]pyridin-2-yl-amine as a yellow solid.

DBU (18 mg; 0.120 mmol) and 12 mg (0.120 mmol) of 3-mercapto-1,2,4-triazole were added to a solution of 25 mg (0.080 mmol) of the resulting chloro compound in 1 ml of N,N-dimethylacetamide and the mixture was stirred at 140° C. for 3 hours. The reaction solution was concentrated in vacuo and the resulting residue was purified by a reversed phase preparative HPLC (0.1% TFA-containing water: acetonitrile=90:10→10:90) to give 4 mg (yield: 13%) of the title compound as a yellow solid.

$^1$HNMR (CD$_3$OD) δ: 7.70 (1H, dd, J=8.0, 4.8Hz), 7.81 (1H, d, J=8.4Hz), 8.26 (1H, d, J=8.4Hz), 8.35 (1H, dd, J=8.0, 1.6Hz), 8.61-8.63 (2H, m), 9.07 (1H, s)

ESI-MS (m/e): 380 [M+H]$^+$

Example 32

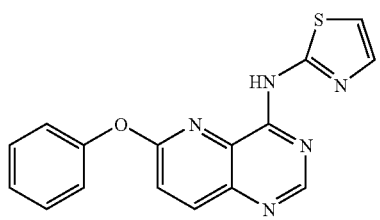

(6-Phenoxy-pyrido[3,2-d]pyrimidin-4-yl)-thiazol-2-yl-amine

The compound of Example 32 was manufactured by the same method as in Example 31, by a similar method thereto or by a combination of such a method with a conventional method using 4,6-dichloro-pyrido[3,2-d]pyrimidine, 2-aminothiazole and phenol.

$^1$HNMR (CDCl$_3$) δ: 7.04 (1H, d, J=3.6Hz), 7.23 (2H, d, J=8.4Hz), 7.33 (1H, t, J=7.2Hz), 7.48-7.52 (3H, m), 8.24 (1H, d, J=8.8Hz), 8.88 (1H, s), 9.53 (1H, s)

ESI-MS (m/e): 322 [M+H]$^+$

Example 33

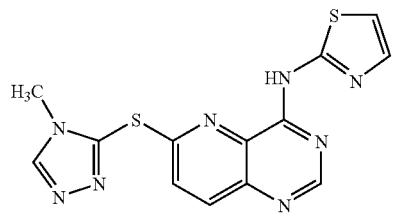

[6-(4-Methyl-4H-[1,2,4]triazol-3-ylsulfanyl)-pyrido-[3,2-d]pyrimidin-4-yl-thiazol-2-yl-amine The compound of Example 33 was manufactured by the same method as in Example 31, by a similar method thereto or by a combination of such a method with a conventional method using 4,6-dichloro-pyrido[3,2-d]pyrimidine, 2-aminothiazole and 3-mercapto-4-methyl-1,2,4-triazole.

$^1$HNMR (CDCl$_3$) δ: 3.82 (3H, s), 7.12 (1H, d, J=3.6Hz), 7.53 (1H, d, J=3.6Hz), 7.63 (1H, d, J=8.8Hz), 8.14 (1H, d, J=8.8Hz), 8.63 (1H, s), 8.89 (1H, s)

ESI-MS (m/e): 343 [M+H]$^+$

Example 34

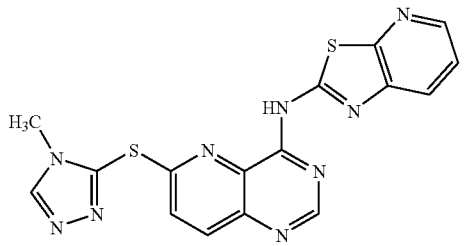

[6-(4-Methyl-4H-[1,2,4]triazol-3-ylsulfanyl)-pyrido-[3,2-d]pyrimidin-4-yl)-thiazolo[5,4-b]pyridin-2-yl-amine The compound of Example 34 was manufactured by the same method as in Example 31, by a similar method thereto or by a combination of such a method with a conventional method using 4,6-dichloro-pyrido[3,2-d]pyrimidine, thiazolo[5,4-b]-pyridin-2-yl-amine and 3-mercapto-4-methyl-1,2,4-triazole.

$^1$HNMR (CD$_3$OD) δ: 3.85 (3H, s), 7.47 (1H, m), 7.68 (1H, d, J=8.8Hz), 8.09 (1H, m), 8.20 (1H, d, J=8.8Hz), 8.46 (1H, brs), 8.74 (1H, brs), 8.95 (1H, brs)

ESI-MS (m/e): 394 [M+H]$^+$

Example 35

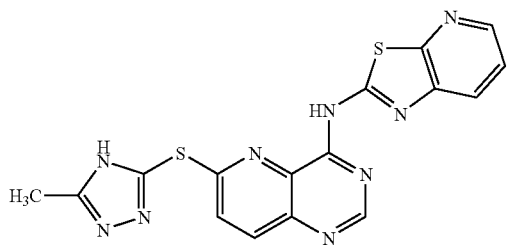

[6-(5-Methyl-4H-[1,2,4]triazol-3-ylsulfanyl)-pyrido-[3,2-d]pyrimidin-4-yl)-thiazolo[5,4-b]pyridin-2-yl-amine The compound of Example 35 was manufactured by the same method as in Example 31, by a similar method thereto or by a combination of such a method with a conventional method using 4,6-dichloro-pyrido[3,2-d]pyrimidine, thiazolo[5,4-b]-pyridin-2-yl-amine and 3-mercapto-5-methyl-1,2,4-triazole.

$^1$HNMR (CD$_3$OD) δ: 3.85 (3H, s), 7.47 (1H, m), 7.68 (1H, d, J=8.8Hz), 8.09 (1H, m), 8.20 (1H, d, J=8.8Hz), 8.46 (1H, brs), 8.74 (1H, brs), 8.95 (1H, brs)

ESI-MS (m/e): 394 [M+H]$^+$

Example 36

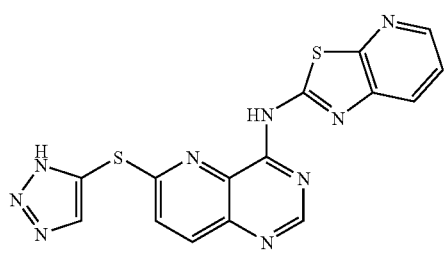

Thiazolo[5,4-b]pyridin-2-yl-[6-(3H-[1,2,3]triazol-4-ylsulfanyl)-pyrido[3,2-d]pyrimidin-4-yl]-amine The compound of Example 36 was manufactured by the same method as in Example 31, by a similar method thereto or by a combination of such a method with a conventional method using 4,6-dichloro-pyrido[3,2-d]pyrimidine, thiazolo[5,4-b]-pyridin-2-yl-amine and 3H-[1,2,3]tirazol-4-thiol.

$^1$HNMR (CDCl$_3$) δ: 7.42 (1H, brs), 7.50 (1H, brs), 8.03-8.06 (2H, m), 8.13 (1H, d, J=8.4Hz), 8.48 (1H, brs), 8.90 (1H, s)

ESI-MS (m/e): 380 [M+H]$^+$

Example 37

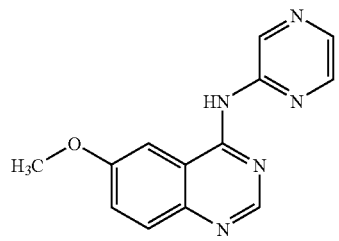

(6-Methoxy-quinazolin-4-yl)-pyrazin-2-yl-amine

The compound of Example 37 was manufactured using 4-chloro-6-methoxy-quinazoline and 2-aminopyrazine by the same method as in Example 1 for the manufacture of (6-iodoquinazolin-4-yl)-thiazolo[5,4-b]pyridin-2-yl-amine, by a similar method thereto or by a combination of such a method with a conventional method.

$^1$HNMR (CDCl$_3$) δ: 3.99 (3H×1/2, s), 4.01 (3H×1/2, s), 7.14-8.35 (5H, m), 8.39 (1H×1/2, brs), 8.72 (1H×1/2, brs), 8.85 (1H×1/2, brs), 10.10 (1H×1/2, brs)

ESI-MS (m/e): 255 [M+H]$^+$

Example 38

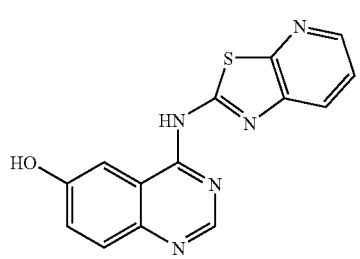

(6-Hydroxy-quinazolin-4-yl)-thiazolo[5,4-b]pyridin-2-yl-amine

The compound of Example 38 was manufactured using 6-acetoxy-4-chloro-quinazoline and thiazolo[5,4-b]pyridin-2-yl-amine by the same method as in Example 1 for the manufacture of 6-iodoquinazolin-4-yl)-thiazolo[5,4-b]pyridin-2-yl-amine, by a similar method thereto or by a combination of such a method with a conventional method.

$^1$HNMR (DMSO) δ: 7.49-7.53 (2H, m), 7.77 (1H, brs), 7.98 (1H, brs), 8.07 (1H, brs), 8.45 (1H, d, J=3.6Hz), 10.31 (1H, s)

ESI-MS (m/e): 296 [M+H]$^+$

Example 39

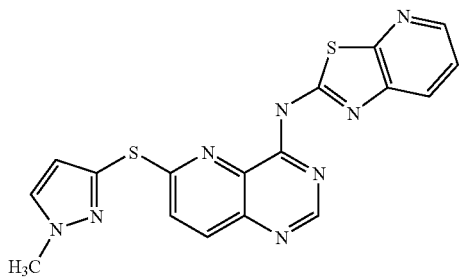

6-(1-Methylpyrazol-3-ylsulfanyl)-thiazolo[5,4-b]-pyridin-2-ylpyrido[3,2-d]pyrimidin-4-yl-amine The compound of Example 39 was manufactured by the same method as in Example 31, by a similar method thereto or by a combination of such a method with a conventional method using 3-mercapto-1-methylpyrazole, thiazolo[5,4-b]pyridin-2-yl-amine and 4,6-dichloro-pyrido[3,2-d]pyrimidine.

$^1$HNMR (CD$_3$OD) δ: 4.09 (3H, s), 6.67 (1H, d, J=2.0Hz), 7.49 (1H, dd, J=8.0, 4.8Hz), 7.53 (1H, d, J=8.8Hz), 7.76 (1H, d, J=2.0Hz), 8.06 (1H, d, J=8.8Hz), 8.13 (1H, dd, J=8.0, 1.6Hz), 8.47 (1H, dd, J=4.8, 1.6Hz), 8.92 (1H, s)

ESI-MS (m/e): 393 [M+H]$^+$

Example 40

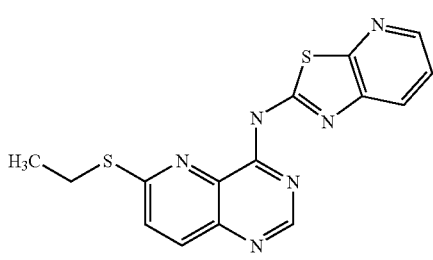

(6-Ethylsulfanyl)-thiazolo[5,4-b]pyridin-2-ylpyrido-[3,2-d]pyrimidin-4-yl-amine

The compound of Example 40 was manufactured by the same method as in Example 31, by a similar method thereto or by a combination of such a method with a conventional method using ethanethiol, 4,6-dichloro-pyrido[3,2-d]pyrimidine and thiazolo[5,4-b]pyridin-2-yl-amine.

$^1$HNMR (CDCl$_3$) δ: 1.53 (3H, t, J=7.2Hz), 3.40 (2H, q, J=7.2Hz), 7.41 (1H, dd, J=8.0, 4.8Hz), 7.61 (1H, d, J=8.8Hz), 8.02 (1H, d, J=8.8Hz), 8.05 (1H, dd, J=8.0, 1.6Hz), 8.51 (1H, dd, J=4.8, 1.6Hz), 8.95 (1H, s)

ESI-MS (m/e): 341 [M+H]$^+$

Example 41

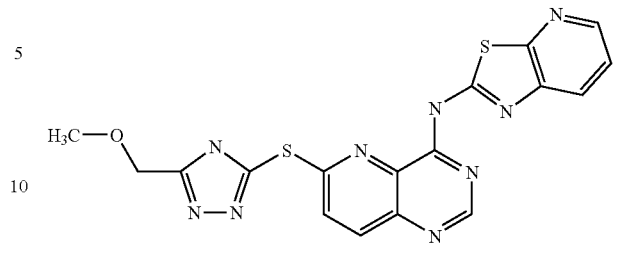

(5-Methoxymethyl-1,2,4-triazol-3-ylsulfanyl)-thiazolo[5,4-b]pyridin-2-ylpyrido-[3,2-d]pyrimidin-4-yl-amine The compound of Example 41 was manufactured by the same method as in Example 31, by a similar method thereto or by a combination of such a method with a conventional method using 3-mercapto-5-methoxymethyl[1,2,4]triazole, 4,6-dichloro-pyrido-[3,2-d]pyrimidine and thiazolo[5,4-b]pyridin-2-yl-amine.

$^1$HNMR (CD$_3$OD) δ: 3.55 (3H, s), 4.75 (2H, s), 7.49 (1H, dd, J=8.0, 4.8Hz), 7.73 (1H, d, J=8.8Hz), 8.10 (1H, d, J=8.0Hz), 8.14 (1H, d, J=8.8Hz), 8.48 (1H, d, J=4.8Hz), 8.96 (1H, s)

ESI-MS (m/e): 424 [M+H]$^+$

Example 42

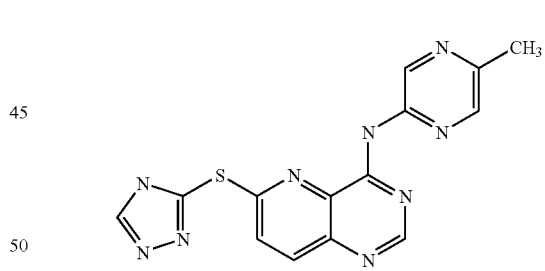

(5-methylpyrazin-2-yl)-6-(1,2,4-triazol-3-yl-sulfanyl)pyrido[3,2-d]pyrimidin-4-yl-amine The compound of Example 42 was manufactured by the same method as in Example 31, by a similar method thereto or by a combination of such a method with a conventional method using 3-mercapto-[1,2,4]triazole, 4,6-dichloropyrido-[3,2-d]-pyrimidine and 2-amino-5-methylpyrazine.

$^1$HNMR (CD$_3$OD) δ: 2.60 (3H, s), 7.64 (1H, d, J=9.20Hz), 8.06 (1H, d, J=9.20Hz), 8.23 (1H, s), 8.52 (1H, s), 8.80 (1H, s), 9.88 (1H, d, J=1.6Hz)

ESI-MS (m/e): 338 [M+H]$^+$

Example 43

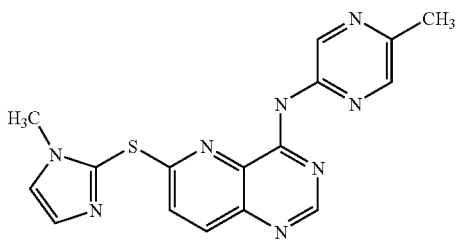

6-(1-Methylimidazol-2-yl-sulfanyl)-(5-methylpyrazin-2-yl)pyrido[3,2-d]pyrimidin-4-yl-amine The compound of Example 43 was manufactured by the same method as in Example 31, by a similar method thereto or by a combination of such a method with a conventional method using 2-mercapto-1-methylimidazole, 2-amino-5-methylpyrazine and 4,6-dichloropyrido-[3,2-d]pyrimidine.

$^1$HNMR (CD$_3$OD) δ: 2.60 (3H, s), 3.82 (3H, s), 7.34 (1H, d, J=1.2Hz), 7.39-7.43 (2H, m), 8.07 (1H, d, J=8.8Hz), 8.29 (1H, s), 8.80 (1H, s), 9.85 (1H, d, J=1.2Hz)
ESI-MS (m/e): 351 [M+H]$^+$

Example 44

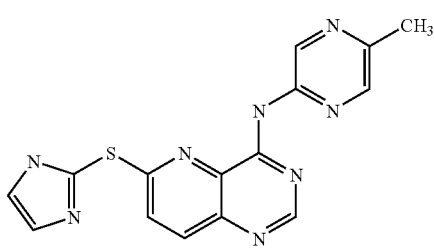

6-(Imidazol-2-yl-sulfanyl)-(5-methylpyrazin-2-yl)-pyrido[3,2-d]pyrimidin-4-yl-amine The compound of Example 44 was manufactured by the same method as in Example 31, by a similar method thereto or by a combination of such a method with a conventional method using 2-mercaptoimidazole, 2-amino-5-methylpyrazine and 4,6-dichloropyrido-[3,2-d]pyrimidine.

$^1$HNMR (CD$_3$OD) δ: 2.59 (3H, s), 7.32 (1H, d, J=8.8Hz), 7.35 (2H, s), 8.00 (1H, d, J=8.8Hz), 8.27 (1H, d, J=1.2Hz), 8.76 (1H, s), 9.83 (1H, d, J=1.2Hz)
ESI-MS (m/e): 337 [M+H]$^+$

Example 45

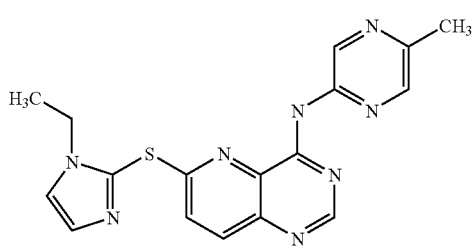

6-(1-Ethylimidazol-2-yl-sulfanyl)-(5-methylpyrazin-2-yl)-pyrido[3,2-d]pyrimidin-4-yl-amine The compound of Example 45 was manufactured by the same method as in Example 31, by a similar method thereto or by a combination of such a method with a conventional method using 1-ethyl-2-mercaptoimidazole, 2-amino-5-methylpyrazine and 4,6-dichloropyrido-[3,2-d]pyrimidine.

$^1$HNMR (CD$_3$OD) δ: 1.42 (3H, t, J=7.2Hz), 2.59 (3H, s), 4.21 (2H, q, J=7.2Hz), 7.37 (1H, s), 7.49 (1H, d, J=8.8Hz), 7.54 (1H, d, J=1.2Hz), 8.10 (1H, d, J=8.8Hz), 8.33 (1H, s), 8.80 (1H, s), 9.83 (1H, d, J=1.2Hz)
ESI-MS (m/e): 365 [M+H]$^+$

Example 46

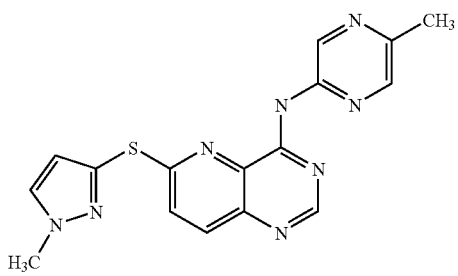

(5-Methylpyrazin-2-yl)-6-(1-methylpyrazol-3-yl-sulfanyl)pyrido[3,2-d]pyrimidin-4-yl-amine The compound of Example 46 was manufactured by the same method as in Example 31, by a similar method thereto or by a combination of such a method with a conventional method using 3-mercapto-1-methylpyrazol, 2-amino-5-methylpyrazine and 4,6-dichloropyrido-[3,2-d]pyrimidine.

$^1$HNMR (CD$_3$OD) δ: 2.59 (3H, s), 4.08 (3H, s), 6.66 (1H, d, J=2.0Hz), 7.55 (1H, d, J=8.8Hz), 7.80 (1H, d, J=2.0Hz), 8.00 (1H, d, J=8.8Hz), 8.33 (1H, s), 8.77 (1H, s), 9.85 (1H, d, J=1.2Hz)
ESI-MS (m/e): 351 [M+H]$^+$

Example 47

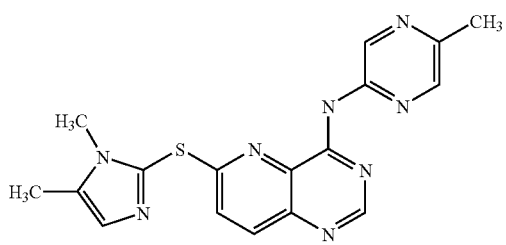

6-(1,5-Dimethylimidazol-2-ylsulfanyl)-(5-methyl-pyrazin-2-yl)pyrido[3,2-d]pyrimidin-4-yl-amine The compound of Example 47 was manufactured by the same method as in Example 31, by a similar method thereto or by a combination of such a method with a conventional method using 2-mercapto-1,5-dimethylimidazole, 2-amino-5-methylpyrazine and 4,6-dichloro-pyrido[3,2-d]pyrimidine.

$^1$HNMR (CD$_3$OD) δ: 2.44 (3H, s), 2.60 (3H, s), 3.70 (3H, s), 7.10 (1H, s), 7.48 (1H, d, J=8.8Hz), 8.08 (1H, d, J=8.8Hz), 8.31 (1H, s), 8.80 (1H, s), 9.84 (1H, d, J=1.2Hz)
ESI-MS (m/e): 365 [M+H]$^+$

Example 48

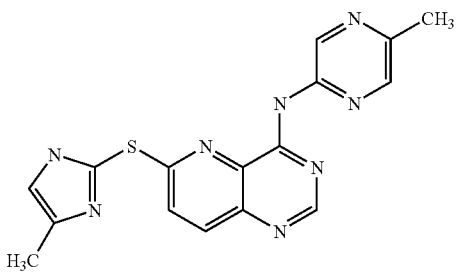

6-(4-Methylimidazol-2-ylsulfanyl)-(5-methylpyrazin-2-yl)pyrido[3,2-d]pyrimidin-4-yl-amine The compound of Example 48 was manufactured by the same method as in Example 31, by a similar method thereto or by a combination of such a method with a conventional method using 2-mercapto-4-methylimidazole, 2-amino-5-methylpyrazine and 4,6-dichloro-pyrido[3,2-d]pyrimidine.

$^1$HNMR (CD$_3$OD) δ: 2.37 (3H, s), 2.59 (3H, s), 7.04 (1H, s), 7.37 (1H, d, J=8.8Hz), 8.00 (1H, d, J=8.8Hz), 8.29 (1H, s), 8.76 (1H, s), 9.83 (1H, d, J=1.2Hz)

ESI-MS (m/e): 351 [M+H]$^+$

Example 49

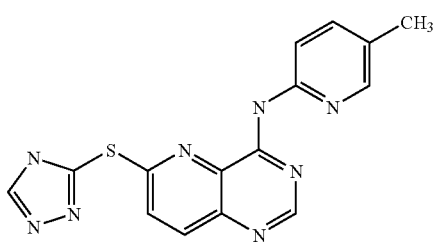

(5-Methylpyridin-2-yl)-6-(1,2,4-triazol-3-yl-sulfanyl)pyrido[3,2-d]pyrimidin-4-yl-amine The compound of Example 49 was manufactured by the same method as in Example 31, by a similar method thereto or by a combination of such a method with a conventional method using 3-mercapto-[1,2,4]triazole, 2-amino-5-methylpyrazine and 4,6-dichloro-pyrido[3,2-d]pyrimidine.

$^1$HNMR (CD$_3$OD) δ: 2.28 (3H, s), 7.53 (1H, d, J=8.8Hz), 7.57 (1H, dd, J=8.8, 3.2Hz), 7.93 (1H, d, J=8.8Hz), 8.08 (1H, s), 8.33 (1H, s), 8.54 (1H, d, J=8.8Hz), 8.65 (1H, s)

ESI-MS (m/e): 337 [M+H]$^+$

Example 50

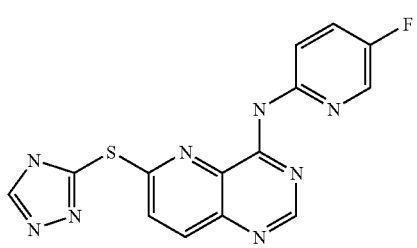

(5-Fluoropyridin-2-yl)-6-(1,2,4-triazol-3-yl-sulfanyl)pyrido[3,2-d]pyrimidin-4-yl-amine The compound of Example 50 was manufactured by the same method as in Example 31, by a similar method thereto or by a combination of such a method with a conventional method using 3-mercapto-[1,2,4]triazole, 2-amino-5-fluoropyridine and 4,6-dichloro-pyrido[3,2-d]pyrimidine.

$^1$HNMR (CD$_3$OD) δ: 7.51-7.60 (2H, m), 7.63 (1H, d, J=8.8Hz), 8.04 (1H, d, J=8.8Hz), 8.24 (1H, d, J=2.4Hz), 8.75 (1H, s), 8.77-8.81 (1H, m)

ESI-MS (m/e): 341 [M+H]$^+$

Example 51

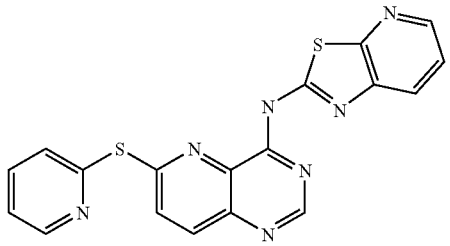

[6-(Pyridin-2-ylsulfanyl)-pyrido[3,2-d]pyrimidin-4-yl-thiazolo[5,4-b]pyridin-2-yl-amine The compound of Example 51 was manufactured by the same method as in Example 31, by a similar method thereto or by a combination of such a method with a conventional method using 2-mercapto-pyridine, thiazole[5,4-b]pyridin-2-yl-amine and 4,6-dichloro-pyrido[3,2-d]pyrimidine.

$^1$HNMR (CDCl$_3$) δ7.39-7.45 (2H, m), 7.67-7.70 (1H, m), 7.80 (1H, d, J=8.8Hz), 7.82-7.87 (1H, m), 8.06-8.08 (1H, m), 8.14 (1H, d, J=8.8Hz), 8.48-8.50 (1H, m), 8.67-8.69 (1H, m), 8.97 (1H, s)

ESI-MS (m/e): 390 [M+H]$^+$

Example 52

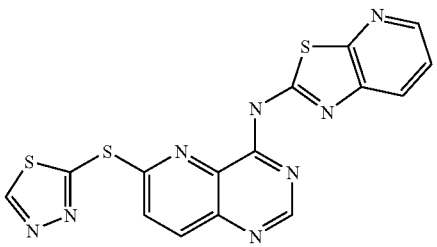

[6-(1,3,4-Thiadiazol-2-ylsulfanyl)-pyrido[3,2-d]-pyrimidin-4-yl]-thiazolo[5,4-b]pyridin-2-yl-amine The compound of Example 52 was manufactured by the same method as in Example 31, by a similar method thereto or by a combination of such a method with a conventional method using 2-mercapto-[1,3,4]thiadiazole, thiazolo[5,4-b]pyridin-2-yl-amine and 4,6-dichloro-pyrido[3,2-d]pyrimidine.

$^1$HNMR (DMSO) δ7.46 (1H, dd, J=4.8, 8.4Hz), 7.91 (1H, d, J=8.8Hz), 8.10 (1H, dd, J=1.6, 8.4Hz), 8.29 (1H, d, J=8.8Hz), 8.53 (1H, dd, J=1.6, 4.8Hz), 9.04 (1H, s), 9.52 (1H, s)

ESI-MS (m/e): 397 [M+H]$^+$

Example 53

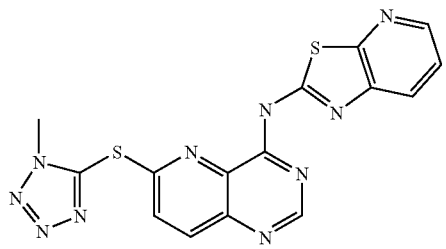

[6-(1-Methyl-1H-tetrazol-5-ylsulfanyl)-pyrido[3,2-d]-pyrimidin-4-yl]-thiazolo[5,4-b]pyridin-2-yl-amine The compound of Example 53 was manufactured by the same method as in Example 31, by a similar method thereto or by a combination of such a method with a conventional method using 5-mercapto-1-methyl-1H-tetrazole, thiazolo[5,4-b]pyridin-2-yl-amine and 4,6-dichloro-pyrido[3,2-d]pyrimidine.

$^1$HNMR (DMSO) δ4.15 (3H, s), 7.56 (1H, dd, J=4.6, 8.2Hz), 7.96 (1H, d, J=8.8Hz), 8.19-8.22 (1H, m), 8.37 (1H, d, J=8.8Hz), 8.52 (1H, dd, J=1.6, 4.6Hz), 9.03 (1H, s)

ESI-MS (m/e): 395 [M+H]+

Example 54

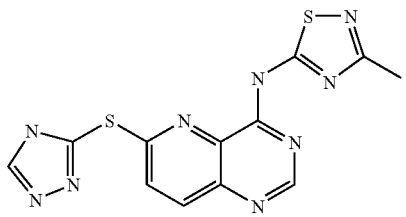

[6-(4H-[1,2,4]triazol-3-ylsulfanyl)-pyrido[3,2-d]-pyrimidin-4-yl]-3-methyl-[1,2,4]thiadiazol-5-yl-amine The compound of Example 54 was manufactured by the same method as in Example 31, by a similar method thereto or by a combination of such a method with a conventional method using 3-mercapto-4H-[1,2,4]triazole, 5-amino-3-methyl-[1,2,4]-thiazole and 4,6-dichloro-pyrido[3,2-d]pyrimidine.

3-Mercapto-4H-[1,2,4]triazole (54 mg; 0.54 mmol) and 100 mg (0.36 mmol) of (6-chloro-pyrido[3,2-d]pyrimidin-4-yl)-3-methyl-[1,2,4]thiadiazol-5-yl-amine were added to a solution of 80 mg (0.72 mmol) of tert-butoxy potassium in 3 ml of N,N-dimethylacetamide and the mixture was stirred at 130° C. for 16 hours. Water was added to the reaction solution and the mixture was extracted with chloroform. The organic layer was dried and concentrated and the resulting residue was purified by a reversed phase preparative HPLC (0.1% TFA-containing water:acetonitrile=90:10→10:90) to give 3 mg (yield: 2%) of the title compound as a yellow solid.

$^1$HNMR (DMSO) δ2.53 (3H, s), 7.61 (1H, s), 8.25-8.27 (2H, m), 8.94 (1H, s)

ESI-MS (m/e): 344 [M+H]+

Example 55

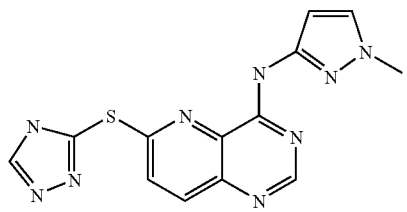

[6-(4H-[1,2,4]triazol-3-ylsulfanyl)-pyrido[3,2-d]-pyrimidin-4-yl]-(1-methyl-1H-pyrazol-3-yl)-amine The compound of Example 55 was manufactured by the same method as in Example 31, by a similar method thereto or by a combination of such a method with a conventional method using 3-mercapto-[1,2,4]triazole, 5-amino-1-methyl-1H-pyrazole and 4,6-dichloro-pyrido[3,2-d]pyrimidine.

3-Mercapto-4H-[1,2,4]triazole (128 mg; 1.27 mmol) and (6-chloro-pyrido[3,2-d]pyrimidin-4-yl)-3-amino-1-methyl-1H-pyrazole (110 mg; 0.42 mmol) were added to a solution of 120 mg (1.06 mmol) of tert-butoxy potassium in 5 ml of N,N-dimethylacetamide and the mixture was stirred at 130° C. for 5 hours. Water was added to the reaction solution and the mixture was extracted with chloroform. The organic layer was dried and concentrated and the resulting residue was purified by a reversed phase preparative HPLC (0.1% TFA-containing water: acetonitrile=90:10→10:90) to give 57 mg (yield: 33%) of the title compound as a yellow solid.

$^1$HNMR (DMSO) δ3.84 (3H, s), 6.79 (1H, d, J=3.6Hz), 7.62 (1H, d, J=8.8Hz), 7.73 (1H, d, J=3.6Hz), 8.12 (1H, d, J=8.8Hz), 8.73 (1H, s), 8.84 (1H, s)

ESI-MS (m/e): 326 [M+H]+

Example 56

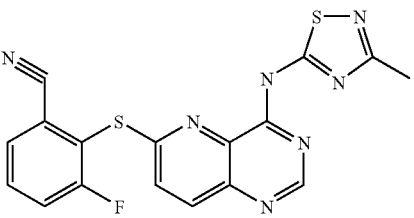

[6-(3-Fluoro-benzonitrile-2-ylsulfanyl)-pyrido-[3,2-d]pyrimidin-4-yl]-3-methyl-[1,2,4]thiadiazol-5-yl-amine The compound of Example 56 was manufactured by the same method as in Example 31, by a similar method thereto or by a combination of such a method with a conventional method using 3-fluoro-2-mercapto-benzonitrile, 5-amino-3-methyl-[1,2,4]-thiadiazole and 4,6-dichloro-pyrido[3,2-d]pyrimidine.

$^1$HNMR (CDCl$_3$) δ: 2.59 (3H, s), 7.59-7.64 (1H, m), 7.68 (1H, d, J=9.0Hz), 7.75-7.79 (2H, m), 8.20 (1H, d, J=9.0Hz), 8.98 (1H, s)

ESI-MS (m/e): 396 [M+H]+

Example 57

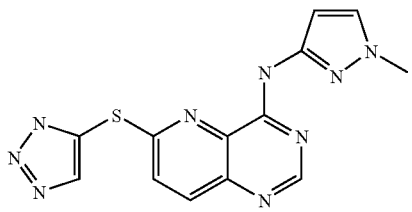

[6-(3H-[1,2,3]Triazol-4-ylsulfanyl)-pyrido-[3,2-d]-pyrimidin-4-yl]-(1-methyl-1H-pyrazol-3-yl)-amine The compound of Example 57 was manufactured by the same method as in Example 31, by a similar method thereto or by a combination of such a method with a conventional method using 4-mercapto-3H-[1,2,3]triazole, 3-amino-1-methyl-1H-pyrazole and 4,6-dichloro-pyrido[3,2-d]pyrimidine.

$^1$HNMR (CDCl$_3$) δ: 3.90 (3H, s), 7.03 (1H, d, J=2.3Hz), 7.38 (1H, d, J=2.3Hz), 7.49 (1H, d, J=9.0Hz), 7.98-8.00 (2H, m), 8.69 (1H, s)

ESI-MS (m/e): 326 [M+H]+

Example 58

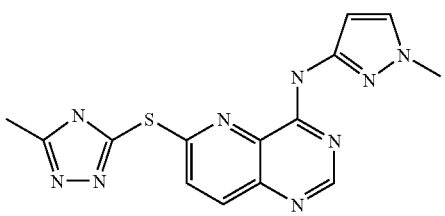

[6-(5-Methyl-4H-[1,2,4]triazol-3-ylsulfanyl)-pyrido-[3,2-d]pyrimidin-4-yl]-(1-methyl-1H-pyrazol-3-yl)-amine The compound of Example 58 was manufactured by the same method as in Example 31, by a similar method thereto or by a combination of such a method with a conventional method using 3-mercapto-5-methyl-4H-[1,2,4]triazole, 3-amino-1-methyl-1H-pyrazole and 4,6-dichloro-pyrido[3,2-d]pyrimidine.

$^1$HNMR (CDCl$_3$) δ: 2.57 (3H, s), 3.90 (3H, s), 7.04 (1H, d, J=2.3Hz), 7.38 (1H, d, J=2.3Hz), 7.62 (1H, d, J=8.8Hz), 8.00 (1H, d, J=8.8Hz), 8.70 (1H, s)

ESI-MS (m/e): 340 [M+H]+

Example 59

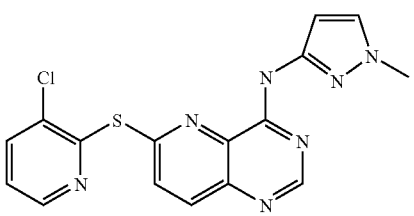

[6-(3-Chloro-pyridin-2-ylsulfanyl)-pyrido[3,2-d]-pyrimidin-4-yl]-(1-methyl-1H-pyrazol-3-yl)-amine The compound of Example 59 was manufactured by the same method as in Example 31, by a similar method thereto or by a combination of such a method with a conventional method using 3-chloro-2-mercapto-pyridine, 3-amino-1-methyl-1H-pyrazole and 4,6-dichloro-pyrido[3,2-d]pyrimidine.

$^1$HNMR (CDCl$_3$) δ: 3.86 (3H, s), 6.98 (1H, d, J=2.3Hz), 7.17-7.18 (1H, m), 7.34 (1H, d, J=2.3Hz), 7.74 (1H, dd, J=8.2, 1.6Hz), 7.81 (1H, d, J=8.6Hz), 8.06 (1H, d, J=8.6Hz), 8.35 (1H, dd, J=4.5, 1.6Hz), 8.75 (1H, s), 9.24 (1H, s)

ESI-MS (m/e): 370 [M+H]+

Example 60

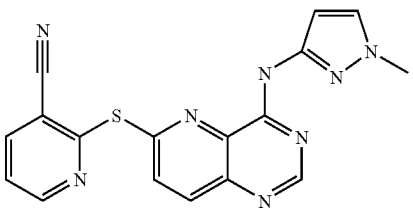

[6-(3-Cyano-pyridin-2-ylsulfanyl)-pyrido[3,2-d]-pyrimidin-4-yl]-(1-methyl-1H-pyrazol-3-yl)-amine The compound of Example 60 was manufactured by the same method as in Example 31, by a similar method thereto or by a combination of such a method with a conventional method using 3-cyano-2-mercapto-pyridine, 3-amino-1-methyl-1H-pyrazole and 4,6-dichloro-pyrido[3,2-d]pyrimidine.

$^1$HNMR (DMSO-d6) δ: 3.82 (3H, s), 6.78 (1H, d, J=2.2Hz), 7.63-7.65 (1H, m), 7.72 (1H, d, J=2.2Hz), 8.03 (1H, d, J=8.8Hz), 8.21 (1H, d, J=8.8Hz), 8.48-8.50 (1H, m), 8.76 (1H, s), 8.79-8.79 (1H, m)

ESI-MS (m/e): 361 [M+H]+

Example 61

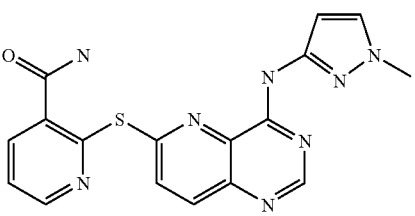

[6-(3-Amido-pyridin-2-ylsulfanyl)-pyrido[3,2-d]-pyrimidin-4-yl]-(1-methyl-1H-pyrazol-3-yl)-amine The compound of Example 61 was manufactured by the same method as in Example 31, by a similar method thereto or by a combination of such a method with a conventional method using 3-carbamoyl-2-mercapto-pyridine, 3-amino-1-methyl-1H-pyrazole and 4,6-dichloro-pyrido[3,2-d]pyrimidine.

$^1$HNMR (CD$_3$OD) δ: 3.80 (3H, s), 6.86 (1H, d, J=2.2Hz), 7.27-7.30 (2H, m), 7.71 (1H, d, J=8.8Hz), 7.95 (1H, d, J=8.8Hz), 8.00-8.02 (1H, m), 8.46-8.48 (1H, m), 8.60 (1H, s).

ESI-MS (m/e): 379 [M+H]+

Example 62

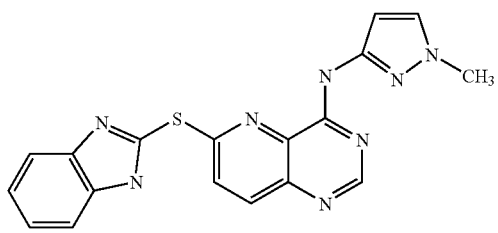

6-(1H-Benzimidazol-2-ylsulfanyl)-N-(1-methyl-1H-pyrazol-3-yl)pyrido[3,2-d]pyrimidin-4-yl-amine The compound of Example 62 was manufactured by the same method as in Example 31, by a similar method thereto or by a combination of such a method with a conventional method using 2-mercapto-1H-benzimidazole, 3-amino-1-methyl-1H-pyrazole and 4,6-dichloro-pyrido[3,2-d]pyrimidine.

$^1$HNMR (CDCl$_3$) δ: 3.94 (3H, s), 6.99 (1H, d, J=3.1Hz), 7.45-7.51 (3H, m), 7.70-7.73 (2H, m), 7.99 (1H, d, J=8.6Hz), 8.34 (1H, d, J=8.6Hz), 8.75 (1H, s)

ESI-MS (m/e): 375 [M+H]$^+$

Example 63

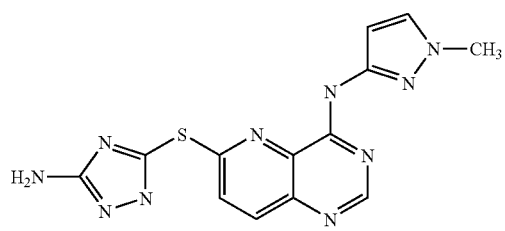

6-[(5-Amino-4H-1,2,4-triazol-3-yl)sulfanyl]-N-(1-methyl-1H-pyrazol-3-yl)pyrido[3,2-d]pyrimidin-4-yl-amine The compound of Example 63 was manufactured by the same method as in Example 31, by a similar method thereto or by a combination of such a method with a conventional method using 5-amino-3-mercapto-4H-[1,2,4]triazole, 3-amino-1-methyl-1H-pyrazole and 4,6-dichloro-pyrido[3,2-d]pyrimidine.

$^1$HNMR (CD$_3$OD) δ: 3.89 (3H, s), 6.93 (1H, d, J=2.0Hz), 7.59 (1H, d, J=2.0Hz), 7.68 (1H, d, J=9.0Hz), 8.03 (1H, d, J=9.0Hz), 8.63 (1H, s)

ESI-MS (m/e): 341 [M+H]

Example 64

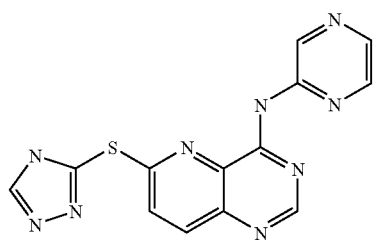

N-Pyrazin-2-yl-6-(4H-1,2,4-triazol-3-ylsulfanyl)-pyrido[3,2-d]pyrimidin-4-yl-amine The compound of Example 64 was manufactured by the same method as in Example 31, by a similar method thereto or by a combination of such a method with a conventional method using 3-mercapto-4H-[1,2,4]triazole, 2-amino-pyrazine and 4,6-dichloro-pyrido[3,2-d]pyrimidine.

$^1$HNMR (CD$_3$OD) δ: 7.77 (1H, d, J=9.0Hz), 8.15 (1H, d, J=9.0Hz), 8.39 (1H, d, J=2.3Hz), 8.45-8.48 (1H, m), 8.75 (1H, s), 8.84 (1H, s), 9.99 (1H, s)

ESI-MS (m/e): 324 [M+H]

Example 65

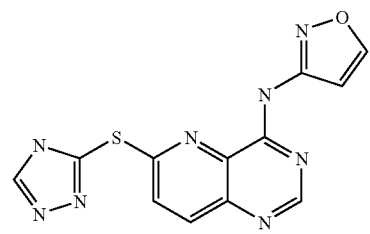

N-Isoxazol-3-yl-6-(4H-1,2,4-triazol-3-ylsulfanyl)-pyrido[3,2-d]pyrimidin-4-yl-amine The compound of Example 65 was manufactured by the same method as in Example 31, by a similar method thereto or by a combination of such a method with a conventional method using 3-mercapto-4H-[1,2,4]triazole, 3-amino-oxazole and 4,6-dichloro-pyrido[3,2-d]pyrimidine.

$^1$HNMR (CD$_3$OD) δ: 7.37 (1H, d, J=1.6Hz), 7.69 (1H, d, J=8.6Hz), 8.10 (1H, d, J=9.0Hz), 8.65 (1H, d, J=1.6Hz), 8.72 (1H, s), 8.75 (1H, s)

ESI-MS (m/e): 313 [M+H]

Example 66

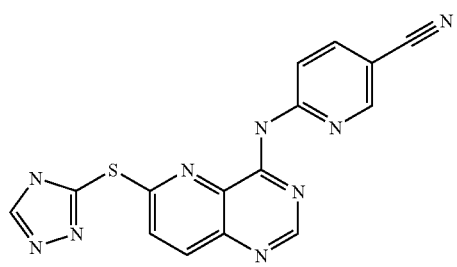

6-{[6-(4H-1,2,4-Triazol-3-ylsulfanyl)pyrido[3,2-d]-pyrimidin-4-yl]amino}-nicotinonitrile The compound of Example 66 was manufactured by the same method as in Example 31, by a similar method thereto or by a combination of such a method with a conventional method using 3-mercapto-4H-[1,2,4]triazole, 3-amino-5-cyano-pyridine and 4,6-dichloro-pyrido[3,2-d]pyrimidine.

$^1$HNMR (DMSO-d6) δ: 7.72-7.75 (1H, m), 8.24 (1H, d, J=9.0Hz), 8.39-8.41 (1H, m), 8.80 (1H, d, J=9.0Hz), 8.85-8.93 (2H, m), 9.62 (1H, s)

ESI-MS (m/e): 348 [M+H]

Example 68

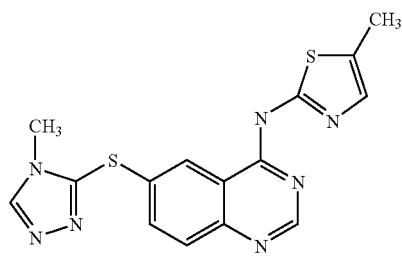

(5-Methyl-3-thiazol-2-yl)-6-(4-methyl-1,2,4-triazol-3-ylsulfanyl)-quinazolin-4-yl-amine The compound of Example 68 was manufactured by the same method as in Example 1, by a similar method thereto or by a combination of such a method with a conventional method using 3-mercapto-4-methyl-[1,2,4]triazole, 2-amino-5-methyl-1,3-thiazole and 4-chloro-6-iodoquinazoline.

$^1$HNMR (CDCl$_3$) δ: 2.43 (3H, s), 3.65 (3H, s), 7.13 (1H, s), 7.62 (2H, brs), 8.25 (1H, brs), 8.31 (1H, s), 8.46 (1H, s)

ESI-MS (m/e): 354 [M+H]$^+$

Example 67

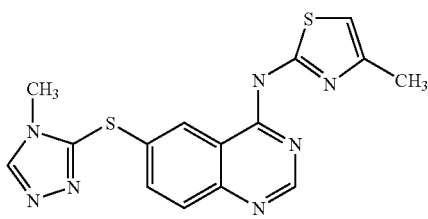

(4-Methyl-1,3-thiazol-2-yl)-6-(4-methyl-1,2,4-triazol-3-ylsulfanyl)-quinazolin-4-yl-amine The compound of Example 67 was manufactured by the same method as in Example 1, by a similar method thereto or by a combination of such a method with a conventional method using 3-mercapto-4-methyl-[1,2,4]triazole, 2-amino-4-methyl-1,3-thiazole and 4-chloro-6-iodoquinazoline.

$^1$HNMR (CDCl$_3$) δ: 2.40 (3H, s), 3.66 (3H, s), 6.55 (1H, s), 7.64 (2H, brs), 8.25 (1H, brs), 8.31 (1H, s), 8.46 (1H, s)

ESI-MS (m/e): 354 [M+H]$^+$

Example 69

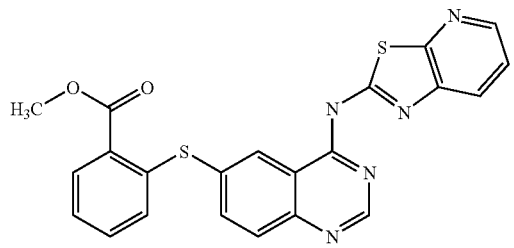

(6-Methylbenzoate-2-ylsulfanyl)-thiazolo[5,4-b]-pyridin-2-ylquinazolin-4-yl-amine The compound of Example 69 was manufactured by the same method as in Example 1, by a similar method thereto or by a combination of such a method with a conventional method using methyl 2-mercaptobenzoate, thiazole[5,4-b]pyridin-2-yl-amine and 4-chloro-6-iodoquinazoline.

$^1$HNMR (CD$_3$OD) δ: 3.99 (3H, s), 6.96 (1H, d, J=8.4Hz), 7.23-7.27 (1H, m), 7.32-7.36 (1H, m), 7.44-7.48 (1H, m), 7.91 (1H, brs), 8.02-8.08 (4H, m), 8.45-8.46 (1H, s), 8.78 (1H, s)

ESI-MS (m/e): 446 [M+H]$^+$

Example 70

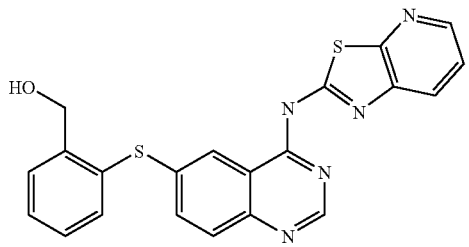

6-(2-Hydroxyethylphenylsulfanyl)-thiazolo[5,4-b]-
pyridin-2-ylquinazolin-4-yl-amine The compound of Example 70 was manufactured by the same method as in Example 1, by a similar method thereto or by a combination of such a method with a conventional method using 2-hydroxymethyl-thiophenol, thiazole[5,4-b]pyridin-2-yl-amine and 4-chloro-6-iodoquinazoline.

$^1$HNMR (CD$_3$OD) δ: 4.83 (2H, s), 7.32 (1H, t, J=7.2Hz), 7.46-7.48 (3H, m), 7.57 (1H, d, J=8.4Hz), 7.67 (1H, d, J=7.2Hz), 7.72 (1H, d, J=8.4Hz), 8.04 (1H, brs), 8.37 (1H, brs), 8.43 (1H, brs), 8.67 (1H, brs)

ESI-MS (m/e): 418 [M+H]$^+$

Example 71

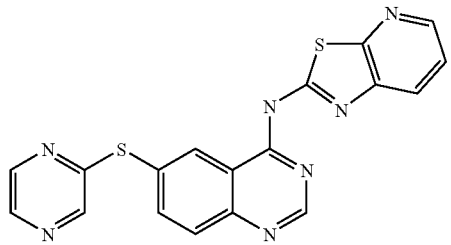

6-(Pyrazin-2-ylsulfanyl)-thiazolo[5,4-b]pyridin-2-yl-
quinazolin-4-yl-amine

The compound of Example 71 was manufactured by the same method as in Example 1, by a similar method thereto or by a combination of such a method with a conventional method using 2-mercapto-pyrazine, thiazole[5,4-b]pyridin-2-yl-amine and 4-chloro-6-iodoquinazoline.

$^1$HNMR (DMSO) δ: 7.51-7.54 (1H, m), 7.97 (1H, brs), 8.07-8.34 (3H, m), 8.48-8.52 (3H, m), 8.60 (1H, d, J=1.6Hz), 8.99 (1H, brs)

ESI-MS (m/e): 390 [M+H]$^+$

Example 72

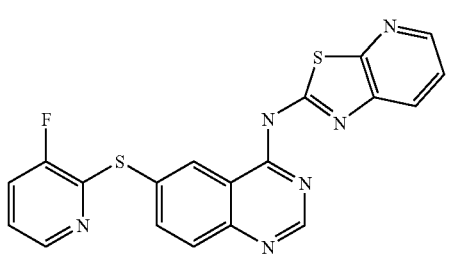

6-(3-Fluoropyridin-2-ylsulfanyl)-thiazolo[5,4-b]-
pyridin-2-yl-quinazolin-4-yl-amine The compound of Example 72 was manufactured by the same method as in Example 1, by a similar method thereto or by a combination of such a method with a conventional method using 3-fluoro-2-mercapto-pyridine, thiazole[5,4-b]pyridin-2-yl-amine and 4,6-dichloro-pyrido[3,2-d]pyrimidine.

$^1$HNMR (CD$_3$OD) δ: 7.21-7.25 (1H, m), 7.43-7.48 (3H, m), 7.86-7.96 (2H, m), 8.06 (1H, d, J=7.2Hz), 8.21-8.24 (1H, m), 8.43 (1H, d, J=4.8Hz), 8.73 (1H, d, J=1.6Hz)

ESI-MS (m/e): 407 [M+H]$^+$

Example 73

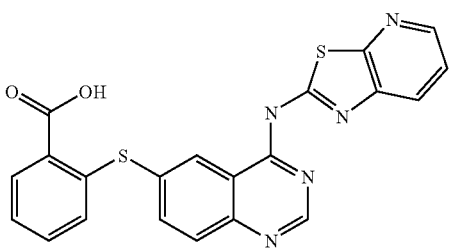

6-(Benzoate-2-ylsulfanyl)-thiazolo[5,4-b]pyridin-2-
ylquinazolin-4-yl-amine

The compound of Example 73 was manufactured by the same method as in Example 1, by a similar method thereto or by a combination of such a method with a conventional method using 2-mercapto-benzoic acid, thiazole[5,4-b]pyridin-2-yl-amine and 4-chloro-6-iodoquinazoline.

$^1$HNMR (DMSO) δ: 6.89 (1H, d, J=8.0Hz), 7.28 (1H, t, J=8.0Hz), 7.39 (1H, t, J=8.0Hz), 7.55 (1H, dd, J=8.0, 4.8Hz), 7.95-8.08 (4H, m), 8.52 (1H, dd, J=4.8, 1.6Hz), 8.90 (1H, brs), 9.13 (1H, s)

ESI-MS (m/e): 432 [M+H]$^+$

Example 74

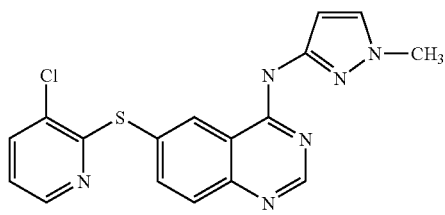

6-(3-Chloropyridin-2-ylsulfanyl)-(1-methylpyrazol-3-yl)quinazolin-4-yl-amine

The compound of Example 74 was manufactured by the same method as in Example 1, by a similar method thereto or by a combination of such a method with a conventional method using 3-chloro-2-mercapto-pyridine, 3-amino-1-methylpyrazole and 4-chloro-6-iodoquinazoline.

$^1$HNMR (CD$_3$OD) δ: 3.88 (1H, s), 6.88 (1H, d, J=2.0Hz), 7.07-7.10 (1H, m), 7.43 (1H, d, J=2.0Hz), 7.69 (1H, dd, J=8.0, 1.6Hz), 7.85 (1H, d, J=8.8Hz), 7.90 (1H, dd, J=8.8, 2.0Hz), 8.20 (1H, dd, J=4.8, 1.6Hz), 8.49 (1H, d, J=1.6Hz), 8.69 (1H, s)

ESI-MS (m/e): 369 [M+H]$^+$

Example 75

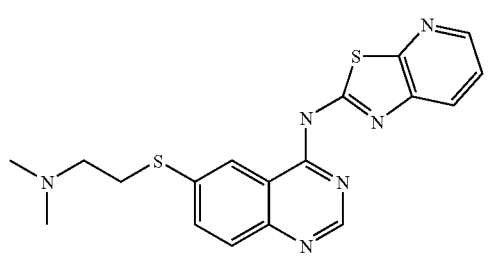

[6-(2-Dimethylamino-ethylsulfanyl)-quinazolin-4-yl]-thiazole[5,4-b]pyridin-2-yl-amine The compound of Example 75 was manufactured by the same method as in Example 1, by a similar method thereto or by a combination of such a method with a conventional method using 2-dimethylaminoethanethiol, thiazole[5,4-b]pyridin-2-yl-amine and 4-chloro-6-iodoquinazoline.

$^1$HNMR (DMSO) δ2.86 (6H, s), 3.36-3.38 (2H, m), 3.53-3.56 (2H, m), 7.54 (1H, dd, J=4.0, 8.0Hz), 7.89 (1H, d, J=8.8Hz), 7.98 (1H, d, J=8.8Hz), 8.13 (1H, d, J=8.0Hz), 8.51 (1H, d, J=4.0Hz), 8.69 (1H, s), 8.92 (1H, s), 9.58 (1H, s)

ESI-MS (m/e): 383 [M+H]$^+$

Example 76

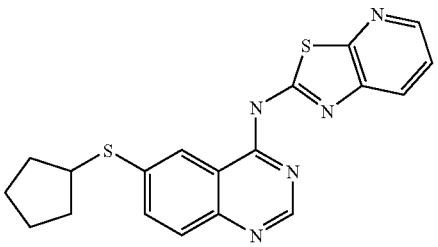

[6-(Cyclopentylsulfanyl)-quinazolin-4-yl]-thiazolo-[5,4-b]pyridin-2-yl-amine

The compound of Example 76 was manufactured by the same method as in Example 1, by a similar method thereto or by a combination of such a method with a conventional method using cyclopentanethiol, thiazole[5,4-b]pyridin-2-yl-amine and 4-chloro-6-iodoquinazoline.

$^1$HNMR (DMSO) δ1.57-1.78 (6H, m), 2.19-2.23 (2H, m), 4.04-4.07 (1H, m), 7.53-7.57 (1H, m), 7.83-7.88 (2H, m), 8.11-8.14 (1H, m), 8.49-8.51 (1H, m), 8.60 (1H, s), 8.94 (1H, s)

ESI-MS (m/e): 380 [M+H]$^+$

Example 77

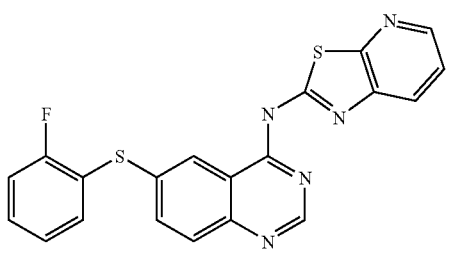

[6-(2-Fluorophenylsulfanyl)-quinazolin-4-yl]-thiazolo[5,4-b]pyridin-2-yl-amine

The compound of Example 77 was manufactured by the same method as in Example 1, by a similar method thereto or by a combination of such a method with a conventional method using 2-fluoro-thiophenol, thiazole[5,4-b]pyridin-2-yl-amine and 4-chloro-6-iodoquinazoline.

$^1$HNMR (DMSO) δ7.26-7.30 (1H, m), 7.36-7.41 (1H, m), 7.46-7.52 (3H, m), 7.56-7.84 (2H, m), 8.04-8.09 (1H, m), 8.45-8.50 (1H, m), 8.72-8.88 (1H, m), 8.93 (1H, s)

ESI-MS (m/e): 406 [M+H]$^+$

Example 78

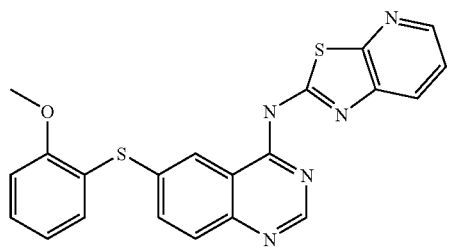

[6-(2-Methoxyphenylsulfanyl)-quinazolin-4-yl]-
thiazolo[5,4-b]pyridin-2-yl-amine The compound of Example 78 was manufactured by the same method as in Example 1, by a similar method thereto or by a combination of such a method with a conventional method using 2-methoxy-thiophenol, thiazole[5,4-b]pyridin-2-yl-amine and 4-chloro-6-iodoquinazoline.

$^1$HNMR (DMSO) δ3.83 (3H, s), 6.99-7.03 (1H, m), 7.19 (1H, d, J=8.0Hz), 7.26 (1H, d, J=8.0Hz), 7.40-7.44 (1H, m), 7.52-7.58 (1H, m), 7.68-7.74 (1H, m), 7.82-7.88 (1H, m), 8.06-8.12 (1H, m), 8.48-8.54 (1H, m), 8.72-8.78 (1H, m), 8.92-8.99 (1H, m)

ESI-MS (m/e): 418 [M+H]$^+$

Example 79

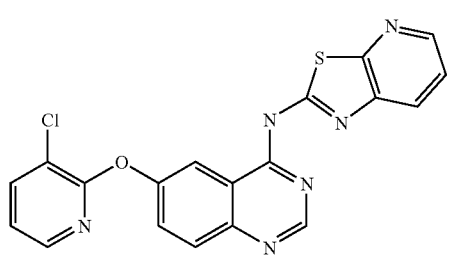

[6-(3-Chloropyridin-2-yloxy)-quinazolin-4-yl]-thia-
zolo[5,4-b]pyridin-2-yl-amine The compound of Example 79 was manufactured by the same method as in Example 95, by a similar method thereto or by a combination of such a method with a conventional method using 2,3-dichloropyridine, thiazolo[5,4-b]pyridin-2-yl-amine and 4-chloro-6-hydroxy-quinazoline.

$^1$HNMR (DMSO) δ7.30 (1H, dd, J=4.8, 7.6Hz), 7.54 (1H, dd, J=4.8, 7.6Hz), 7.91 (1H, dd, J=2.4, 8.8Hz), 8.01 (1H, d, J=8.8Hz), 8.08-8.10 (1H, m), 8.15-8.20 (2H, m), 8.51 (1H, dd, J=1.2, 4.8Hz), 8.55 (1H, s), 9.00 (1H, s)

ESI-MS (m/e): 407 [M+H]$^+$

Example 80

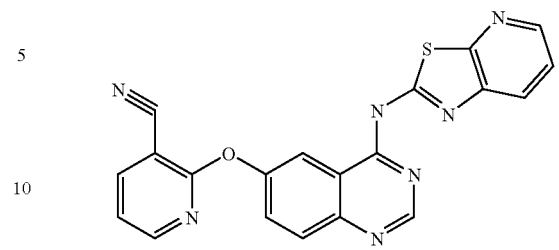

[6-(3-Cyanopyridin-2-yloxy)-quinazolin-4-yl]-thia-
zolo[5,4-b]pyridin-2-yl-amine The compound of Example 80 was manufactured by the same method as in Example 95, by a similar method thereto or by a combination of such a method with a conventional method using 3-cyano-2-chloropyridine, thiazolo[5,4-b]pyridin-2-yl-amine and 4-chloro-6-hydroxy-quinazoline.

$^1$HNMR (DMSO) δ7.41 (1H, dd, J=4.8, 7.6Hz), 7.52 (1H, dd, J=4.8, 8.4Hz), 7.94-8.02 (2H, m), 8.07-8.09 (1H, m), 8.44 (1H, dd, J=1.6, 4.8Hz), 8.48 (1H, dd, J=1.6, 4.8Hz), 8.52 (1H, dd, J=1.6, 7.6Hz), 8.64 (1H, s), 8.98 (1H, s)

ESI-MS (m/e): 398 [M+H]$^+$

Example 81

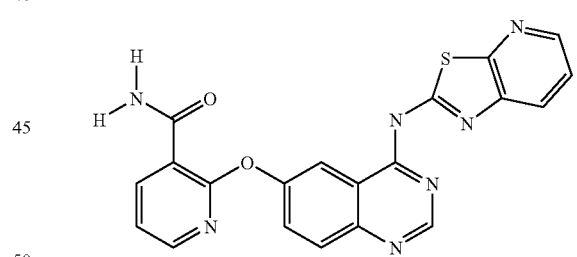

[6-(3-Carboxamidopyridin-2-yloxy)-quinazolin-4-
yl]-thiazolo[5,4-b]pyridin-2-yl-amine The compound of Example 81 was manufactured by the same method as in Example 95, by a similar method thereto or by a combination of such a method with a conventional method using 3-carbamoyl-2-chloropyridine, thiazolo[5,4-b]pyridin-2-yl-amine and 4-chloro-6-hydroxy-quinazoline.

$^1$HNMR (DMSO) δ7.30-7.33 (1H, m), 7.44-7.49 (1H, m), 7.80-7.87 (2H, m), 7.90-7.97 (2H, m), 7.99-8.04 (1H, m), 8.23-8.27 (2H, m), 8.40-8.44 (1H, m), 8.50-8.56 (1H, m), 8.84-8.90 (1H, m)

ESI-MS (m/e): 416 [M+H]$^+$

Example 82

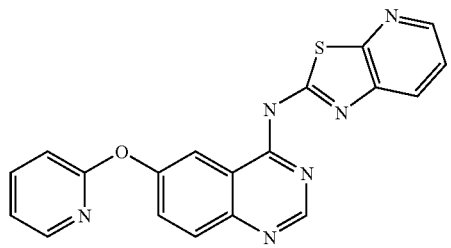

[6-(Pyridin-2-yloxy)-quinazolin-4-yl]-thiazolo-[5,4-b]pyridin-2-yl-amine

The compound of Example 82 was manufactured by the same method as in Example 95, by a similar method thereto or by a combination of such a method with a conventional method using 2-fluoropyridine, thiazolo[5,4-b]pyridin-2-yl-amine and 4-chloro-6-hydroxy-quinazoline.

$^1$HNMR (DMSO) δ7.24-7.27 (2H, m), 7.54 (1H, dd, J=4.8, 8.0Hz), 7.84 (1H, dd, J=2.4, 8.8Hz), 7.96-8.00 (2H, m), 8.07-8.09 (1H, m), 8.22-8.24 (1H, m), 8.50-8.51 (2H, m), 8.99 (1H, s)

ESI-MS (m/e): 373 [M+H]$^+$

Example 83

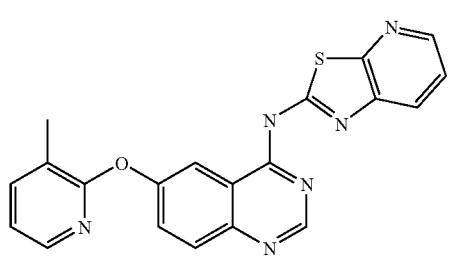

[6-(3-Methylpyridin-2-yloxy)-quinazolin-4-yl]-thiazolo-[5,4-b]pyridin-2-yl-amine The compound of Example 83 was manufactured by the same method as in Example 22, by a similar method thereto or by a combination of such a method with a conventional method using 2-chloro-3-methylpyridine, thiazolo[5,4-b]pyridin-2-yl-amine and 4-chloro-6-hydroxy-quinazoline.

$^1$HNMR (DMSO) δ2.45 (3H, s), 7.19-7.22 (1H, m), 7.59-7.62 (1H, m), 7.83-7.85 (1H, m), 7.93-7.95 (2H, m), 8.03-8.06 (2H, m), 8.34-8.35 (1H, m), 8.58-8.59 (1H, m), 9.10 (1H, s)

ESI-MS (m/e): 387 [M+H]$^+$

Example 84

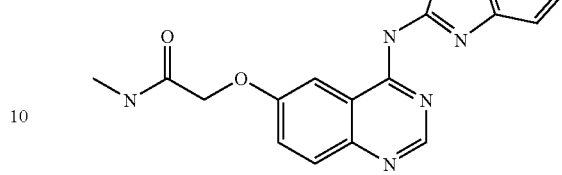

[6-(Methylcarbamoyl-methyloxy)-quinazolin-4-yl]-thiazolo-[5,4-b]pyridin-2-yl-amine The compound of Example 84 was manufactured by the same method as in Example 22, by a similar method thereto or by a combination of such a method with a conventional method using 2-hydroxy-N-methyl-acetamide, thiazolo[5,4-b]pyridin-2-yl-amine and 4-chloro-6-hydroxy-quinazoline.

$^1$HNMR (DMSO) δ2.73 (3H, d, J=4.4Hz), 4.72 (2H, s), 7.55 (1H, dd, J=4.8, 8.0Hz), 7.71-7.74 (1H, m), 7.93 (1H, d, J=8.8Hz), 8.12-8.13 (1H, m), 8.20-8.24 (1H, m), 8.50-8.51 (1H, m), 8.92 (1H, s)

ESI-MS (m/e): 367 [M+H]$^+$

Example 85

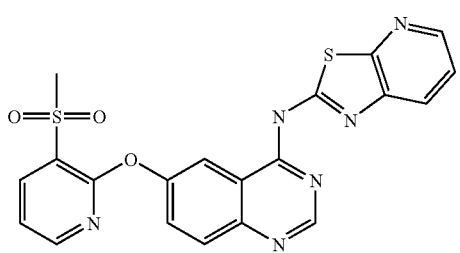

[6-(3-Methylsulfonylpyridin-2-yloxy)-quinazolin-4-yl]-thiazolo-[5,4-b]pyridin-2-yl-amine The compound of Example 85 was manufactured by the same method as in Example 95, by a similar method thereto or by a combination of such a method with a conventional method using 2-chloro-3-methylsulfonylpyridine.

$^1$HNMR (DMSO) δ3.55 (3H, s), 7.49-7.55 (2H, m), 7.96-8.10 (3H, m), 8.44 (1H, dd, J=2.0, 7.6Hz), 8.48-8.51 (2H, m), 8.64 (1H, s), 9.01 (1H, s)

ESI-MS (m/e): 451 [M+H]$^+$

Example 86

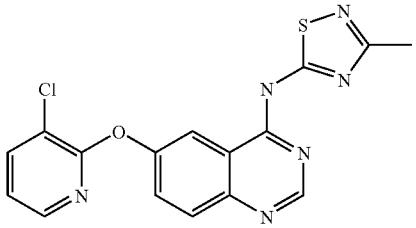

[6-(3-Chloropyridin-2-yloxy)-quinazolin-4-yl]-3-methyl-[1,2,4]thiadiazol-5-yl-amine The compound of Example 86 was manufactured by the same method as in Example 95, by a similar method thereto or by a combination of such a method with a conventional method using 2,3-dichloropyridine, 5-amino-3-methyl-[1,2,4]thiadiazole and 4-chloro-6-hydroxy-quinazoline.

$^1$HNMR (CDCl$_3$) δ2.58 (3H, s), 7.09-7.12 (1H, m), 7.76-7.78 (1H, m), 7.86-7.89 (1H, m), 8.04-8.08 (2H, m), 8.19 (1H, s), 8.98 (1H, s)

ESI-MS (m/e): 371 [M+H]$^+$

Example 87

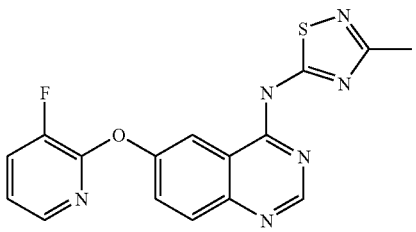

[6-(3-Fluoropyridin-2-yloxy)-quinazolin-4-yl]-3-methyl-[1,2,4]thiadiazol-5-yl-amine The compound of Example 87 was manufactured by the same method as in Example 95, by a similar method thereto or by a combination of such a method with a conventional method using 2-chloro-3-fluoropyridine, 5-amino-3-methyl-[1,2,4]-thiadiazole and 4-chloro-6-hydroxy-quinazoline.

$^1$HNMR (CDCl$_3$) δ2.56 (3H, s), 7.12-7.16 (1H, m), 7.57-7.62 (1H, m), 7.78 (1H, dd, J=2.4, 8.8Hz), 7.95-7.97 (1H, m), 8.09 (1H, d, J=8.8Hz), 8.17 (1H, d, J=2.4Hz), 8.99 (1H, s)

ESI-MS (m/e): 355 [M+H]$^+$

Example 88

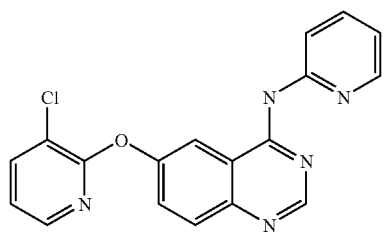

[6-(3-Chloropyridin-2-yloxy)-quinazolin-4-yl]-pyridin-2-yl-amine

The compound of Example 88 was manufactured by the same method as in Example 95, by a similar method thereto or by a combination of such a method with a conventional method using 2,3-dichloropyridine, 2-aminopyridine and 4-chloro-6-hydroxy-quinazoline.

$^1$HNMR (CDCl$_3$) δ: 7.07 (1H, dd, J=7.6, 4.9Hz), 7.25-7.25 (1H, m), 7.33-7.35 (1H, m), 7.49-7.52 (2H, m), 7.77 (1H, dd, J=9.2, 2.5Hz), 7.85 (1H, dd, J=7.6, 1.8Hz), 8.07-8.10 (2H, m), 8.16 (1H, d, J=2.5Hz), 8.78 (1H, s)

ESI-MS (m/e): 350 [M+H]$^+$

Example 89

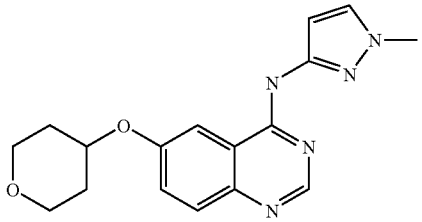

[6-(Tetrahydro-2H-pyran-4-yloxy)-quinazolin-4-yl]-(1-methyl-1H-pyrazol-3-yl)-amine The compound of Example 89 was manufactured by the same method as in Example 22, by a similar method thereto or by a combination of such a method with a conventional method using 4-hydroxy-tetrahydro-2H-furan, 3-amino-1-methyl-1H-pyrazole and 4-chloro-6-hydroxy-quinazoline.

$^1$HNMR (CDCl$_3$) δ: 1.79-1.82 (2H, m), 2.15-2.18 (2H, m), 3.73-3.75 (2H, m), 3.91 (3H, s), 3.97-4.03 (2H, m), 5.00-5.02 (1H, m), 6.91-6.93 (1H, m), 7.39-7.40 (1H, m), 7.52 (1H, dd, J=9.2, 2.5Hz), 8.02 (1H, d, J=9.2Hz), 8.25 (1H, s), 8.60 (1H, s)

ESI-MS (m/e): 326 [M+H]$^+$

Example 90

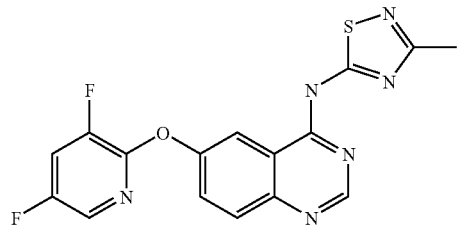

[6-(3,5-Difluoropyridin-2-yloxy)-quinazolin-4-yl]-3-methyl-[1,2,4]thiadiazol-5-yl-amine The compound of Example 90 was manufactured by the same method as in Example 95, by a similar method thereto or by a combination of such a method with a conventional method using 2,3,5-trifluoropyridine, 5-amino-3-methyl[1,2,4]thiadiazole and 4-chloro-6-hydroxy-quinazoline.

$^1$HNMR (CDCl$_3$) δ: 2.59 (3H, s), 7.47-7.49 (1H, m), 7.77 (1H, dd, J=9.0, 2.5Hz), 7.90 (1H, d, J=2.5Hz), 8.09 (1H, d, J=9.0Hz), 8.16 (1H, d, J=2.5Hz), 9.00 (1H, s)

ESI-MS (m/e): 373 [M+H]$^+$

Example 91

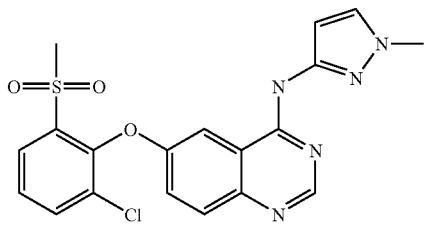

[6-(2-Chloro-6-(methylsulfonyl)phenoxy)-quinazolin-4-yl]-(1-methyl-1H-pyrazol-3-yl)-amine The compound of Example 91 was manufactured by the same method as in Example 95, by a similar method thereto or by a combination of such a method with a conventional method using 1,2-dichloro-3-methylsulfonylbenzene, 3-amino-1-methyl-1H-pyrazole and 4-chloro-6-hydroxyquinazoline.

$^1$HNMR (CDCl$_3$) δ: 3.31 (3H, s), 3.84 (3H, s), 6.78 (1H, d, J=2.2Hz), 7.31 (1H, d, J=2.2Hz), 7.45-7.55 (2H, m), 7.79 (2H, dd, J=8.0, 1.7Hz), 7.95 (1H, d, J=9.0Hz), 8.08 (1H, dd, J=8.0, 1.7Hz), 8.63 (1H, s)
ESI-MS (m/e): 430 [M+H]$^+$

Example 92

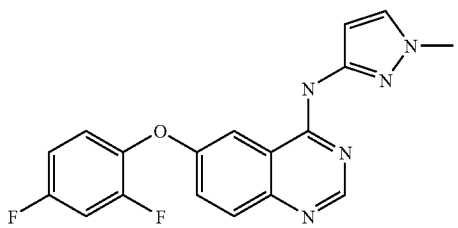

[6-(2,4-Difluorophenoxy)-quinazolin-4-yl]-(1-methyl-1H-pyrazol-3-yl)-amine

The compound of Example 92 was manufactured by the same method as in Example 95, by a similar method thereto or by a combination of such a method with a conventional method using 1,2,4-trifluorobenzene, 3-amino-1-methyl-1H-pyrazole and 4-chloro-6-hydroxy-quinazoline.

$^1$HNMR (CDCl$_3$) δ: 3.86 (3H, s), 6.86-7.00 (3H, m), 7.19-7.34 (2H, m), 7.57-7.7.95 (3H, m), 8.77 (1H, s)
ESI-MS (m/e): 354 [M+H]$^+$

Example 93

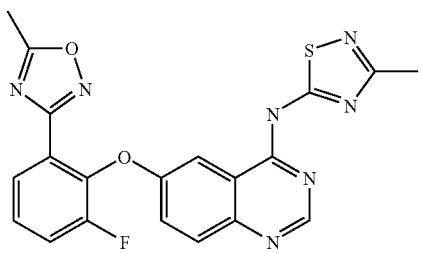

[6-(2-Fluoro-6-(5-methyl-[1,2,4]oxadiazol-3-yl)-phenoxy)-quinazolin-4-yl]-3-methyl-[1,2,4]thiadiazol-5-yl-amine The compound of Example 93 was manufactured by the same method as in Example 95, by a similar method thereto or by a combination of such a method with a conventional method using 3-(2,3-difluorophenyl)-5-methyl-1,2,4-oxadiazole, 5-amino-3-methyl-[1,2,4]thiadiazole and 4-chloro-6-hydroxy-quinazoline.

$^1$HNMR (DMSO-d6) δ: 1.63 (3H, s), 1.69 (3H, s), 6.68-6.70 (2H, m), 6.91 (1H, dd, J=9.0, 2.7Hz), 6.98-7.00 (1H, m), 7.07-7.09 (1H, m), 7.14-7.15 (1H, m), 7.99 (1H, s)
ESI-MS (m/e): 436 [M+H]$^+$

Example 94

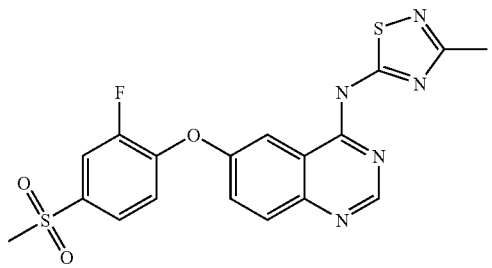

[6-(2-Fluoro-4-(methylsulfonylphenoxy-quinazolin-4-yl]-3-methyl-[1,2,4]thiadiazol-5-yl-amine The compound of Example 94 was manufactured by the same method as in Example 95, by a similar method thereto or by a combination of such a method with a conventional method using 1,2-difluoro-4-methanesulfonylbenzene, 5-amino-3-methyl-[1,2,4]thiadiazole and 4-chloro-6-hydroxy-quinazoline.

$^1$HNMR (CDCl$_3$) δ: 2.57 (3H, s), 3.16 (3H, s), 7.33-7.35 (1H, m), 7.72 (1H, dd, J=9.0, 2.7Hz), 7.81-7.83 (1H, m), 7.88-7.91 (2H, m), 8.10 (1H, d, J=9.0Hz), 9.00 (1H, s)
ESI-MS (m/e): 432 [M+H]$^+$

Example 95

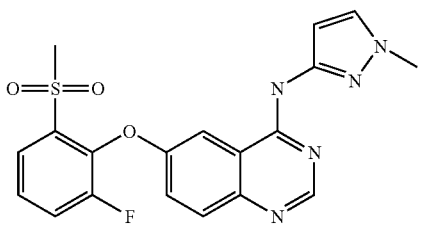

[6-(2-Fluoro-4-(methylsulfonyl)phenoxy)-quinazolin-4-yl]-(1-methyl-1H-pyrazol-3-yl)-amine 1,2-Difluoro-3-iodobenzene (1.70 g; 7.08 mmol), 2.17 g (21.2 mmol) of sodium methanesulfonate and 4.03 g (21.2 mmol) of copper iodide were heated with stirring at 111° C. for 20 hours in 50 ml of N,N-dimethylacetamide. The reaction solution was filtered, chloroform was added to the filtrate and the mixture was washed with a saturated aqueous solution of sodium hydrogen carbonate. The organic layer was dried and concentrated and the resulting residue was purified by a silica gel column chromatography (hexane:ethyl acetate=2:1) to give 987 mg (yield: 72%) of 1,2-difluoro-3-methanesulfonylbenzene as a colorless transparent solution.

4-[(1-Methyl-1H-pyrazol-3-yl)amino]quinazolin-6-ol (250 mg; 1.033 mmol) and 424 mg (2.219 mmol) of the above-prepared sulfone compound were added to a solution of 320 mg (2.857 mmol) of tert-butoxy potassium in 24 ml of N,N-dimethylacetamide and the mixture was stirred at 77° C. for 12 hours. To the reaction solution was added water followed by extracting with chloroform. The organic layer was dried and concentrated and the resulting residue was purified by a reversed phase preparative HPLC (0.1% TFA-containing water:acetonitrile=90:10→10:90) to give 120 mg (yield: 28%) of the title compound as a yellow solid.

$^1$HNMR (CDCl$_3$) δ: 3.32 (3H, s), 3.85 (3H, s), 6.87 (1H, d, J=2.3Hz), 7.36 (1H, d, J=2.3Hz), 7.51-7.54 (2H, m), 7.71 (1H, dd, J=9.0, 2.7Hz), 7.82 (1H, d, J=2.7Hz), 7.93-7.95 (1H, m), 8.12 (1H, d, J=9.0Hz), 8.76 (1H, s)

ESI-MS (m/e): 414 [M+H]$^+$

Example 96

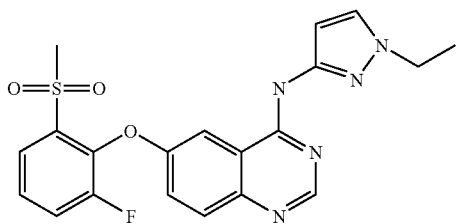

[6-(2-Fluoro-6-(methylsulfonyl)phenoxy)-quinazolin-4-yl]-(1-ethyl-1H-pyrazol-3-yl)-amine The compound of Example 96 was manufactured by the same method as in Example 95, by a similar method thereto or by a combination of such a method with a conventional method using 1,2-difluoro-3-methanesulfonylbenzene, 3-amino-1-ethyl-1H-pyrazole and 4-chloro-6-hydroxy-quinazoline.

$^1$HNMR (CDCl$_3$) δ: 1.48 (3H, t, J=7.4Hz), 3.30 (3H, s), 4.12 (2H, q, J=7.4Hz), 6.82 (1H, d, J=2.3Hz), 7.37 (1H, d, J=2.3Hz), 7.49-7.57 (3H, m), 7.85-7.95 (3H, m), 8.58 (1H, s)

ESI-MS (m/e): 428 [M+H]$^+$

Example 97

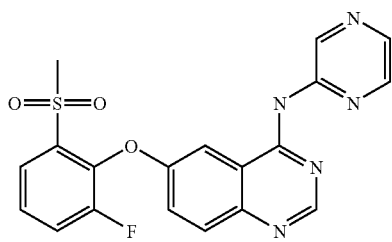

[6-(2-Fluoro-6-(methylsulfonyl)phenoxy)-quinazolin-4-yl]-pyrazin-2-yl-amine

The compound of Example 97 was manufactured by the same method as in Example 95, by a similar method thereto or by a combination of such a method with a conventional method using 1,2-difluoro-3-methanesulfonylbenzene, 2-aminopyrazine and 4-chloro-6-hydroxy-quinazoline.

$^1$HNMR (CDCl$_3$) δ: 3.31 (3H, s), 7.48-7.53 (3H, m), 7.85-7.96 (3H, m), 8.31-8.34 (2H, m), 8.57 (1H, s), 9.31 (1H, s)

ESI-MS (m/e): 412 [M+H]$^+$

Example 98

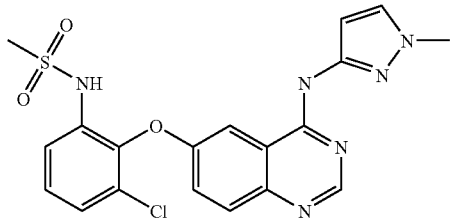

[6-(2-Chloro-6-(methylsulfonylamino)phenoxy)-quinazolin-4-yl]-(1-methyl-1H-pyrazol-3-yl)-amine The compound of Example 98 was manufactured by the same method as in Example 95, by a similar method thereto or by a combination of such a method with a conventional method using N-(3-chloro-2-fluorophenyl)methanesulfonamide, 3-amino-1-methyl-1H-pyrazole and 4-chloro-6-hydroxy-quinazoline.

$^1$HNMR (DMSO-d6) δ: 2.95 (3H, s), 3.82 (3H, s), 6.74 (1H, s), 7.40-7.42 (1H, m), 7.47-7.49 (1H, m), 7.60 (1H, d, J=8.3Hz), 7.70-7.72 (2H, m), 7.87 (1H, d, J=8.3Hz), 7.96 (1H, s), 8.79 (1H, s), 9.71 (1H, s)

ESI-MS (m/e): 445 [M+H]$^+$

Example 99

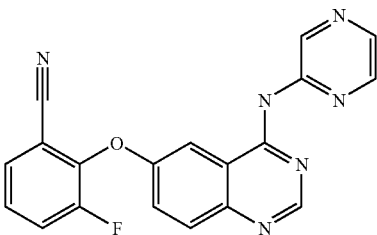

3-Fluoro-2-({4-[(pyrazin-2-yl)amino]quinazolin-6-yl}-oxy)benzonitrile

2-Aminopyrazine (2.20 g; 23.7 mmol), 0.49 g (0.8 mmol) of 2,2-bisdiphenylphosphino-1,1-binaphthyl, 10.2 g (31.5 mmol) of cesium carbonate and 0.82 g (0.8 mmol) of tris-dibenzylidene acetone palladium were added to a solution of 3.50 g (15.8 mmol) of 4-chloro-6-acetate-quinazoline in 180 ml of toluene and the mixture was stirred at 111° C. for 20 hours. The reaction solution was filtered, water was added to the filtrate and the mixture was extracted with chloroform. The organic layer was dried and concentrated, 100 ml of tetrahydrofuran and 100 ml of methanol were added to the residue, then 10 ml of aqueous ammonia was added to the resulting solution and the mixture was stirred for 30 minutes. The reaction solution was concentrated, the resulting residue was stirred with ethyl acetate, the resulting solution was filtered and the residue was dried to give 1.63 g (yield: 43%) of 6-hydroxy-(pyrazin-2-yl)quinazolin-4-yl-amine as a yellow solid.

The resulting hydroxyl compound (60 mg; 0.25 mmol) and 105 mg (0.75 mmol) of 1,2-difluoro-benzonitrile were added to a solution of 89 mg (0.75 mmol) of tert-butoxy potassium in 3 ml of N,N-dimethylacetamide and the mixture was stirred at room temperature for 45 minutes. Water was added to the reaction solution and the mixture was extracted with chloroform. The organic layer was dried and concentrated and the resulting residue was purified by a thin layer silica gel chromatography (chloroform:methanol=9:1) to give 36 mg (yield: 40%) of the title compound as a yellow solid.

$^1$HNMR (DMSO-d6) δ: 7.57-7.59 (1H, m), 7.87-7.92 (4H, m), 8.09-8.12 (1H, m), 8.34-8.37 (1H, m), 8.43-8.43 (1H, m), 8.70-8.72 (1H, m), 9.55 (1H, s), 10.64 (1H, s)

ESI-MS (m/e): 359 [M+H]$^+$

Example 100

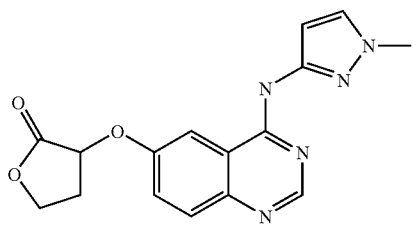

[6-(Butyrolactone-2-yloxy-quinazolin-4-yl]-(1-methyl-1H-pyrazol-3-yl)-amine

4-Chloro-6-hydroxy-quinazoline (77 mg; 0.43 mmol), 131 mg (1.28 mmol) of 2-hydroxy-butyrolactone and 336 mg (1.28 mmol) of triphenyl phosphine were dissolved in 7 ml of THF and 558 mg (1.28 mmol) of diethyl azodicarboxylate was added thereto at room temperature. The reaction solution was further stirred at room temperature for 10 hours, water was added thereto and the mixture was extracted with chloroform. The organic layer was dried and concentrated and the resulting residue was purified by a silica gel column chromatography (hexane:ethyl acetate=1:1) to give 4-chloro-6-(butyrolactone-2-yloxy)-quinazoline.

The resulting chloro compound was heated to stir at 140° C. for 30 minutes with 60 mg (0.147 mmol) of 1-methyl-1H-pyrazole-3-amine in 0.2 ml of phenol. Chloroform was added to the reaction solution and the mixture was washed with a saturated aqueous solution of sodium hydrogen carbonate. The organic layer was dried and concentrated and the resulting residue was purified by a reversed phase preparative HPLC (0.1% TFA-containing water:acetonitrile=90:10→10:90) to give 1 mg (yield: 1%) of the title compound as a yellow solid.

$^1$HNMR (CDCl$_3$) δ: 2.39-2.44 (1H, m), 2.95-2.96 (1H, m), 3.89 (3H, s), 4.39-4.46 (1H, m), 4.51-4.53 (1H, m), 5.35-5.38 (1H, m), 6.73-6.75 (1H, m), 7.32-7.33 (1H, m), 7.52-7.53 (1H, m), 7.85 (1H, d, J=8.6Hz), 8.17 (1H, s), 8.51 (1H, s)

ESI-MS (m/e): 326 [M+H]$^+$

Example 101

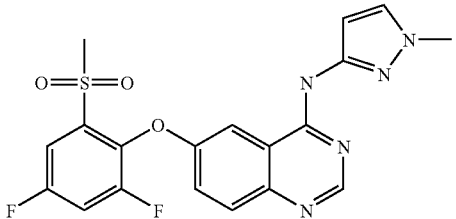

[6-(2,4-Difluoro-6-(methylsulfonyl)phenoxy)-quinazolin-4-yl]-(1-methyl-1H-pyrazol-3-yl)-amine The compound of Example 101 was manufactured by the same method as in Example 95, by a similar method thereto or by a combination of such a method with a conventional method using 1,2,5-trifluoro-6-(methanesulfonyl)benzene, 3-amino-1-methyl-1H-pyrazole and 4-chloro-6-hydroxy-quinazoline.

$^1$HNMR (DMSO-d6) δ: 3.69 (3H, s), 4.09 (3H, s), 7.02 (1H, d, J=2.0Hz), 7.97-7.99 (2H, m), 8.15-8.17 (2H, m), 8.33-8.36 (2H, m), 9.08 (1H, s)

ESI-MS (m/e): 432 [M+H]$^+$

Example 102

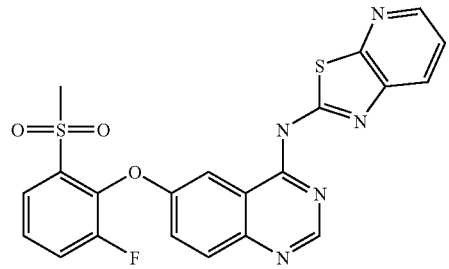

[6-(2-Fluoro-6-(methylsulfonyl)phenoxy)-quinazolin-4-yl]-thiazolo[5,4-b]pyridin-2-yl-amine (6-Hydroxy-quinazolin-4-yl)-thiazolo[5,4-b]pyridin-2-yl-amine (100 mg; 0.34 mmol) and 116 mg (0.61 mmol) of 1,2-difluoro-3-methanesulfonylbenzene were added to a solution of 120 mg (0.61 mmol) of tert-buxoty potassium in 5 ml of N,N-dimethylacetamide and the mixture was stirred at room temperature for 1 hour. Water was added to the reaction solution and the mixture was extracted with chloroform. The organic layer was dried and concentrated and the resulting residue was purified by a thin layer silica gel chromatography (chloroform:methanol=10:1) to give 81 mg (yield: 51%) of the title compound as a yellow solid.

$^1$HNMR (DMSO-d6) δ: 3.41 (3H, s), 7.47-7.48 (1H, m), 7.67-7.69 (1H, m), 7.83-7.85 (1H, m), 7.92-7.97 (5H, m), 8.43-8.44 (1H, m), 8.87 (1H, s)

ESI-MS (m/e): 468 [M+H]$^+$

Example 103

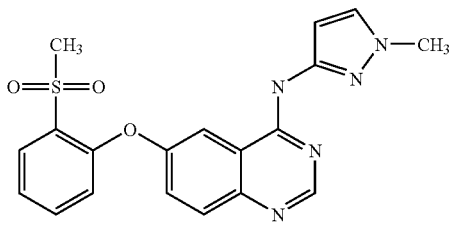

N-(1-Methyl-1H-pyrazol-3-yl)-6-[2-(methylsulfonyl)-phenoxy]quinazolin-4-yl-amine The compound of Example 103 was manufactured by the same method as in Example 95, by a similar method thereto or by a combination of such a method with a conventional method using 2-methylsulfonylfluorobenzene.

$^1$HNMR (CD$_3$OD) δ: 3.39 (3H, s), 3.87 (3H, s), 6.70 (1H, s), 7.15 (1H, d, J=8.2Hz), 7.41 (1H, t, J=7.6Hz), 7.56 (1H, d, J=2.0Hz), 7.69-7.73 (2H, m), 7.88 (1H, d, J=9.0Hz), 8.07-8.10 (1H, m), 8.12 (1H, d, J=2.0Hz), 8.54 (1H, s)

ESI-MS (m/e): 396 [M+H]

Example 104

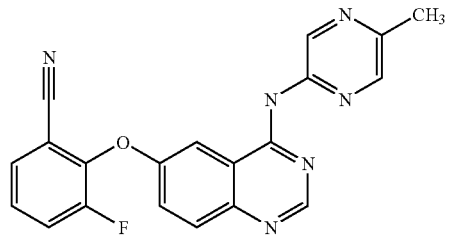

3-Fluoro-2-({4-[(5-methylpyrazin-2-yl)amino]-quinazolin-6-yl}oxy)benzonitrile

The compound of Example 157 was manufactured by the same method as in Example 95, by a similar method thereto or by a combination of such a method with a conventional method using 2,3-difluorobenzonitrile, 2-amino-5-methylpiperazine and 4-chloro-6-hydroxy-quinazoline.

$^1$HNMR (DMSO-d6) δ: 2.49 (3H, s), 7.59-7.61 (1H, m), 7.87-7.97 (4H, m), 8.15 (1H, d, J=2.4Hz), 8.37-8.40 (1H, m), 8.76-8.79 (1H, m), 9.28 (1H, s)

ESI-MS (m/e): 373 [M+H]$^+$

Example 105

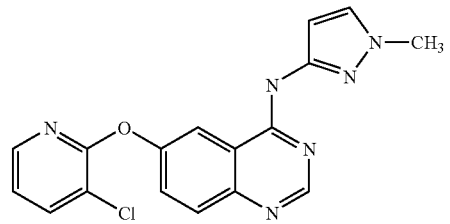

6-(3-Chloropyridin-2-ylsulfanyl)(1-methylpyrazol-3-yl)quinazolin-4-yl-amine

4-[(1-Methyl-1H-pyrazol-3-yl)amino]quinazolin-6-ol (80 mg; 0.332 mmol) and 147 mg (0.993 mmol) of 2-fluoro-3-methylbenzonitrile were added to a solution of 33 mg (1.375 mmol) of sodium hydride (containing 60%) in 7 ml of N,N-dimethylacetamide and the mixture was stirred at 130° C. for 3 hours. Water was added to the reaction solution and the mixture was extracted with chloroform. The organic layer was dried and concentrated and the resulting residue was purified by a silica gel chromatography (chloroform:methanol=9:1) to give 60 mg (yield: 51%) of the title compound as a colorless solid.

$^1$HNMR (CD$_3$OD) δ: 3.88 (3H, s), 6.79 (1H, m), 7.09-7.12 (1H, m), 7.44 (1H, d, J=2.4Hz), 7.64 (1H, dd, J=8.8, 2.4Hz), 7.86-7.90 (2H, m), 8.04 (1H, dd, J=4.8, 1.6Hz), 8.07 (1H, d, J=2.0Hz), 8.59 (1H, brs)

ESI-MS (m/e): 353 [M+H]$^+$

Example 106

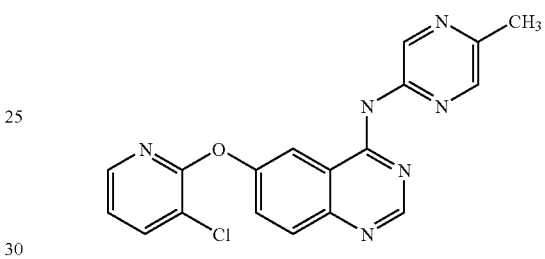

6-(3-Chloropyridin-2-yl)sulfanyl-(5-methyl-pyrazin-2-yl)quinazolin-4-yl-amine

The compound of Example 106 was manufactured by the same method as in Example 95, by a similar method thereto or by a combination of such a method with a conventional method using 2,3-difluoropyridine, 2-amino-5-methylpiperazine and 4-chloro-6-hydroxy-quinazoline.

$^1$HNMR (CD$_3$OD) δ: 2.58 (3H, s), 7.11-7.15 (1H, m), 7.43 (1H, d, J=2.0Hz), 7.69 (1H, dd, J=8.0, 1.6Hz), 7.73 (1H, dd, J=8.8, 2.4Hz), 7.91 (1H, dd, J=8.0, 1.6Hz), 7.97 (1H, d, J=8.8Hz), 8.05 (1H, dd, J=4.8, 2.0Hz), 8.16 (1H, d, J=2.4Hz), 8.27 (1H, s), 9.72 (1H, s)

ESI-MS (m/e): 365 [M+H]$^+$

Example 107

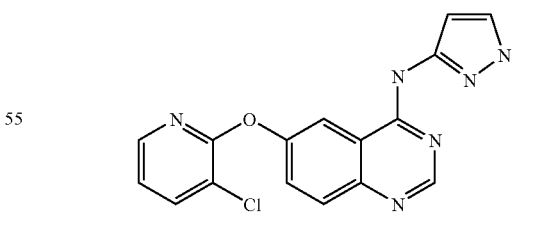

6-(3-Chloropyridin-2-yl)sulfanyl-(1H-pyrazol-3-yl)-quinazolin-4-yl-amine

The compound of Example 107 was manufactured by the same method as in Example 95, by a similar method thereto or by a combination of such a method with a conventional method using 2,3-dichloropyridine, 2-amino-1H-pyrazole and 4-chloro-6-hydroxy-quinazoline.

$^1$HNMR (CD$_3$OD) δ: 7.12-7.16 (1H, m), 7.59 (1H, brs), 7.67 (1H, d, J=8.8Hz), 7.87 (1H, d, J=8.8Hz), 7.94 (1H, dd, J=8.0, 1.6Hz), 8.03 (1H, dd, J=4.8, 1.6Hz), 8.16 (1H, d, J=2.0Hz), 8.62 (1H, brs)

ESI-MS (m/e): 339 [M+H]$^+$

Example 108

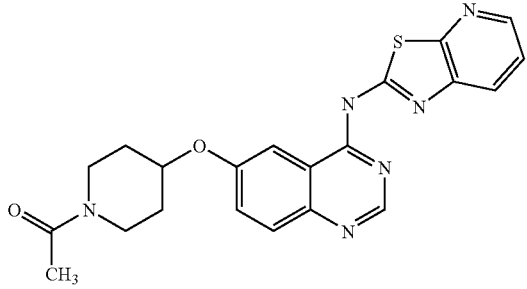

6-(Acetylpiperidin-4-yl)oxy-N-[1,3]thiazolo[5,4-d]-pyridin-2-ylquinazolin-4-yl-amine The compound of Example 108 was manufactured by the same method as in Example 22, by a similar method thereto or by a combination of such a method with a conventional method using 4-hydroxy-1-acetylpiperidine, thiazole[5,4-b]pyridin-2-yl-amine and 4-chloro-6-hydroxyquinazoline.

$^1$HNMR (CD$_3$OD) δ: 1.87-1.98 (2H, m), 2.05-2.19 (2H, m), 3.54-3.69 (2H, m), 3.79-4.68 (2H, m), 4.87-4.91 (1H, m), 7.41-7.44 (1H, m), 7.51 (1H, d, J=8.0Hz), 7.78 (1H, d, J=8.0Hz), 7.97 (1H, d, J=2.4Hz), 8.03 (1H, d, J=7.2Hz), 8.39 (1H, dd, J=4.8, 1.2Hz), 8.66 (1H, brs)

ESI-MS (m/e): 421 [M+H]$^+$

Example 109

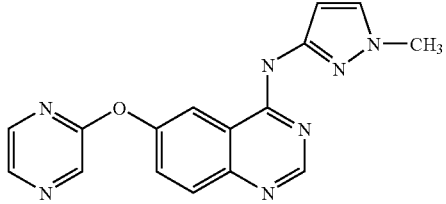

N-(1-Methyl-1H-pyrazol-3-yl)-6-(pyrazin-2-yloxy)-quinazolin-4-yl-amine

The compound of Example 109 was manufactured by the same method as in Example 95, by a similar method thereto or by a combination of such a method with a conventional method using 2-chloropyrazine, 3-amino-1-methyl-1H-pyrazole and 4-chloro-6-hydroxyquinazoline.

$^1$HNMR (CD$_3$OD) δ: 3.88 (3H, s), 6.83 (1H, d, J=2.4Hz), 7.46 (1H, d, J=2.4Hz), 7.67 (1H, dd, J=8.8, 2.4Hz), 7.91 (1H, d, J=8.8Hz), 8.13 (1H, d, J=2.4Hz), 8.17-8.18 (1H, m), 8.34 (1H, d, J=2.8Hz), 8.53 (1H, d, J=1.2Hz), 8.65 (1H, s)

ESI-MS (m/e): 320 [M+H]$^+$

Example 110

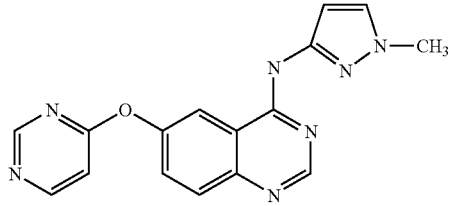

N-(1-Methyl-1H-pyrazol-3-yl)-6-(pyrimidin-4-yloxy)-quinazolin-4-yl-amine

The compound of Example 110 was manufactured by the same method as in Example 95, by a similar method thereto or by a combination of such a method with a conventional method using 2-chloropyrimidine, 3-amino-1-methyl-1H-pyrazole and 4-chloro-6-hydroxyquinazoline.

$^1$HNMR (CD$_3$OD) δ: 3.88 (3H, s), 6.83 (1H, brs), 7.15 (1H, d, J=5.2Hz), 7.46 (1H, brs), 7.66 (1H, d, J=8.8Hz), 7.92 (1H, d, J=8.8Hz), 8.16 (1H, d, J=2.4Hz), 8.64-8.66 (2H, m), 8.75 (1H, s)

ESI-MS (m/e): 320 [M+H]$^+$

Example 111

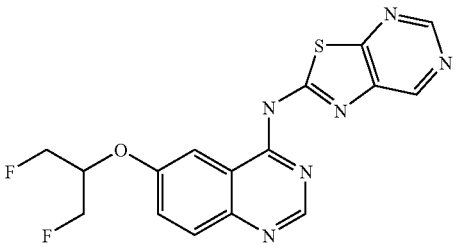

6-[2-Fluoro-1-(fluoromethyl)ethoxy]-N-[1,3-thiazolo-[5,4-d]pyrimidin-2-ylquinazolin-4-yl-amine The compound of Example 111 was manufactured by the same method as in Example 22, by a similar method thereto or by a combination of such a method with a conventional method using 2-fluoro-1-(fluoromethyl)ethanol, thiazole[5,4-b]pyridin-2-yl-amine and 4-chloro-6-hydroxyquinazoline.

$^1$HNMR (CD$_3$OD) δ: 4.71-4.82 (2H, m), 4.83-4.91 (2H, m), 5.05-5.14 (1H, m), 7.61-7.64 (1H, m), 7.07-7.10 (1H, m), 7.83 (1H, brs), 8.13 (1H, d, J=2.4Hz), 8.80 (1H, brs), 8.94 (1H, s), 9.04 (1H, s)

ESI-MS (m/e): 375 [M+H]$^+$

Example 112

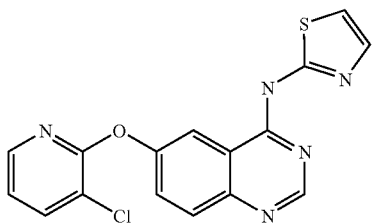

6-[(3-Chloropyridin-2-yl)oxy]-N-1,3-thiazol-2-yl-quinazolin-4-amine(1-methylpyrazol-3-yl)quinazolin-4-yl-amine The compound of Example 112 was manufactured by the same method as in Example 95, by a similar method thereto or by a combination of such a method with a conventional method using 2,3-dichloropyridine, 2-amino-thiazole and 4-chloro-6-hydroxyquinazoline.

$^1$HNMR (CD$_3$OD) δ: 7.08-7.13 (3H, m), 7.50 (1H, d, J=2.8Hz), 7.69-7.74 (1H, m), 7.90 (1H, dd, J=6.0, 2.0Hz), 7.91-7.94 (1H, m), 8.05 (1H, dd, J=4.8, 2.0Hz), 8.22 (1H, d, J=2.8Hz)

ESI-MS (m/e): 356 [M+H]$^+$

Example 114

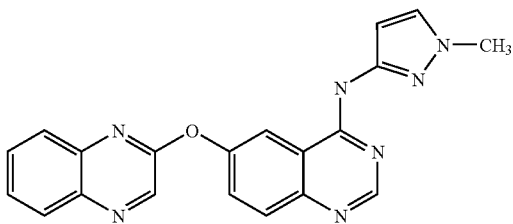

N-(1-Methyl-1H-pyrazol-3-yl)-6-(quinazolin-2-yloxy)-quinazolin-4-yl-amine

The compound of Example 114 was manufactured by the same method as in Example 95, by a similar method thereto or by a combination of such a method with a conventional method using 2-chloroquinazoline, 2-amino-1-methyl-1H-pyrazole and 4-chloro-6-hydroxy-quinazoline.

$^1$HNMR (CD$_3$OD) δ: 3.86 (3H, s), 6.82 (1H, brs), 7.45 (1H, d, J=2.4Hz), 7.57-7.79 (3H, m), 7.90-7.95 (1H, m), 8.06-8.09 (1H, m), 8.24 (1H, d, J=2.4Hz), 8.65 (1H, brs), 8.78 (1H, s)

ESI-MS (m/e): 370 [M+H]$^+$

Example 113

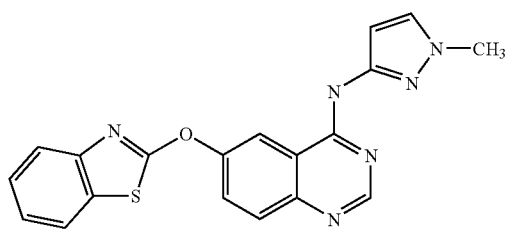

6-(1,3-Benzothiazol-2-yloxy)-N-(1-methyl-1H-pyrazol-3-yl)quinazolin-4-yl-amine

The compound of Example 113 was manufactured by the same method as in Example 95, by a similar method thereto or by a combination of such a method with a conventional method using 2-chloro-1,3-benzothiazole, 2-amino-1-methyl-1H-pyrazole and 4-chloro-6-hydroxyquinazoline.

$^1$HNMR (CD$_3$OD) δ: 3.87 (3H, s), 6.86 (1H, d, J=2.4Hz), 7.34 (1H, t, J=8.4Hz), 7.41-7.46 (2H, m), 7.74 (1H, t, J=8.4Hz), 7.84 (1H, dd, J=8.8, 2.8Hz), 7.95 (1H, d, J=8.8Hz), 8.33 (1H, d, J=2.8Hz), 8.68 (1H, s)

ESI-MS (m/e): 375 [M+H]$^+$

Example 115

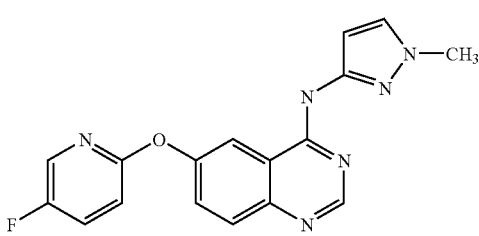

6-[(5-Fluoropyridin-2-yl)oxy]-N-(1-methyl-1H-pyrazol-3-yl)quinazolin-4-yl-amine

The compound of Example 115 was manufactured by the same method as in Example 95, by a similar method thereto or by a combination of such a method with a conventional method using 2,5-difluoropyridine, 3-amino-1-methyl-pyrazole and 4-chloro-6-hydroxy-quinazoline.

$^1$HNMR (CD$_3$OD) δ: 3.88 (3H, s), 6.78 (1H, d, J=2.4Hz), 7.10 (1H, dd, J=8.8, 2.8Hz), 7.48 (1H, d, J=2.4Hz), 7.62-7.66 (2H, m), 7.86 (1H, d, J=8.8Hz), 8.03 (1H, d, J=2.8Hz), 8.06 (1H, d, J=2.4Hz), 8.61 (1H, s)

ESI-MS (m/e): 337 [M+H]$^+$

Example 116

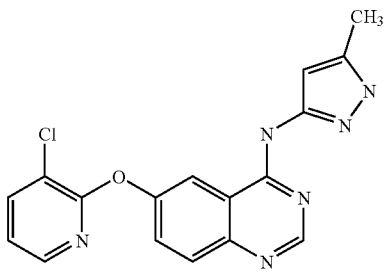

6-[(3-Chloropyridin-2-yl)oxy]-N-(5-methyl-1H-pyrazol-3-yl)quinazolin-4-yl-amine

The compound of Example 116 was manufactured by the same method as in Example 95, by a similar method thereto or by a combination of such a method with a conventional method using 2,3-dichloropyridine, 3-amino-5-methyl-1H-pyrazole and 4-chloro-6-hydroxy-quinazoline.

$^1$HNMR (CD$_3$OD) δ: 2.33 (3H, s), 7.09-7.12 (1H, m), 7.66 (1H, dd, J=8.8, 2.4Hz), 7.90 (1H, d, J=8.8Hz), 8.04 (1H, dd, J=5.2, 2.0Hz), 8.11 (1H, d, J=2.4Hz), 8.66 (1H, s)

ESI-MS (m/e): 353 [M+H]$^+$

Example 117

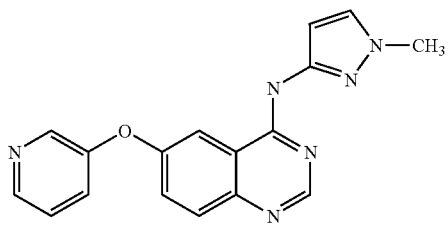

N-(1-Methyl-1H-pyrazol-3-yl)-6-(pyridin-3-yloxy)-quinazolin-4-yl-amine

The compound of Example 117 was manufactured by the same method as in Example 95, by a similar method thereto or by a combination of such a method with a conventional method using 3-fluoropyridine, 3-amino-1-methyl-1H-pyrazole and 4-chloro-6-hydroxy-quinazoline.

$^1$HNMR (CD$_3$OD) δ: 3.87 (3H, s), 6.85 (1H, d, J=2.4Hz), 7.42-7.47 (3H, m), 7.58 (1H, dd, J=8.8, 2.8Hz), 7.87-7.90 (2H, m), 8.39 (1H, dd, J=4.4, 1.2Hz), 8.43 (1H, d, J=2.8Hz), 8.64 (1H, s)

ESI-MS (m/e): 319 [M+H]$^+$

Example 118

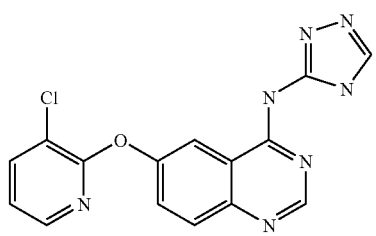

6-[(3-Chloropyridin-2-yl)oxy]-N-4H-[1,2,4]triazol-3-ylquinazolin-4-yl-amine

The compound of Example 118 was manufactured by the same method as in Example 95, by a similar method thereto or by a combination of such a method with a conventional method using 2,3-dichloropyridine, 3-amino-4H-[1,2,4]triazole and 4-chloro-6-hydroxy-quinazoline.

$^1$HNMR (CD$_3$OD) δ: 7.10-7.13 (1H, m), 7.69 (2H, br), 7.88 (2H, br), 7.90 (1H, dd, J=7.6, 1.6Hz), 8.05 (1H, dd, J=4.8, 1.6Hz), 8.22 (1H, d, J=2.4Hz)

ESI-MS (m/e): 340 [M+H]$^+$

Example 119

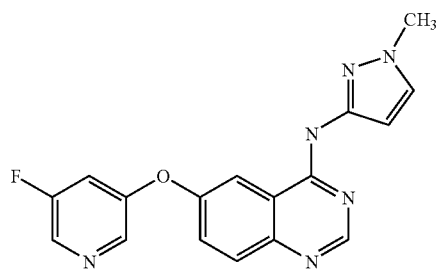

6-[(5-Fluoropyridin-3-yl)oxy]-N-(1-methyl-1H-pyrazol-3-yl)quinazolin-4-yl-amine

The compound of Example 119 was manufactured by the same method as in Example 95, by a similar method thereto or by a combination of such a method with a conventional method using 3,5-difluoropyridine, 3-amino-1-methyl-1H-pyrazole and 4-chloro-6-hydroxy-quinazoline.

$^1$HNMR (CD$_3$OD) δ: 3.87 (1H, s), 6.74 (1H, d, J=2.4Hz), 7.32-7.36 (1H, m), 7.51 (1H, d, J=2.0Hz), 7.66 (1H, dd, J=8.8, 2.4Hz), 7.90 (1H, d, J=8.8Hz), 8.05 (1H, d, J=2.4Hz), 8.29-8.30 (2H, m), 8.59 (1H, s)

ESI-MS (m/e): 337 [M+H]$^+$

Example 120

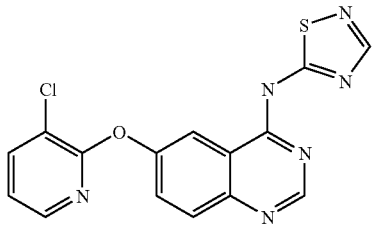

6-[(3-Chloropyridin-2-yl)oxy]-N-[1,2,4]-thiadiazol-5-ylquinazolin-4-yl-amine

The compound of Example 120 was manufactured by the same method as in Example 95, by a similar method thereto or by a combination of such a method with a conventional method using 2,3-dichloropyridine, 3-amino-[1,2,4]thiadiazole and 4-chloro-6-hydroxy-quinazoline.

$^1$HNMR (CD$_3$OD) δ: 7.14-7.18 (1H, m), 7.74-7.77 (1H, m), 7.93-7.96 (1H, m), 8.00 (1H, d, J=8.4Hz), 8.05-8.06 (1H, m), 8.33-8.34 (1H, m), 8.36 (1H, d, J=1.6Hz), 8.91 (1H, d, J=1.2Hz)

ESI-MS (m/e): 357 [M+H]$^+$

Example 122

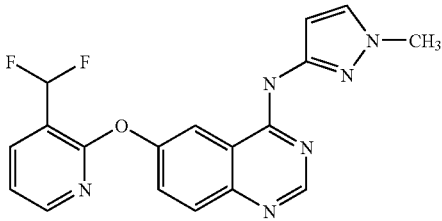

6-{[3-(Difluoromethyl)pyridin-2-yl]oxy}-N-(1-methyl-1H-pyrazol-3-yl)quinazolin-4-yl-amine The compound of Example 122 was manufactured by the same method as in Example 95, by a similar method thereto or by a combination of such a method with a conventional method using 2-chloro-3-(difluoromethyl)pyridine, 3-amino-1-methyl-1H-pyrazole and 4-chloro-6-hydroxy-quinazoline.

$^1$HNMR (CD$_3$OD) δ: 3.86 (3H, s), 6.88 (1H, d, J=2.0Hz), 7.11 (1H, t, J=55Hz), 7.20-7.24 (1H, m), 7.42 (1H, d, J=2.0Hz), 7.65 (1H, dd, J=8.8, 2.4Hz), 7.90 (1H, d, J=8.8Hz), 8.06-8.09 (2H, m), 8.22-8.24 (1H, m), 8.66 (1H, s)

ESI-MS (m/e): 369 [M+H]$^+$

Example 121

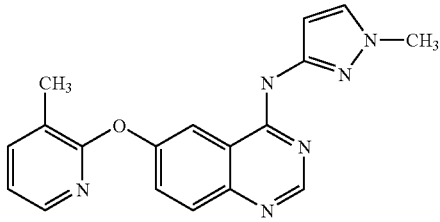

N-(1-Methyl-1H-pyrazol-3-yl)-6-[(3-methylpyridin-2-yl)oxy]quinazolin-4-yl-amine

The compound of Example 121 was manufactured by the same method as in Example 95, by a similar method thereto or by a combination of such a method with a conventional method using 2-chloro-3-methylpyridine, 3-amino-1-methyl-1H-pyrazole and 4-chloro-6-hydroxy-quinazoline.

$^1$HNMR (CD$_3$OD) δ: 2.42 (3H, s), 3.87 (3H, s), 6.82 (1H, d, J=2.4Hz), 7.04-7.08 (1H, m), 7.46 (1H, d, J=2.4Hz), 7.61 (1H, dd, J=8.8, 2.4Hz), 7.68 (1H, dd, J=7.2, 1.6Hz), 7.87 (1H, d, J=8.8Hz), 7.96-7.99 (2H, m), 8.61 (1H, s)

ESI-MS (m/e): 333 [M+H]$^+$

Example 123

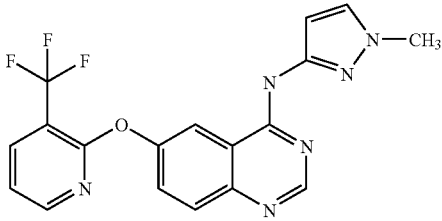

N-(1-Methyl-1H-pyrazol-3-yl)-6-{[3-(trifluoromethyl)-pyridin-2-yl]oxy}quinazolin-4-yl-amine The compound of Example 123 was manufactured by the same method as in Example 95, by a similar method thereto or by a combination of such a method with a conventional method using 2-chloro-3-(trifluoromethyl)pyridine, 3-amino-1-methyl-1H-pyrazole and 4-chloro-6-hydroxy-quinazoline.

$^1$HNMR (CD$_3$OD) δ: 3.87 (3H, s), 6.89 (1H, brs), 7.21-7.24 (1H, m), 7.42 (1H, brs), 7.66 (1H, d, J=8.8Hz), 7.90 (1H, d, J=8.8Hz), 8.07-8.11 (2H, m), 8.30 (1H, d, J=3.6Hz), 8.67 (1H, s)

ESI-MS (m/e): 387 [M+H]$^+$

Example 124

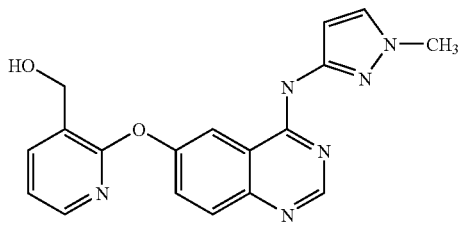

[2-({4-[(1-Methyl-1H-pyrazol-3-yl)amino]quinazolin-6-yl}oxy)pyridin-3-yl]methanol The compound of Example 124 was manufactured by the same method as in Example 95, by a similar method thereto or by a combination of such a method with a conventional method using 2-chloro-3-hydroxymethylpyridine, 3-amino-1-methyl-1H-pyrazole and 4-chloro-6-hydroxy-quinazoline.

$^1$HNMR (CD$_3$OD) δ: 3.87 (3H, s), 4.85 (2H, s), 6.81 (1H, d, J=2.4Hz), 7.13-7.16 (1H, m), 7.44 (1H, d, J=2.4Hz), 7.63 (1H, dd, J=8.0, 2.0Hz), 7.86 (1H, d, J=8.8Hz), 7.96 (1H, dd, J=6.4, 2.0Hz), 8.01 (1H, d, J=2.0Hz), 8.03 (1H, dd, J=4.8, 2.0Hz), 8.62 (1H, s)

ESI-MS (m/e): 349 [M+H]$^+$

Example 125

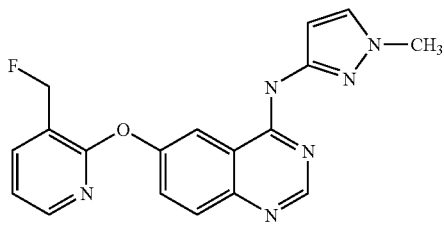

6-{[3-(Fluoromethyl)pyridin-2-yl]oxy}-N-(1-methyl-1H-pyrazol-3-yl)quinazolin-4-yl-amine The compound of Example 125 was manufactured by the same method as in Example 95, by a similar method thereto or by a combination of such a method with a conventional method using 2-chloro-3-fluoromethylpyridine, 3-amino-1-methyl-1H-pyrazole and 4-chloro-6-hydroxy-quinazoline.

$^1$HNMR (CD$_3$OD) δ: 3.87 (1H, s), 5.64 (2H, d, J=47Hz), 6.84 (1H, d, J=2.4Hz), 7.16-7.19 (1H, m), 7.45 (1H, d, J=2.4Hz), 7.65 (1H, dd, J=8.8, 2.8Hz), 7.88 (1H, d, J=8.8Hz), 7.93 (1H, d, J=6.4Hz), 8.05 (1H, d, J=2.0Hz), 8.13 (1H, d, J=4.8Hz), 8.64 (1H, s)

ESI-MS (m/e): 351 [M+H]$^+$

Example 126

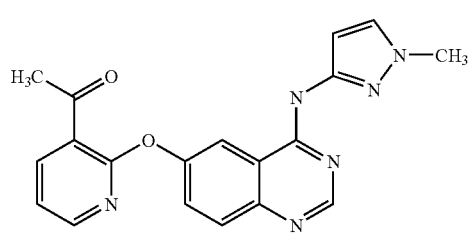

1-[2-({4-[(1-Methyl-1H-pyrazol-3-yl)amino]-quinazolin-6-yl}oxy)pyridin-3-yl]ethanone The compound of Example 126 was manufactured by the same method as in Example 95, by a similar method thereto or by a combination of such a method with a conventional method using 3-acetyl-2-chloropyridine, 3-amino-1-methyl-1H-pyrazole and 4-chloro-6-hydroxy-quinazoline.

$^1$HNMR (CD$_3$OD) δ: 2.83 (3H, s), 3.88 (3H, s), 6.87 (1H, br), 7.20-7.24 (1H, m), 7.43 (1H, d, J=2.4Hz), 7.65 (1H, d, J=8.8Hz), 7.90 (1H, d, J=8.8Hz), 8.10 (1H, d, J=2.4Hz), 8.26-8.30 (2H, m), 8.63 (1H, s)

ESI-MS (m/e): 361 [M+H]$^+$

Example 127

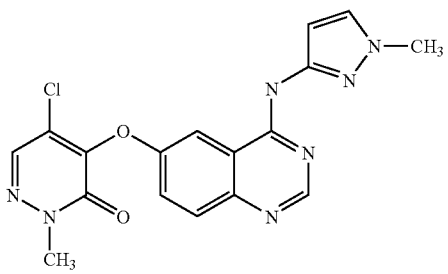

5-Chloro-2-methyl-4-({4-[(1-methyl-1H-pyrazol-3-yl)amino]quinazolin-6-yl}oxy)pyridazin-3(2H)-one The compound of Example 127 was manufactured by the same method as in Example 95, by a similar method thereto or by a combination of such a method with a conventional method using 4,5-dichloro-2-methyl-3(2H)pyridazinone, 3-amino-1-methyl-1H-pyrazole and 4-chloro-6-hydroxy-quinazoline.

$^1$HNMR (CD$_3$OD) δ: 3.82 (3H, s), 3.87 (3H, s), 6.83 (1H, d, J=2.4Hz), 7.44 (1H, d, J=2.4Hz), 7.61 (1H, dd, J=8.8, 2.4Hz), 7.71 (1H, d, J=2.4Hz), 7.85 (1H, d, J=8.8Hz), 7.99 (1H, s), 8.60 (1H, s)

ESI-MS (m/e): 384 [M+H]$^+$

Example 128

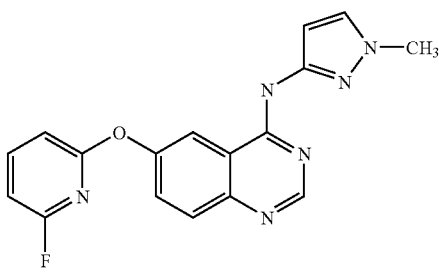

6-[(6-Fluoropyridin-2-yl)oxy]-N-(1-methyl-1H-pyrazol-3-yl)quinazolin-4-yl-amine

The compound of Example 128 was manufactured by the same method as in Example 95, by a similar method thereto or by a combination of such a method with a conventional method using 2,6-difluoropyridine, 3-amino-1-methyl-1H-pyrazole and 4-chloro-6-hydroxy-quinazoline.

$^1$HNMR (CD$_3$OD) δ: 3.89 (3H, s), 6.74 (1H, dd, J=8.0, 2.4Hz), 6.79 (1H, d, J=2.4Hz), 6.91 (1H, d, J=8.0Hz), 7.47 (1H, d, J=2.4Hz), 7.68 (1H, dd, J=8.8, 2.0Hz), 7.88 (1H, d, J=8.8Hz), 7.89-7.96 (1H, s), 8.15 (1H, d, J=2.8Hz), 8.62 ((1H, s)

ESI-MS (m/e): 337 [M+H]$^+$

Example 130

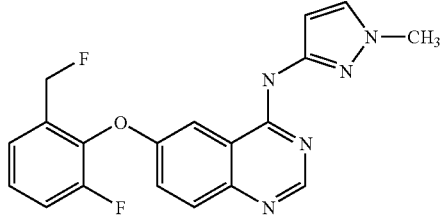

6-[2-Fluoro-6-(fluoromethyl)phenoxy]-N-(1-methyl-1H-pyrazol-3-yl)quinazolin-4-yl-amine The compound of Example 130 was manufactured by the same method as in Example 95, by a similar method thereto or by a combination of such a method with a conventional method using 1,2-difluoro-3-(fluoromethyl)benzene, 3-amino-1-methyl-1H-pyrazole and 4-chloro-6-hydroxy-quinazoline.

$^1$HNMR (CD$_3$OD) δ: 3.85 (3H, s), 5.47 (2H, d, J=47Hz), 6.82 (1H, d, J=2.4Hz), 7.25-7.42 (4H, m), 7.52 (1H, dd, J=8.8, 2.4Hz), 7.59 (1H, d, J=2.4Hz), 7.82 (1H, d, J=8.8Hz), 8.59 (1H, s)

ESI-MS (m/e): 368 [M+H]$^+$

Example 129

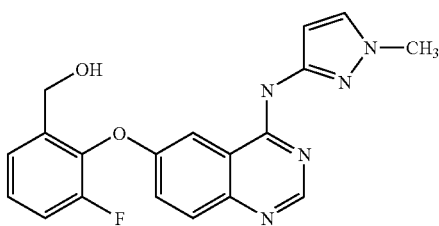

[3-Fluoro-2-({4-[(1-methyl-1H-pyrazol-3-yl)amino]-quinazolin-6-yl}oxy)phenyl]methanol The compound of Example 129 was manufactured by the same method as in Example 95, by a similar method thereto or by a combination of such a method with a conventional method using 2,3-difluorobenenemethanol, 3-amino-1-methyl-1H-pyrazole and 4-chloro-6-hydroxy-quinazoline.

$^1$HNMR (CD$_3$OD) δ: 3.85 (3H, s), 4.72 (2H, s), 6.75 (1H, br), 7.14-7.19 (1H, m), 7.27-7.33 (1H, m), 7.69 (1H, dd, J=8.0, 1.6Hz), 7.85 (1H, d, J=8.8Hz), 7.41-7.44 (2H, m), 7.56 (2H, br), 7.79 (1H, br), 8.55 (1H, s)

ESI-MS (m/e): 366 [M+H]$^+$

Example 131

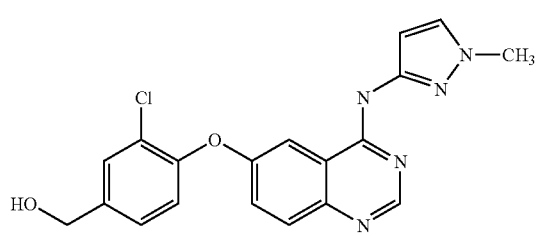

[3-Chloro-4-({4-[(1-methyl-1H-pyrazol-3-yl)amino]-quinazolin-6-yl}oxy)phenyl]methanol The compound of Example 131 was manufactured by the same method as in Example 95, by a similar method thereto or by a combination of such a method with a conventional method using 4-fluoro-3-chlorobenzenemethanol, 3-amino-1-methyl-1H-pyrazole and 4-chloro-6-hydroxy-quinazoline.

$^1$HNMR (CD$_3$OD) δ: 3.87 (3H, s), 4.67 (2H, s), 6.80 (1H, br), 7.13 (1H, d, J=8.8Hz), 7.42 (1H, d, J=2.4Hz), 7.52 (1H, d, J=8.0Hz), 7.55 (1H, d, J=2.4Hz), 7.66 (1H, br), 7.83 (1H, d, J=8.4Hz), 8.58 (1H, s)

ESI-MS (m/e): 382 [M+H]$^+$

Example 132

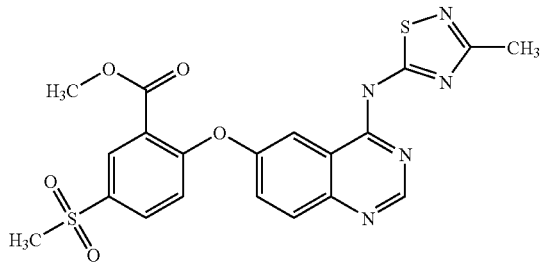

Methyl 5-(methylsulfonyl)-2-({4-[(3-methyl-[1,2,4]-thiadiazol-5-yl)amino]quinazolin-6-yl}oxy)benzoate The compound of Example 132 was manufactured by the same method as in Example 95, by a similar method thereto or by a combination of such a method with a conventional method using methyl 2-fluoro-5-methylsulfonylbenzoate, 5-amino-3-methyl-[1,2,4]thiadiazole and 4-chloro-6-hydroxy-quinazoline.

$^1$HNMR (CD$_3$OD) δ: 2.55 (3H, s), 3.19 (3H, s), 3.91 (3H, s), 7.25 (1H, d, J=8.8Hz), 7.72 (1H, dd, J=8.8, 2.4Hz), 8.03 (1H, d, J=2.8Hz), 8.05 (1H, d, J=8.8Hz), 8.11 (1H, dd, J=8.8, 2.8Hz), 8.58 (1H, d, J=2.4Hz), 8.95 (1H, s)

ESI-MS (m/e): 472 [M+H]$^+$

Example 133

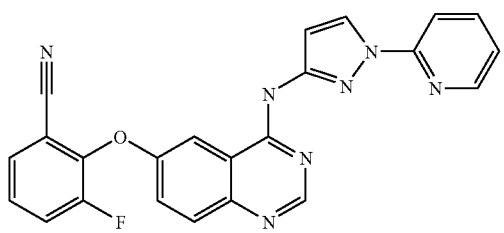

3-Fluoro-2-({4-[(1-pyridin-2-yl-1H-pyrazol-3-yl)-amino]quinazolin-6-yl}oxy)benzonitrile The compound of Example 133 was manufactured by the same method as in Example 95, by a similar method thereto or by a combination of such a method with a conventional method using 2,3-difluorobenzonitrile, 3-amino-1-(pyridin-2-yl)-1H-pyrazole and 4-chloro-6-hydroxy-quinazoline.

$^1$HNMR (CD$_3$OD) δ: 7.23-7.26 (2H, m), 7.47-7.51 (1H, m), 7.43 (1H, d, J=2.0Hz), 7.69 (1H, dd, 8.0, 1.6Hz), 7.60-7.67 (4H, m), 7.84-7.90 (2H, s), 7.93 (1H, d, J=2.8Hz), 8.41 (1H, d, J=5.2Hz), 8.52 (1H, d, J=2.8Hz), 8.66 (1H, s)

ESI-MS (m/e): 424 [M+H]$^+$

Example 134

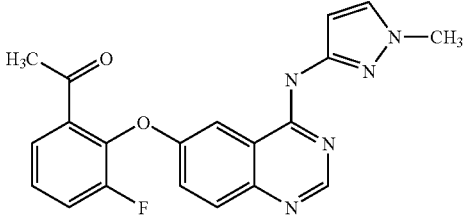

1-[3-Fluoro-2-({4-[(1-methyl-1H-pyrazol-3-yl)amino]-quinazolin-6-yl}oxy)phenyl]ethanone The compound of Example 134 was manufactured by the same method as in Example 95, by a similar method thereto or by a combination of such a method with a conventional method using 1-(2,3-difluoro phenyl)ethanone, 3-amino-1-methyl-1H-pyrazole and 4-chloro-6-hydroxy-quinazoline.

$^1$HNMR (CD$_3$OD) δ: 2.60 (3H, s), 3.85 (3H, s), 6.85 (1H, d, J=2.4Hz), 7.37-7.43 (3H, m), 7.55 (1H, dd, J=8.8, 2.8Hz), 7.61 (1H, d, J=2.8Hz), 7.69-7.71 (1H, m), 7.86 (1H, d, J=8.8Hz), 8.61 (1H, s)

ESI-MS (m/e): 378 [M+H]$^+$

Example 135

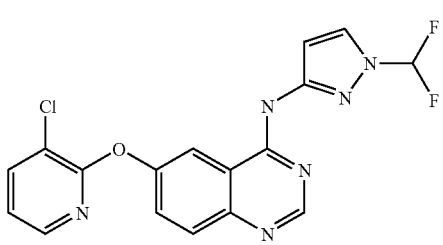

6-[(3-Chloropyridin-2-yl)oxy]-N-[1-(difluoromethyl)-1H-pyrazol-3-yl]quinazolin-4-yl-amine The compound of Example 135 was manufactured by the same method as in Example 95, by a similar method thereto or by a combination of such a method with a conventional method using 2,3-dichloropyridine, 3-amino-1-(difluoromethyl)-1H-pyrazole and 4-chloro-6-hydroxy-quinazoline.

$^1$HNMR (CD$_3$OD) δ: 7.12-7.15 (1H, m), 7.21 (1H, d, J=2.8Hz), 7.31 (1H, t, J=60Hz), 7.70 (1H, dd, J=8.8, 2.4Hz), 7.90-7.94 (3H, m), 8.04 (1H, dd, J=4.8, 1.6Hz), 8.17 (1H, d, J=2.4Hz), 8.68 (1H, s)

ESI-MS (m/e): 389 [M+H]$^+$

Example 136

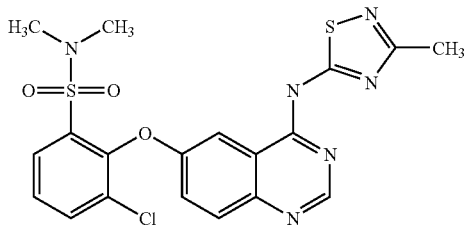

3-Chloro-N,N-dimethyl-2-({4-[(3-methyl-[1,2,4]-thiadiazol-5-yl)amino]quinazolin-6-yl}oxy)benzene-sulfon-amide The compound of Example 136 was manufactured by the same method as in Example 95, by a similar method thereto or by a combination of such a method with a conventional method using 2,3-dichloro-N,N-dimethyl-benzenesulfona-mide, 5-amino-3-methyl-[1,2,4]thiadiazole and 4-chloro-6-hydroxy-quinazoline.

$^1$HNMR (CD$_3$OD) δ: 2.54 (3H, s), 2.92 (6H, s), 7.53 (1H, t, J=8.0Hz), 7.62 (1H, dd, J=8.8, 2.8Hz), 7.76 (1H, d, J=2.8Hz), 7.80 (1H, dd, J=8.0, 1.6Hz), 8.00 (1H, d, J=8.8Hz), 8.02 (1H, dd, J=8.0, 1.2 Hz), 8.89 (1H, s)

ESI-MS (m/e): 477 [M+H]$^+$

Example 137

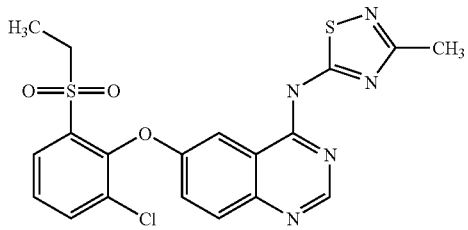

6-[2-Chloro-6-(ethylsulfonyl)phenoxy]-N-(3-methyl-1,2,4-thiadiazol-5-yl)quinazolin-4-yl-amine The compound of Example 137 was manufactured by the same method as in Example 95, by a similar method thereto or by a combination of such a method with a conventional method using 1,2-dichloro-3-(ethanesulfonyl)benzene, 5-amino-3-methyl-[1,2,4]thiadiazole and 4-chloro-6-hydroxy-quinazoline.

$^1$HNMR (CD$_3$OD) δ: 1.34 (3H, t, J=7.2Hz), 2.54 (3H, s), 3.47 (2H, q, J=7.2Hz), 7.56 (1H, t, J=8.0Hz), 7.65 (1H, dd, J=8.8, 2.4Hz), 7.71 (1H, d, J=2.4Hz), 7.86 (1H, dd, J=8.0, 1.6Hz), 7.98 (1H, d, J=8.8Hz), 8.09 (1H, dd, J=8.0, 1.6Hz), 8.89 (1H, s)

ESI-MS (m/e): 356 [M+H]$^+$

Example 138

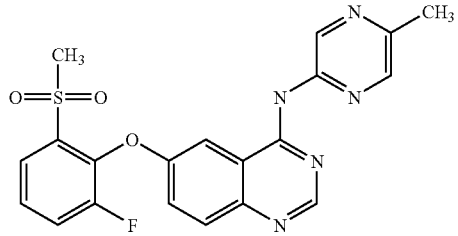

6-[2-Fluoro-6-(methylsulfonyl)phenoxy]-N-(5-methylpyrazin-2-yl)quinazolin-4-yl-amine 5-Methylpyrazin-2-amine (1.70 g; 15.6 mmol), 0.37 g (0.6 mmol) 2,2-bisdiphenylphosphino-1,1-binaphthyl, 7.80 g (24.0 mmol) of cesium carbonate and trisdibenzylidene acetone palladium were added to a solution of 2.70 g (12.0 mmol) of 4-chloro-6-acetate-quinazoline in 150 ml of toluene and the mixture was stirred at 111° C. for 18 hours. The reaction solution was filtered, water was added to the filtrate and the mixture was extracted with chloroform. The organic layer was dried and concentrated, 100 ml of tetrahydrofuran and 100 ml of methanol were added to the resulting residue, then 10 ml of aqueous ammonia was added thereto, the mixture was stirred for 30 minutes, the reaction solution was concentrated, the resulting residue was stirred for one night as a methanolic solution, the reaction solution was filtered and the residue was dried to give 1.30 g (yield: 42%) of 6-hydroxy-N-(5-methylpyrazin-2-yl)quinazolin-4-yl-amine as a yellow solid. The resulting hydroxyl compound (50 mg; 0.20 mmol) and 94 mg (0.50 mmol) of 1,2-difluoro-3-methanesulfonylbenzene were added to a solution of 57 mg (0.50 mmol) of tert-butoxy potassium in 3 ml of N,N-dimethylacetamide and the mixture was stirred at 77° C. for 4 hours. Water was added to the reaction solution and the mixture was extracted with chloroform. The organic layer was dried and concentrated and the resulting residue was purified by a reversed phase HPLC (0.1% TFA-containing water:acetonitrile=90:10→10:90) to give 24 mg (yield: 29%) of the title compound as a yellow solid.

$^1$HNMR (CD$_3$OD) δ: 2.56 (3H, s), 3.34 (3H, s), 7.54-7.70 (3H, m), 7.90-7.95 (3H, m), 8.27 (1H, s), 8.70 (1H, s), 9.61 (1H, s)

ESI-MS (m/e): 426 [M+H]$^+$

Example 139

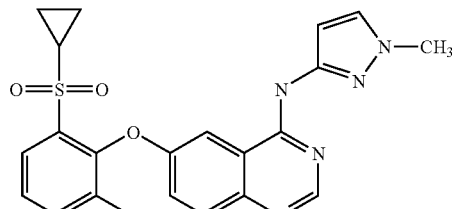

6-[2-Chloro-6-(cyclopropylsulfonyl)phenoxy]-N-(1-methyl-1H-pyrazol-3-yl)quinazolin-4-yl-amine The compound of Example 139 was manufactured by the same method as in Example 95, by a similar method thereto or by a combination of such a method with a conventional method using 1,2-dichloro-3-(cyclopropylsulfonyl)benzene, 3-amino-1-methyl-1H-pyrazole and 4-chloro-6-hydroxy-quinazoline.

$^1$HNMR (CD$_3$OD) δ: 1.10-1.13 (2H, m), 1.28-1.31 (2H, m), 2.97-3.03 (1H, m), 3.85 (3H, s), 6.71 (1H, br), 7.47-7.55 (3H, m), 7.68 (1H, brs), 7.84-7.87 (2H, m), 7.98 (1H, dd, J=8.8, 1.6Hz), 8.54 (1H, s)

ESI-MS (m/e): 456 [M+H]$^+$

Example 140

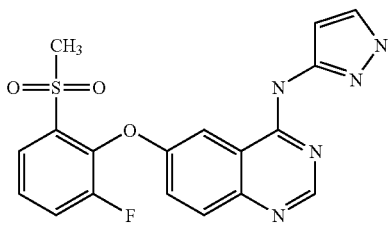

6-[2-Fluoro-6-(methylsulfonyl)phenoxy]-N-(1H-pyrazol-3-yl)quinazolin-4-yl-amine

The compound of Example 140 was manufactured by the same method as in Example 95, by a similar method thereto or by a combination of such a method with a conventional method using 1,2-difluoro-3-(methylsulfonyl)benzene, 3-amino-1H-pyrazole and 4-chloro-6-hydroxy-quinazoline.

$^1$HNMR (CD$_3$OD) δ: 3.35 (3H, s), 7.48-7.58 (4H, m), 7.61 (1H, d, J=8.8Hz), 7.77 (1H, brs), 7.87 (1H, d, J=8.8Hz), 7.93 (1H, d, J=7.6Hz), 8.65 (1H, s)

ESI-MS (m/e): 400 [M+H]$^+$

Example 141

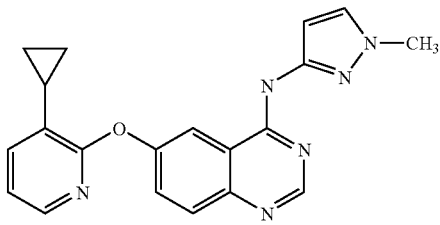

6-[3-Cyclopropylpyridin-2-yl]oxy]-N-(1-methyl-1H-pyrazol-3-yl)quinazolin-4-yl-amine The compound of Example 141 was manufactured by the same method as in Example 95, by a similar method thereto or by a combination of such a method with a conventional method using 3-cyclopropyl-2-chloropyridine, 3-amino-1-methyl-1H-pyrazole and 4-chloro-6-hydroxy-quinazoline.

$^1$HNMR (CD$_3$OD) δ: 0.79-0.89 (2H, m), 1.03-1.08 (2H, m), 2.21-2.25 (1H, m), 3.88 (3H, s), 6.77 (1H, brs), 7.06-7.09 (1H, m), 7.43 (1H, dd, J=7.4, 1.6Hz), 7.49 (1H, brs), 7.63 (1H, d, J=8.4Hz), 7.86 (1H, d, J=8.4Hz), 7.93 (1H, dd, J=4.8, 1.6Hz), 8.04 (1H, d, J=2.4Hz), 8.59 (1H, s)

ESI-MS (m/e): 359 [M+H]$^+$

Example 142

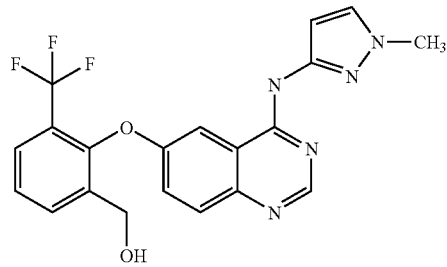

[2-({4-[(1-Methyl-1H-pyrazol-3-yl)amino]quinazolin-6-yl}oxy)-3-(trifluoromethyl)phenyl]methanol The compound of Example 142 was manufactured by the same method as in Example 95, by a similar method thereto or by a combination of such a method with a conventional method using 2-fluoro-3-(trifluoromethyl)-benzenemethanol, 3-amino-1-methyl-1H-pyrazole and 4-chloro-6-hydroxy-quinazoline.

$^1$HNMR (CD$_3$OD) δ: 3.85 (3H, s), 4.53 (2H, s), 6.77 (1H, d, J=2.4Hz), 7.41-7.52 (4H, m), 7.72 (1H, d, J=7.6Hz), 7.80 (1H, d, J=8.8Hz), 7.93 (1H, d, J=7.6Hz), 8.56 (1H, s)

ESI-MS (m/e): 416 [M+H]$^+$

Example 143

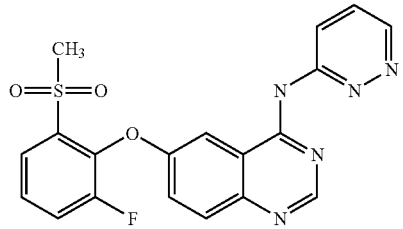

6-[2-Fluoro-6-(methylsulfonyl)phenoxy]-N-pyridazin-3-ylquinazolin-4-yl-amine

The compound of Example 143 was manufactured by the same method as in Example 95, by a similar method thereto or by a combination of such a method with a conventional method using 1,2-difluoro-3-(methylsulfonyl)benzene, 3-amino-pyridazine and 4-chloro-6-hydroxy-quinazoline.

$^1$HNMR (CD$_3$OD) δ: 3.37 (3H, s), 7.51-7.66 (4H, m), 7.90 (1H, d, J=8.8Hz), 7.94-7.96 (3H, m), 8.64 (1H, br), 8.84 (1H,

ESI-MS (m/e): 412 [M+H]$^+$ s)

Example 144

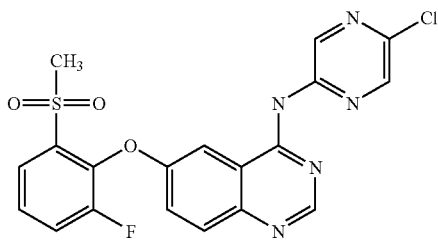

N-(5-Chloropyrazin-2-yl)-6-[2-fluoro-6-(methylsulfonyl)phenoxy]quinazolin-4-yl-amine The compound of Example 144 was manufactured by the same method as in Example 95, by a similar method thereto or by a combination of such a method with a conventional method using 1,2-difluoro-3-(methylsulfonyl)benzene, 2-amino-5-chloropyrazine and 4-chloro-6-hydroxy-quinazoline.

$^1$HNMR (CD$_3$OD) δ: 3.37 (3H, s), 7.54-7.60 (2H, m), 7.71 (1H, dd, J=8.8, 2.8Hz), 7.80 (1H, d, J=2.8Hz), 7.95 (1H, s), 7.96 (1H, d, J=8.8Hz), 8.29 (1H, s), 8.79 (1H, s), 9.84 (1H, s)

ESI-MS (m/e): 446 [M+H]$^+$

Example 145

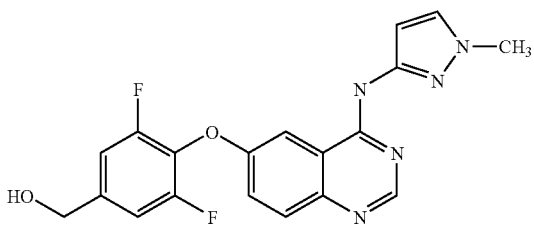

[3,5-Difluoro-4-({4-[(1-methyl-1H-pyrazol-3-yl)-amino]quinazolin-6-yl}oxy)phenyl]methanol The compound of Example 145 was manufactured by the same method as in Example 95, by a similar method thereto or by a combination of such a method with a conventional method using 3,4,5-trifluoro-benzenemethanol, 3-amino-1-methyl-1H-pyrazole and 4-chloro-6-hydroxy-quinazoline.

$^1$HNMR (CD$_3$OD) δ: 3.83 (3H, s), 4.65 (2H, s), 6.80 (1H, d, J=2.0Hz), 7.07-7.09 (2H, m), 7.42 (1H, d, J=2.0Hz), 7.57 (1H, dd, J=8.8, 2.0Hz), 7.67 (1H, d, J=2.4Hz), 7.83 (1H, d, J=8.8Hz), 8.59 (1H, s)

ESI-MS (m/e): 384 [M+H]$^+$

Example 146

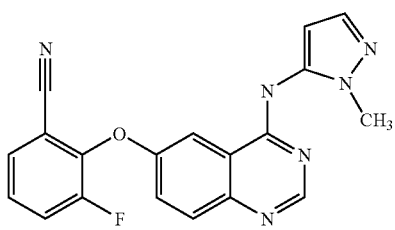

3-Fluoro-2-({4-[(1-methyl-1H-pyrazol-5-yl)amino-quinazolin-6-yl}oxy)benzonitrile The compound of Example 146 was manufactured by the same method as in Example 95, by a similar method thereto or by a combination of such a method with a conventional method using 2,3-difluorobenzonitrile, 5-amino-1-methyl-1H-pyrazole and 4-chloro-6-hydroxy-quinazoline.

$^1$HNMR (CD$_3$OD) δ: 3.70 (3H, s), 7.38-7.44 (1H, m), 7.53-7.60 (3H, m), 7.66-7.69 (3H, m), 8.00 (1H, d, J=9.2Hz), 9.00 (1H, s)

ESI-MS (m/e): 361 [M+H]$^+$

Example 147

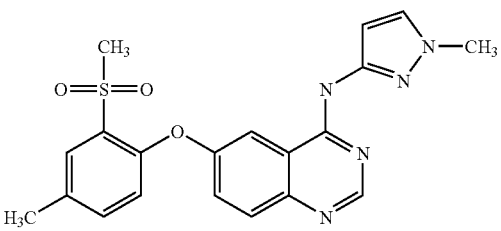

6-[4-Methyl-2-(methylsulfonyl)phenoxy]-N-(1-methyl-1H-pyrazol-3-yl)quinazolin-4-yl-amine The compound of Example 147 was manufactured by the same method as in Example 95, by a similar method thereto or by a combination of such a method with a conventional method using 1-fluoro-4-methyl-2-(methylsulfonyl)benzene, 3-amino-1-methyl-1H-pyrazole and 4-chloro-6-hydroxy-quinazoline.

$^1$HNMR (CD$_3$OD) δ: 2.46 (3H, s), 3.87 (3H, s), 6.75 (1H, brs), 7.00 (1H, d, J=8.8Hz), 7.49 (1H, brs), 7.65 (1H, s), 7.87 (1H, d, J=8.8Hz), 7.88 (1H, s), 7.99 (1H, brs), 8.59 (1H, s)

ESI-MS (m/e): 410 [M+H]$^+$

Example 148

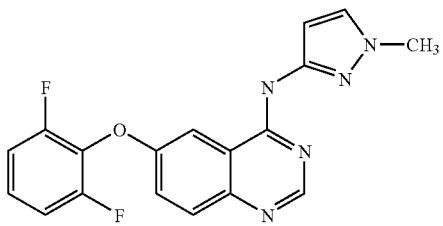

6-(2,6-Difluorophenoxy)-N-(1-methyl-pyrazol-3-yl)-quinazolin-4-yl-amine

The compound of Example 148 was manufactured by the same method as in Example 95, by a similar method thereto or by a combination of such a method with a conventional method using 1,2,3-trifluorobenzene, 3-amino-1-methyl-1H-pyrazole and 4-chloro-6-hydroxy-quinazoline.

$^1$HNMR (CDCl$_3$) δ: 3.80 (3H, s), 7.03 (2H, t, J=8.4Hz), 7.14-7.17 (1H, m), 7.33 (1H, br), 7.50-7.61 (1H, m), 7.91-7.94 (2H, m), 8.02 (1H, brs), 8.75 (1H, s)

ESI-MS (m/e): 354 [M+H]$^+$

Example 149

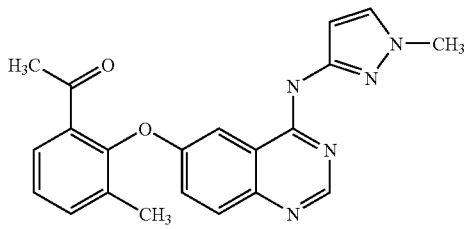

1-[3-Methyl-2-([4-[(1-methyl-pyrazol-3-yl)amino]-quinazolin-6-yl]oxy)phenyl]ethanone 4-[(1-Methyl-1H-pyrazol-3-yl)amino]quinazolin-6-ol (71 mg; 0.295 mmol) and 90 mg (0.592 mmol) of 1-(2-fluoro-3-methylphenyl)ethanone were added to a solution of 82 mg (0.732 mmol) of tert-butoxy potassium in 5 ml of N,N-dimethylacetamide and the mixture was stirred at 130° C. for 5 hours. Water was added to the reaction solution and the mixture was extracted with chloroform. The organic layer was dried and concentrated and the resulting residue was purified by a silica gel chromatography (chloroform:methanol=12:1) to give 6 mg (yield: 5%) of the title compound as a colorless solid.

$^1$HNMR (CD$_3$OD) δ: 2.16 (3H, s), 2.54 (3H, s), 3.83 (3H, s) 6.90 (1H, br), 7.16 (1H, br), 7.33-7.35 (2H, m), 7.45-7.53 (2H, m), 7.70 (1H, d, J=6.8Hz), 7.86 (1H, d, J=8.8Hz), 8.64 (1H, s)

ESI-MS (m/e): 374 [M+H]$^+$

Example 150

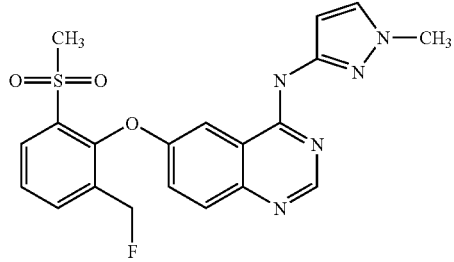

6-[2-(Fluoromethyl)-6-(methylsulfonyl)phenoxy]-N-(1-methyl-pyrazol-3-yl)quinazolin-4-yl-amine The compound of Example 150 was manufactured by the same method as in Example 95, by a similar method thereto or by a combination of such a method with a conventional method using 2-fluoro-1-(fluoromethyl)-3-(methylsulfonyl) benzene, 3-amino-1-methyl-1H-pyrazole and 4-chloro-6-hydroxy-quinazoline.

$^1$HNMR (CD$_3$OD) δ: 3.30 (3H, s), 3.82 (3H, s), 5.23 (2H, d, J=47Hz), 6.88 (1H, d, J=2.0Hz), 7.43 (1H, d, J=2.0Hz), 7.51 (1H, dd, J=8.8, 3.2Hz), 7.60 (1H, d, J=8.0Hz), 7.86-7.91 (3H, m), 8.16 (1H, d, J=7.2Hz), 8.64 (1H, s)

ESI-MS (m/e): 428 [M+H]$^+$

Example 151

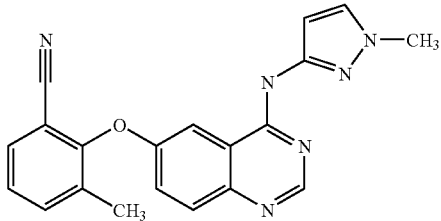

3-Methyl-2-({4-[(1-methyl-pyrazol-3-yl)amino]-quinazolin-6-yl}oxy)benzonitrile

4-[(1-Methyl-1H-pyrazol-3-yl)amino]quinazolin-6-ol (90 mg; 0.373 mmol) and 100 mg (0.741 mmol) of 2-fluoro-3-methylbenzonitrile were added to a solution of 105 mg (0.937 mmol) of tert-butoxy potassium in 5 ml of N,N-dimethylacetamide and the mixture was stirred at 110° C. for 4 hours. Water was added to the reaction solution and the mixture was extracted with chloroform. The organic layer was dried and concentrated and the resulting residue was purified by a silica gel chromatography (chloroform:methanol=12:1) to give 31 mg (yield: 23%) of the title compound as a colorless solid.

$^1$HNMR (CD$_3$OD) δ: 2.20 (3H, s), 3.82 (3H, s), 6.80 (1H, brs), 7.28-7.33 (1H, m), 7.43-7.45 (2H, m), 7.56-7.60 (3H, m), 7.81 (1H, d, J=8.4Hz), 8.55 (1H, brs)

ESI-MS (m/e): 357 [M+H]$^+$

Example 152

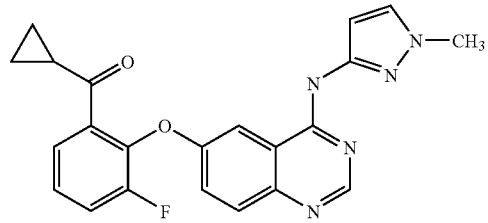

Cyclopropyl[3-fluoro-2-([4-[{1-methyl-pyrazol-3-yl}-amino]-quinazolin-6-yl]oxy)phenyl]methanone 4-[(1-Methyl-1H-pyrazol-3-yl)amino]quinazolin-6-ol (70 mg; 0.290 mmol) and 63 mg (0.346 mmol) of cyclopropyl(2,3-difluorophenyl)methanone were added to a solution of 81 mg (0.723 mmol) of tert-butoxy potassium in 6 ml of N,N-dimethylacetamide and the mixture was stirred at 110° C. for 1 hour. Water was added to the reaction solution and the mixture was extracted with chloroform. The organic layer was dried and concentrated and the resulting residue was purified by a silica gel chromatography (chloroform:methanol=10:1) to give 36 mg (yield: 31%) of the title compound as a colorless solid.

$^1$HNMR (CD$_3$OD) δ: 0.95-1.00 (2H, m), 1.14-1.18 (2H, m), 2.55-2.59 (1H, m), 3.84 (3H, s), 6.92 (1H, brs), 7.33-7.57 (6H, m), 7.87 (1H, d, J=8.8Hz), 8.66 (1H, s)

ESI-MS (m/e): 404 [M+H]$^+$

Example 153

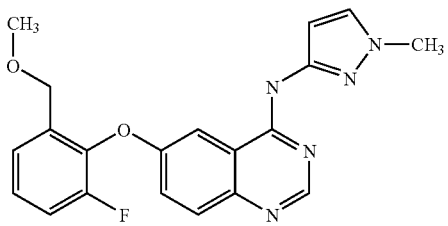

6-[2-(Fluoro)-6-(methylmethyl)phenoxy]-N-(1-methyl-pyrazol-3-yl)quinazolin-4-yl-amine The compound of Example 153 was manufactured by the same method as in Example 95, by a similar method thereto or by a combination of such a method with a conventional method using 1,2-difluoro-3-(methoxymethyl)benzene, 3-amino-1-methyl-1H-pyrazole and 4-chloro-6-hydroxy-quinazoline.

$^1$HNMR (CD$_3$OD) δ: 3.34 (3H, s), 3.82 (3H, s), 6.95 (1H, brs), 7.12-7.17 (2H, m), 7.22-7.27 (1H, m), 7.31-7.34 (1H, m), 7.53 (1H, brs), 7.87 (1H, brs), 8.08 (1H, brs), 8.72 (1H, s)

ESI-MS (m/e):380 [M+H]$^+$

Example 155

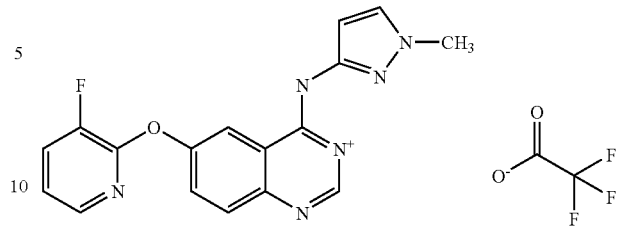

[6-(3-Fluoropyridin-2-yloxy)quinazolin-4-yl]-(1-methyl-1H-pyrazol-3-yl)-amine

The compound of Example 155 was manufactured by the same method as in Example 95, by a similar method thereto or by a combination of such a method with a conventional method using 2-chloro-3-fluoropyridine, 3-amino-1-methyl-1H-pyrazole and 4-chloro-6-hydroxy-quinazoline.

$^1$HNMR (CDCl$_3$) δ: 3.86 (3H, s), 6.93 (1H, d, J=2.3Hz), 7.09-7.13 (1H, m), 7.39 (1H, d, J=2.3Hz), 7.54-7.59 (1H, m), 7.76 (1H, dd, J=9.0, 2.3Hz), 7.91-7.92 (1H, m), 8.10 (1H, d, J=9.0Hz), 8.15 (1H, d, J=2.3Hz), 8.79 (1H, s)

ESI-MS (m/e): 337 [M+H]$^+$

Example 154

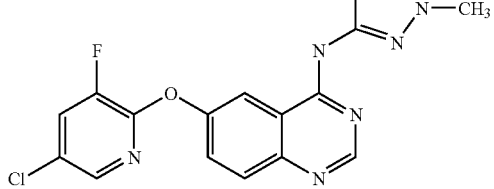

[6-(5-Chloro-3-fluoropyridin-2-yloxy)quinazolin-4-yl]-(1-methyl-1H-pyrazol-3-yl)-amine The compound of Example 154 was manufactured by the same method as in Example 95, by a similar method thereto or by a combination of such a method with a conventional method using 2,5-dichloro-3-fluoropyridine, 3-amino-1-methyl-1H-pyrazole and 4-chloro-6-hydroxy-quinazoline.

$^1$HNMR (DMSO-d6) δ: 3.81 (3H, s), 6.79 (1H, d, J=2.4Hz), 7.69 (1H, d, J=2.4Hz), 7.81 (1H, dd, J=8.8, 2.4Hz), 7.86 (1H, d, J=8.8Hz), 8.13 (1H, d, J=2.4Hz), 8.33 (1H, dd, J=8.8, 2.4Hz), 8.51 (1H, d, J=2.4Hz), 8.70 (1H, s) ESI-MS (m/e): 371 [M+H]$^+$

Example 156

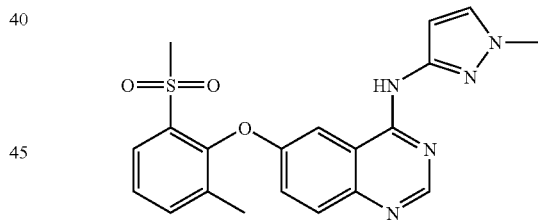

6-[2-Methyl-6-(methylsulfonyl)phenoxy]-N-(1-methyl-pyrazol-3-yl)quinazolin-4-yl-amine The compound of Example 156 was manufactured by the same method as in Example 95, by a similar method thereto or by a combination of such a method with a conventional method using 2-fluoro-1-methyl-3-(methylsulfonyl)benzene, 3-amino-1-methyl-1H-pyrazole and 4-chloro-6-hydroxy-quinazoline.

$^1$HNMR (CDCl$_3$) δ: 2.09 (3H, s), 3.26 (3H, s), 3.81 (3H, s), 6.88-7.00 (1H, br), 7.02-7.12 (1H, br), 7.31 (1H, d, J=2.0Hz), 7.38 (1H, t, J=8.0Hz), 7.46-7.54 (1H, br), 7.55 (1H, d, J=8.0Hz), 7.82-7.96 (1H, br), 7.98 (1H, d, J=8.0Hz), 8.00-8.12 (1H, br)

ESI-MS (m/e): 409 [M+H]$^+$

Example 157

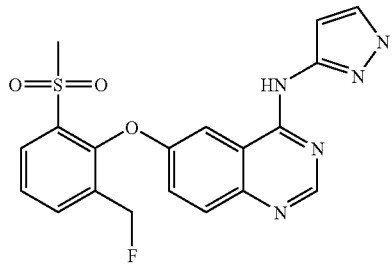

6-[2-(Fluoromethyl)-6-(methylsulfonyl)phenoxy]-N-(1H-pyrazol-3-yl)quinazolin-4-yl-amine The compound of Example 157 was manufactured by the same method as in Example 95, by a similar method thereto or by a combination of such a method with a conventional method using 2-fluoro-1-(fluoromethyl)-3-(methylsulfonyl)benzene, 3-amino-1-methyl-1H-pyrazole and 4-chloro-6-hydroxy-quinazoline.

$^1$HNMR (CD$_3$OD) δ: 3.34 (3H, s), 5.33 (2H, d, J=47Hz), 7.60-7.77 (4H, m), 7.82-7.90 (1H, m), 8.00-8.04 (1H, m), 8.16-8.21 (2H, m), 8.50 (1H, br)

ESI-MS (m/e): 414 [M+H]$^+$

Example 158

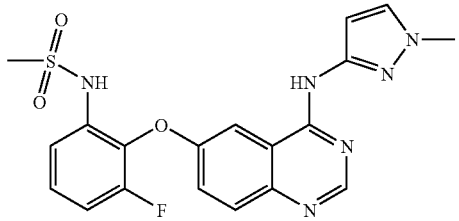

6-[2-Fluoro-6-(methanesulfonamide)phenoxy]-quinazolin-4-yl]-(1-methyl-1H-pyrazol-3-yl)-amine The compound of Example 158 was manufactured by the same method as in Example 95, by a similar method thereto or by a combination of such a method with a conventional method using N-(2,3-difluorophenyl)methanesulfonamide, 3-amino-1-methyl-1H-pyrazole and 4-chloro-6-hydroxy-quinazoline.

$^1$HNMR (CDCl$_3$) δ: 3.04 (3H, s), 3.85 (3H, s), 6.83 (1H, d, J=2.3Hz), 7.01-7.03 (1H, m), 7.26-7.28 (1H, m), 7.36 (1H, d, J=2.3Hz), 7.45 (1H, d, J=8.5Hz), 7.58-7.60 (1H, m), 7.79 (1H, d, J=2.3Hz), 8.03 (1H, d, J=8.5Hz), 8.68 (1H, s)

ESI-MS (m/e): 429 [M+H]$^+$

Pharmacological test example where the compound of the present invention is used as a test compound will be shown as follows.

Pharmacological Test Example 1

Glucokinase Activating Action

Glucokinase activating ability was measured using the compound of the present invention.

Measurement of an excellent glucokinase activating action of the compounds represented by the aforementioned formula (I) is able to be carried out by a method mentioned in literatures such as *Diabetes,* vol. 45, pages 1671 to 1677 (1996) or a method similar thereto.

With regard to the glucokinase activity, glucose-6-phosphate is not directly measured but amount of thio-NADH resulted in the production of phosphogluconolactone from glucose-6-phosphate dehydrogenase which is a reporter enzyme is measured whereby degree of activation of glucokinase is checked.

Recombinant human liver GK used in this assay was expressed in *E. coli* as FLAG fusion protein and purified by ANTIFLAG M2 AFFINITY GEL (Sigma).

The assay was conducted at 30° C. using a flat-bottom 96-well plate. An assay buffer (25 mM Hepes Buffer: pH=7.2; 2 mM MgCl$_2$, 1 mM ATP, 0.5 mM TNAD and 1 mM dithiothreitol) (69 μl) was dispensed and 1 μl of a solution of a compound in DMSO or DMSO (as a control) was added. After that, 20 μl of an enzyme mixture (FLAG-GK, 20 U/ml G6PDH) cooled in ice was added, then 10 μl of 25 mM glucose which is a substrate was added and the reaction was started (final glucose concentration=2.5 mM).

After starting the reaction, an increase in absorbance at 405 nm was measured for 10 minutes every 30 seconds and the compound was evaluated using the increase during the first 5 minutes. FLAG-GK was added in such a manner that an increase in absorbance after 5 minutes in the presence of 1% of DMSO became between 0.05 and 0.1.

OD value in the case of DMSO control was defined as 100% and OD values in various concentrations of the compound to be evaluated were measured. From the OD values in various concentrations, Emax (%) and EC50 (μM) were calculated and used as indexes of GK activating ability of the compound.

GK activating ability of the compound of the present invention was measured. The result is shown in Table 5.

TABLE 5

GK Activating Ability of the Compound of the Present Invention

| Compound Nos. | Emax (%) | EC50 (μM) |
|---|---|---|
| Example 1 | 1000 | 0.18 |
| Example 22 | 860 | 0.08 |
| Example 31 | 1050 | 0.09 |

As shown in Table 5, the compounds of the present invention have an excellent GK activating ability when Emax and EC50 are used as indexes and are useful for treatment and/or prevention of diabetes mellitus, complications of diabetes mellitus or obesity.

INDUSTRIAL APPLICABILITY

In accordance with the present invention, there is provided a novel substance having a glucokinase activating action.

A substituted quinazoline represented by the formula (I) or pyridopyrimidine derivative or a pharmaceutically acceptable salt thereof provided by the present invention has an excellent glucokinase activating action and is useful for treatment and/or prevention of diabetes mellitus, complications of diabetes melleitus or obesity.

What is claimed is:

1. A compound represented by the formula (I):

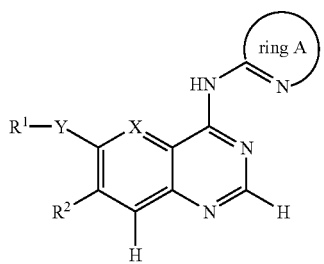

(I)

or a pharmaceutically acceptable salt thereof, wherein:
X is CH;
Y is oxygen atom or sulfur atom;
$R^1$ is one group or atom optionally selected from the following (1), (2), (3), (4), (5) and (6):
 (1) a five- or six-membered heteroaryl group having one to three hetero atom(s) selected from the group consisting of nitrogen atom, sulfur atom and oxygen atom in a ring, said heteroaryl group (1) being optionally fused to a phenyl ring;
 (2) an aryl group;
 (3) a straight-chain or branched lower alkyl group;
 (4) a cycloalkyl group having 3 to 7 carbon atoms;
one of the carbon atoms contained in said group except for a carbon atom bonding to Y, being optionally replaced with an oxygen atom, NH, N-alkanoyl group or carbonyloxy group said $R^1$ may have one to three groups, being the same or different, selected from α;
$R^2$ is hydrogen atom or fluorine atom;
ring A is a monocyclic or bicyclic heteroaryl group represented by the formula (II):

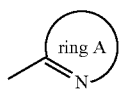

(II)

said ring A optionally having one to three substituent groups selected from β;
substituent group α is selected from the group consisting of:
 a lower alkyl group optionally substituted with one to three halogen atom(s);
 a cycloalkyl group having 3 to 7 carbons;
 a lower alkoxy group;
 a hydroxyl group;
 a hydroxyalkyl group;
said hydrogen atom of the hydroxyl portion of the hydroxyalkyl group being optionally substituted with a lower alkyl group;
 an alkanoyl group;
 halogen atom;
 oxy group;
 a lower alkylsulfonyl group;
 a lower alkylsulfonylamino group;
 a mono- or di-lower alkylcarbamoyl group;
 a mono- or di-lower alkylcarbamoylalkyl group;
 a mono- or di-lower alkylsulfamoyl group;
 an amino group;
 a mono- or di-lower alkylamino group;
 cyano group; and
 a five- or six-membered heteroaryl group which may have one to three hetero atom(s) selected from the group consisting of nitrogen, sulfur and oxygen;
substituent group β is selected from the group consisting of:
 a lower alkyl group;
 a lower alkoxy group;
 a halogen atom;
 a trifluoromethyl group;
 a hydroxyalkyl group;
wherein the hydrogen atom of hydroxyl group in said hydroxyalkyl group may he substituted with a lower alkyl group;
 an aminoalkyl group;
and wherein the amino group in said aminoalkyl group may be further substituted with a lower alkyl group;
 an alkanoyl group;
 carboxyl group;
 an alkoxycarbonyl group; and
 a cyano group.

2. A compound or a pharmaceutically acceptable salt thereof according to claim 1, wherein $R^1$ is a group which is optionally selected from the following (1) and (2):
 (1) a five- or six-membered heteroaryl group having one to three hetero atom(s) selected from the group consisting of nitrogen atom, sulfur atom and oxygen atom in a ring; said heteroaryl group may form a fused ring with phenyl group; and
 (2) an aryl group;
said $R^1$ may have one to three group(s), being same or different, selected from the above-mentioned substituent group α.

3. A compound or a pharmaceutically acceptable salt thereof according to claim 2, wherein the ring A is selected from the group consisting of: thiazolo[5,4-b]pyridinyl, pyrazinyl, thiadiazolyl and pyrazolyl which may have one to three substituent(s), being same or different, selected from the substituent group β.

4. A compound or a pharmaceutically acceptable salt thereof according to claim 3, wherein Y represents a sulfur atom.

5. A compound or a pharmaceutically acceptable salt thereof selected from the group consisting of:
 [6-(4H-[1,2,4]triazol-3-ylsulfanyl)-quinazolin-4-yl]-thiazolo[5,4-b]pyridin-2-yl-amine,
 (6-(4-methyl-4H-[1,2,4]triazol-3-ylsulfanyl)-quinazolin-4-yl]-thiazol-2-yl-amine,
 [6-(4-methyl-4H-[1,2,4]-triazol-3-ylsulfanyl)-quinazolin-4-yl]-pyrazin-2-yl -amine,
 (6-phenoxy-quinazolin-4-yl)-pyrazin-2-yl-amine,
 [6-(4H-[1,2,4]triazol-3-ylsulfanyl)-quinazolin-4-yl-pyrazin-2-yl-amine,
 [6-(4-methyl-4H-[1,2,4]triazole-3-ylsulfanyl)-quinazolin-4-yl]-thiazolo[5,4-b]pyridin-2-yl-amine,
 (6-phenoxy-quinazolin-4-yl)-thiazolo[5,4-b]pyridin-2-yl-amine,
 [6-(2-fluoro-phenoxy)-quinazolin-4-yl]thiazolo[5,4-b]pyridin-2-yl-amine,
 [6-(1-methyl-1H-imidazol-2-ylsulfanyl)-quinazolin-4-yl]-thiazolo[5,4-b]pyridin-2-yl-amine,
 [6-(pyridin-2-ylsulfanyl)-quinazolin-4-yl]-thiazolo-[5,4-b]pyridin-2-yl-amine,
 [6-(4-methyl-4H-[1,2,4]triazol-3-ylsulfanyl)-quinazolin-4-yl]-(3-methyl-[1,2,4]thiadiazol-5-yl-amine,
 [6-(pyrimidin-2-ylsulfanyl)-quinazolin-4-yl]-thiazolo[5,4-b]pyridin-2-yl-amine,
 [6-(4-methyl-4H-[1,2,4]-triazol-3-ylsulfanyl)-quinazolin-4-yl]-thiazolo[5,4-b]pyridin-2-yl-amine,

[6-(4-methyl-4H-[1,2,4]triazol-3-ylsulfanyl)-quinazolin-4-yl]-thiazol[4,5-b]pyrazin-2-yl-amine,
benzothiazol-2-yl-[6-(4-methyl-4H-[1,2,4]triazol-3-ylsulfanyl)-quinazolin-4-yl]-amine,
[6-(3H-[1,2,3]triazol-4-ylsulfanyl)-quinazolin-4-yl]-thiazolo[5,4-b]pyridin-2-yl -amine,
(1-methyl-1H-pyrazol-3-yl)-[6-(4-methyl-4H-[1,2,4]-triazol-3-ylsulfanyl)-quinazolin-4-yl]-amine,
[6-(4-methyl-4H-[1,2,4]-triazol-3-ylsulfanyl)-quinazolin-4-yl]-pyrimidin-4-yl-amine,
(5-methyl-pyrazin-2-yl)-[6-(4-methyl-4H-[1,2,4]-triazol-3-ylsulfanyl)-quinazolin-4-yl]amine,
[6-(4-methyl-4H-1-[1,2,4]triazol-3-ylsulfanyl)-quinazolin-4-yl]-pyrazin-2-yl-amine,
(5-chloro-thiazol-2-yl)-[6-(4-methyl-4H-[1,2,4]-triazol-3-ylsulfanyl)-quinazolin-4-yl]-amine,
[6-(2-fluoro-1-fluoromethyl-ethoxy)-quinazolin-4-yl]-thiazolo[5,4-b]pyridin-2-yl-amine,
(6-isopropoxy-quinazolin-4-yl)-pyrazin-2-yl-amine,
(6-isopropoxy-quinazolin-4-yl)-thiazolo[5,4-b]pyridin-2-yl-amine,
[6-(2-hydroxy-(1S)-methyl-ethoxy-quinazolin-4-yl)]-thiazolo[5,4-b]pyridin-2-yl-amine,
(6-cyclopentyloxy-quinazolin-4-yl)-thiazolo[5,4-b]-pyridin-2-yl-amine,
[6-(2-fluoro-1-fluoromethyl-ethoxy)-quinazolin-4-yl]-(1-methyl-1H-pyrazol-3-yl)-amine,
[6-(2-fluoro-1-fluoromethyl-ethoxy)-quinazolin-4-yl]-isoxazol-3-yl-amine,
[6-(2-fluoro-1-fluoromethyl-ethoxy)-quinazolin-4-yl]-(5-fluoro-thiazolo-[5,4-b]pyridin-2-yl)-amine,
[6-(2-fluoro-1-fluoromethyl-ethoxy)-quinazolin-4-yl]-(5-methoxy-thiazolo[5,4-b]pyridin-2-yl)-amine,
(6-methoxy-quinazolin-4-yl)-pyrazin-2-yl-amine,
(6-hydroxy-quinazolin-4-yl)-thiazolo[5,4-b]-pyridin-2-yl-amine,
(4-methyl-1,3-thiazol-2-yl)-6-(4-methyl-1,2,4-triazol-3-ylsulfanyl)-quinazolin-4-yl-amine,
(5-methyl-1,3-thiazol-2-yl)-6-(4-methyl-1,2,4-triazol-3-ylsulfanyl)-quinazolin-4-yl-amine,
6-(methylbenzoate-2-yl)sulfanyl-thiazolo[5,4-b]-pyridin-2-ylquinazolin-4-yl-amine,
6-(2-hydroxymethylphenylsulfanyl)-thiazolo[5,4-b]-pyridin-2-ylquinazolin-4-yl-amine,
6-(pyrazin-2-ylsulfanyl)-thiazolo[5,4-b]pyridin-2-ylquinazolin-4-yl-amine,
6-(3-fluoropyridiin-2-ylsulfanyl)-thiazolo[5,4-b]pyridin-2-ylquinazolin-4-yl-amine
6-(benzoate-2-ylsulfanyl)-thiazolo[5,4-b]pyridin-2-ylquinazolin-4-yl-amine,
6-(3-chloropyridin-2-ylsulfanyl)-(1-methylpyrazol-3-yl)quinazolin-4-yl-amine,
[6-(2-dimethylamino-ethylsulfanyl)-quinazolin-4-yl]-thiazolo-[5,4-b]pyridin-2-yl-amine,
[6-(cyclopentylsulfanyl)-quinazolin-4-yl]-thiazolo-[5,4-b]pyridin-4-yl-amine,
[6-(2-fluorophenylsulfanyl)-quinazolin-4-yl]-thiazolo[5,4-b]-pyridin-2-yl -amine,
[6-(2-methoxyphenylsulfanyl)-quinazolin-4-yl]-thiazolo[5,4-b]pyridin-2-yl-amine,
[6-(3-chloropyridin-2-yloxy)-quinazolin-4-yl]-thiazolo[5,4-b]-pyridin-2-yl-amine,
[6-(3-cyanopyridin-2-yloxy)-quinazolin-4-yl]-thiazolo[5,4-b]pyridin-2-yl-amine,
[6-(3-carboxamidopyridin-2-yloxy)-quinzaolin-4-yl]-thiazolo[5,4-b]pyridin-2-yl-amine,
[6-(pyridin-2-yloxy)-quinazolin-4-yl]-thiazolo-[5,4-b]pyridin-2-yl-amine,
[6-(3-methylpyridin-2-yloxy)-quinzaolin-4-yl]-thiazolo[5,4-b]pyridin-2-yl-amine,
[6-(methylcarbamoyl-methyloxy)-quinazolin-4-yl]-thiazolo-[5,4-b]pyridin-2-yl-amine,
[6-(3-methylsulfonylpyridin-2-yloxy)-quinazolin-4-yl]-thiazolo[5,4-b]pyridin-2-yl-amine,
[6-(3-chloropyridin-2-yloxy)-quinazolin-4-yl]-3-methyl-[1,2,4]thiadiazol-5-yl-amine,
[6-(3-fluoropyridin-2-yloxy)-quinazolin-4-yl]-3-methyl-[1,2,4]thiadiazol-5-yl-amine,
[6-(3-chloropyridin-2-yloxy)-quinazolin-4-yl]-pyridin-2-yl-amine,
[6-(tetrahydro-2H-pyran-4-yloxy)-quinazolin-4-yl]-(1-methyl-1H-pyrazol-3-yl)-amine
[6-(3,5-difluoropyridin-2-yloxy)-quinazolin-4-yl]-3-methyl-[1,2,4]thiadiazol-5-yl-amine,
[6-(2-chloro-6-(methylsulfonyl)phenoxy)-quinazolin-4-yl]-(1-methyl-1H-pyrazol-3-yl)-amine,
[6-(2,4-difluorophenoxy)-quinazolin-4-yl](1-methyl-1H-pyrazol-3-yl)-amine,
[6-(2-fluoro-6-(5-methyl-[1,2,4]-oxadiazol-3-yl)-phenoxy)-quinazolin-4-yl]-3-methyl-[1,2,4]-thiadiazol-5-yl-amine,
[6-(2-fluoro-4-(methylsulfonyl)phenoxy)-quinazolin-4-yl-3-methyl-[1,2,4]thiadiazol-5-yl-amine,
[6-(2-fluoro-6-(methylsulfonyl)phenoxy)-quinazolin-4-yl]-(1-methyl-1H-pyrazol-3-yl)-amine,
[6-(2-fluoro-6-(methylsulfonyl)phenoxy)-quinazolin-4-yl]-(1-ethyl-1H-pyrazol-3-yl)-amine,
[6-(2-fluoro-6-(methylsulfonyl)-phenoxy)-quinazolin-4-yl]-pyrazin-2-yl-amine,
[6-(2-chloro-6-(methanesulfonylamino)phenoxy)-quinazolin-4-yl]-(1-methyl-1H-pyrazol-3-yl)-amine,
3-fluoro-2-({4-[(pyrazin-2-yl)amino]quinazolin-6-yl}oxy)benzonitrile,
[6-(butyllacton-2-yloxy)-quinazolin-4-yl]-(1-methyl-1H-pyrazol-3-yl)-amine,
[6-(2,4-difluoro-6-(methylsulfonyl)phenoxy)-quinazolin-4-yl]-(1-methyl-1H-pyrazol-3-yl)-amine,
[6-(2-fluoro-6-(methylsulfonyl)phenoxy)-quinazolin-4-yl]-thiazolo[5,4-b]-pyridin-2-yl-amine,
N-(1-methyl-1H-pyrazol-3-yl)-6-[2-(methylsulfonyl)-phenoxy]quinazolin-6-yl-amine,
3-fluoro-2-({4-[(5-methylpyrazin-2-yl)amino]-quinazolin-6-yl}oxy)benzonitrile,
6-(3-chloropyridin-2-ylsulfanyl)-(1-methylpyrazol-3-yl)quinazolin-4-yl-amine,
6-(3-chloropyridin-2-ylsulfanyl)-(5-methyl-pyrazin-2-yl)quinazolin-4-yl-amine,
6-(3-choropyridin-2-ylsulfanyl)-(1H-pyrazol-3-yl)-quinazolin-4-yl-amine,
6-(acetylpiperidin-4-yl)oxy-N-[1,3]-thiazolo[5,4-d]-pyridin-2-ylquinazolin-4-yl-amine,
N-(1-methyl-1H-1-pyrazol-3-yl)-6-(pyrazin-2-yloxy)-quinazolin-4-yl-amine,
N-(1-methyl-1H-pyrazol-3-yl)-6-(pyrimidin-4-yloxy)-quinazolin-4-yl-amine,
6-[2-fluoro-1-(fluoromethyl)ethoxy]-N-[1,3]thiazol-[5,4-d]pyrimidin-2-ylquinazolin-4-yl-amine,
6-[(3-chloropyridin-2-yl)oxy]-N-1,3-thiazol-2-ylquinazolin-4-amine,
(1-methylpyrazol-3-yl)quinazolin-4-yl-amine,
6-(1,3-benzothiazol-2-yloxy)-N-(1-methyl-1H-pyrazol-3-yl)-quinazolin-4-yJ-amine, N-(1-methyl-1H-pyrazol-3-yl)-6-(quinazolin-2-yloxy)-quinazolin-4-yl-amine,
6-[(5-fluoropyridin-2-yl)oxy]-N-(1-methyl-1H-pyrazol-3-yl)quinazolin-4-yl-amine,
6-[(3-chloropyridin-2-yl)oxy]-N-(5-methyl-1H-pyrazol-3-yl)quinazolin-4-yl-amine,
N-(1-methyl-1H-pyrazol-3-yl)-6-(pyridin-3-yloxy)-quinazolin-4-yl-amine,
6-[(3-chloropyridin-2-yl)oxy]-N-4H-[1,2,4]-triazol-3-ylquinazolin-4-yl-amine,
6-[(5-fluoropyridin-3-yl)oxy]-N-(1-methyl-1H-pyrazol-3-yl)quinazolin-4-yl-amine,
6-[(3-chloropyridin-2-yl)oxy]-N-[1,2,4]-thiadiazol-5-ylquinazolin-4-yl-amine,
N-(1-methyl-1H-pyrazol-3-yl)-6-[(3-methylpyridin-2-yl)oxy]quinazolin-4-yl-amine,
6-{[3-(difluoromethyl)pyridin-2-yl]oxy}-N-(1-methyl-1H-pyrazol-3-yl)quinazolin-4-yl-amine,
N-(1-methyl-1H-pyrazol-3-yl)-6-{[3-(trifluoromethyl)-pyridin-2-yl]oxy}quinazolin-4-yl-amine,
[2-({4-[(1-methyl-1H-pyrazol-3-yl)amino]quinazolin-6-yl}oxy)pyridin-3-yl]methanol,
6-{[3-(fluoromethyl)-pyridin-2-yl]oxy}-N-(1-methyl-1H-pyrazol-3-yl)quinazolin-4-yl-amine,
1-[2-({4-[(1-methyl-1H-pyrazol-3-yl)amino]-quinazolin-6-yl}oxy)pyridin-3-yl]ethanone,
5-chloro-2-methyl-4-({4-[(1-methyl-1H-pyrazol-3-yl)-amino]quinazolin-6-yl}oxy)pyridazin-3(2H)-one,
6-[(6-fluoropyridin-2-yl)oxy]-N-(1-methyl-1H-pyrazol-3-yl)quinazolin-4-yl-amine,
[3-fluoro-2-({4-[(1-methyl-1H-pyrazol-3-yl)amino]quinazolin-6-yl}oxy)phenyl]methanol,
6-[2-fluoro-6-(fluoromethyl)-phenoxy]-N-(1-methyl-1H-pyrazol-3-yl)quinazolin-4-yl-amine,
[3-chloro-4-({4-[(1-methyl-1H-pyrazol-3-yl)amino]-quinazolin-6-yl}oxy)phenyl]methanol,
Methyl 5-(methylsulfonyl)-2-({4-[(3-methyl-[1,2,4]-thiadiazol-5-yl)amino]-quinazolin-6-yl}oxy)benzoate,
3-fluoro-2-({4-[(1-pyridin-2-yl-1H-pyrazol-3-yl)-amino]quinazolin-6-yl}oxy)benzonitrile,
1-[3-fluoro-2-({4-[(1-methyl-1H-pyrazol-3-yl)amino]-quinazolin-6-yl}oxy)phenyl]ethanone,
6-[(3-chloropyridin-2-yl)oxy]-N-[1-(difluoromethyl)-1H-pyrazol-3-yl]quinazolin-4-yl-amine,
3-chloro-N,N-dimethyl-2-({4-[(3-methyl-[1,2,4]-thiadiazol-5-yl)amino]quinazolin-6-yl}oxy)benzenesulfonamide,
6-[2-chloro-6-(ethylsulfonyl)phenoxy]-N-(3-methyl-1,2,4-thiadiazol-5-yl)quinazolin-4-yl-amine,
6-[2-fluoro-6-(methylsulfonyl)phenoxy]-N-(5-methylpyrazin-2-yl)-quinazolin-4-yl-amine,
6-[2-chloro-6-(cyclopropylsulfonyl)-phenoxy]-N-(1-methyl-1H-pyrazol-3-yl)quinazolin-4-yl-amine,
6-[2-fluoro-6-(methylsulfonyl)phenoxy]-N-1H-pyrazol-3-ylquinazolin-4-yl-amine,
6-[3-cyclopropylpyridin-2-yl]oxy]-N-(1-methyl-1H-pyrazol-3-yl)quinazolin-4-yl-amine,
[2-({4-[(1-methyl-1H-pyrazol-3-yl)amino]quinazolin-6-yl}oxy)-3-(trifluoromethyl)phenyl]methanol,
6-[2-fluoro-6-(methylsulfonyl)phenoxy]-N-pyridazin-3-ylquinazolin-4-yl-amine,
N-(5-chloropyrazin-2-yl)-6-[2-fluoro-6-(methylsulfonyl)-phenoxy]quinazolin-4-yl-amine,
[3,5-difluoro-4-({4-[(1-methyl-1H-pyrazol-3-yl)-amino]quinazolin-6-yl}oxy)phenyl]methanol,
3-fluoro-2-({4-[(1-methyl-1H-pyrazol-5-yl)amino]-quinazolin-6-yl}oxy)benzonitrile,
6-[4-methyl-2-(methylsulfonyl)phenoxy]-N-(1-methyl-1H-pyrazol-3-yl)quinazolin-4-yl-amine,
6-(2,6-difluorophenoxy)-N-(1-methyl-pyrazol-3-yl)-quinazolin-4-yl-amine,
1-[3-methyl-2-({4-[(1-methyl-pyrazol-3-yl)amino]-quinazolin-6-yl]oxy)phenyl]ethanone,
6-[2-(fluoromethyl)-6-(methylsulfonyl)phenoxy]-N-(1-methyl-pyrazol-3-yl)quinazolin-4-yl-amine,
3-methyl-2-({4-[(1-methyl-pyrazol-3-yl)amino]-quinazolin-6-yl}oxy)benzonitrile, Cyclopropyl[3-fluoro-2-([4-[{1-methyl-pyrazol-3-yl}-amino]-quinazolin-6-yl]oxy)phenyl]methanone,
6-[2-fluoro-6-(methoxymethyl)phenoxy]-N-(1-methyl-pyrazol-3-yl)quinazolin-4-yl-amine,
[6-(5-chloro-3-fluoropyridin-2-yloxy)-quinazolin-4-yl]-(1-methyl-1H-pyrazol-3-yl)-amine,
[6-(3-fluoropyridin-2-yloxy)-quinazolin-4-yl]-(1-methyl-1H-pyrazol-3-yl)-amine,
6-[2-methyl-6-(methylsulfonyl)-phenoxy]-N-(1-methyl-pyrazol-3-yl)quinazolin-4-yl-amine,
6-[2-(fluoromethyl)-6-(methylsulfonyl)phenoxy]-N-(1H-pyrazol-3-yl)quinazolin-4-yl-amine [or] and
[6-(2-fluoro-6-(methanesulfonamide)phenoxy)-quinazolin-4-yl]-(1-methyl-1H-1-pyrazol-3-yl)-amine.

6. A pharmaceutical composition comprising a compound in accordance with claim 1 in combination with a pharmaceutically acceptable carrier.

* * * * *